(12) United States Patent
Patterson et al.

(10) Patent No.: US 9,701,622 B2
(45) Date of Patent: *Jul. 11, 2017

(54) ANTIBACTERIAL AGENTS

(71) Applicant: Achaogen, Inc., South San Francisco, CA (US)

(72) Inventors: Brian D. Patterson, San Francisco, CA (US); Qing Lu, Foster City, CA (US); James Bradley Aggen, Burlingame, CA (US); Paola Dozzo, San Francisco, CA (US); Ramesh Annasaheb Kasar, Bellevue, WA (US); Martin Sheringham Linsell, San Mateo, CA (US); Timothy Robert Kane, Moss Beach, CA (US); Micah James Gliedt, Sunnyvale, CA (US); Darin James Hildebrandt, Cupertino, CA (US); Glenn A. McEnroe, San Mateo, CA (US); Frederick Cohen, San Francisco, CA (US)

(73) Assignee: Achaogen, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,751

(22) Filed: Jun. 10, 2016

(65) Prior Publication Data

US 2016/0280639 A1    Sep. 29, 2016

Related U.S. Application Data

(63) Continuation of application No. 14/537,048, filed on Nov. 10, 2014, now Pat. No. 9,403,758, which is a continuation of application No. PCT/US2013/040571, filed on May 10, 2013.

(60) Provisional application No. 61/645,439, filed on May 10, 2012.

(51) Int. Cl.
| | |
|---|---|
| *C07D 213/64* | (2006.01) |
| *C07D 333/70* | (2006.01) |
| *C07D 471/04* | (2006.01) |
| *C07D 213/81* | (2006.01) |
| *C07C 259/06* | (2006.01) |
| *C07D 213/79* | (2006.01) |
| *C07C 313/12* | (2006.01) |
| *C07C 317/46* | (2006.01) |
| *C07C 317/50* | (2006.01) |
| *C07C 323/60* | (2006.01) |
| *C07C 317/28* | (2006.01) |
| *C07C 323/42* | (2006.01) |
| *C07C 313/04* | (2006.01) |

(52) U.S. Cl.
CPC .......... *C07C 259/06* (2013.01); *C07C 313/04* (2013.01); *C07C 313/12* (2013.01); *C07C 317/28* (2013.01); *C07C 317/46* (2013.01); *C07C 317/50* (2013.01); *C07C 323/42* (2013.01); *C07C 323/60* (2013.01); *C07D 213/64* (2013.01); *C07D 213/79* (2013.01); *C07D 213/81* (2013.01); *C07D 333/70* (2013.01); *C07D 471/04* (2013.01); *C07C 2101/02* (2013.01); *C07C 2101/04* (2013.01); *C07C 2101/08* (2013.01)

(58) Field of Classification Search
CPC .. C07D 213/64; C07D 333/70; C07D 471/04; C07D 213/81
USPC ................................................ 546/122, 255
See application file for complete search history.

(56) References Cited

U.S. PATENT DOCUMENTS

| | | |
|---|---|---|
| 2,772,281 A | 11/1956 | Holly et al. |
| 5,925,659 A | 7/1999 | Patchett et al. |
| 6,218,389 B1 | 4/2001 | Almstead et al. |
| 6,228,988 B1 | 5/2001 | Floyd et al. |
| 6,281,245 B1 | 8/2001 | Patel et al. |
| 6,358,987 B1 | 3/2002 | Beckett et al. |
| 6,541,276 B2 | 4/2003 | Patel et al. |
| 7,358,359 B2 | 4/2008 | Andersen et al. |
| 7,691,843 B2 | 4/2010 | Raju et al. |
| 7,989,660 B2 | 8/2011 | Andersen et al. |
| 8,084,615 B2 | 12/2011 | Andersen et al. |

(Continued)

FOREIGN PATENT DOCUMENTS

| | | |
|---|---|---|
| CN | 1777577 A | 5/2006 |
| CN | 101209974 A | 7/2008 |

(Continued)

OTHER PUBLICATIONS

Almstead et al., Database CAPLUS on STN, Acc. No. 1999:113626, WO 9906340 (Feb. 11, 1999) (Abstract 2 pages).

(Continued)

*Primary Examiner* — Niloofar Rahmani
(74) *Attorney, Agent, or Firm* — Cooley LLP

(57) ABSTRACT

Antibacterial compounds of formula (I) are provided:

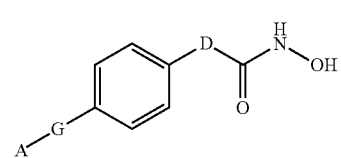

as well as stereoisomers and pharmaceutically acceptable salts thereof; pharmaceutical compositions comprising such compounds; methods of treating bacterial infections by the administration of such compounds; and processes for the preparation of such compounds.

20 Claims, No Drawings

(56) References Cited

U.S. PATENT DOCUMENTS

| | | | |
|---|---|---|---|
| 8,101,640 | B2 | 1/2012 | Andersen et al. |
| 8,153,843 | B2 | 4/2012 | Andersen et al. |
| 9,403,758 | B2* | 8/2016 | Patterson ............ C07D 213/79 |
| 2001/0053555 | A1 | 12/2001 | Patel et al. |
| 2004/0229955 | A1 | 11/2004 | Andersen et al. |
| 2006/0154988 | A1 | 7/2006 | Andersen et al. |
| 2007/0066646 | A1 | 3/2007 | Clauzel et al. |
| 2007/0244197 | A1 | 10/2007 | Andersen et al. |
| 2008/0269221 | A1 | 10/2008 | Andersen et al. |
| 2009/0163496 | A1 | 6/2009 | Andersen et al. |
| 2009/0247506 | A1 | 10/2009 | Andersen et al. |
| 2010/0120872 | A1 | 5/2010 | Dobler et al. |
| 2010/0190766 | A1 | 7/2010 | Moser et al. |
| 2010/0324025 | A1 | 12/2010 | Andersen et al. |
| 2011/0172174 | A1 | 7/2011 | Andersen et al. |
| 2012/0283175 | A1 | 11/2012 | Patten et al. |
| 2015/0018331 | A1 | 1/2015 | Moser et al. |
| 2015/0175530 | A1 | 6/2015 | Patterson et al. |
| 2015/0203444 | A1 | 7/2015 | Trend et al. |

FOREIGN PATENT DOCUMENTS

| | | |
|---|---|---|
| JP | 3155536 | 2/2001 |
| TW | 200706534 A | 5/1995 |
| WO | WO 96/26223 A1 | 8/1996 |
| WO | WO 97/05105 A1 | 2/1997 |
| WO | WO 97/42179 A1 | 11/1997 |
| WO | WO 98/15525 A1 | 4/1998 |
| WO | WO 98/18754 A1 | 5/1998 |
| WO | WO 98/22494 A2 | 5/1998 |
| WO | WO 99/06340 A2 | 2/1999 |
| WO | WO 99/19296 A1 | 4/1999 |
| WO | WO 99/39704 A1 | 8/1999 |
| WO | WO 99/57097 A2 | 11/1999 |
| WO | WO 00/02904 A1 | 1/2000 |
| WO | WO 00/44373 A1 | 8/2000 |
| WO | WO 00/59874 A1 | 10/2000 |
| WO | WO 00/61134 A1 | 10/2000 |
| WO | WO 02/26696 A1 | 4/2002 |
| WO | WO 02/30873 A1 | 4/2002 |
| WO | WO 02/50081 A2 | 6/2002 |
| WO | WO 03/004488 A1 | 1/2003 |
| WO | WO 03/101382 A | 12/2003 |
| WO | WO 2004/007444 A2 | 1/2004 |
| WO | WO 2004/035525 A1 | 4/2004 |
| WO | WO 2004/062601 A2 | 7/2004 |
| WO | WO 2006/127576 A2 | 11/2006 |
| WO | WO 2006/131303 | 12/2006 |
| WO | WO 2007/064732 | 6/2007 |
| WO | WO 2007/069020 | 6/2007 |
| WO | WO 2008/027466 | 3/2008 |
| WO | WO 2008/105515 A1 | 9/2008 |
| WO | WO 2008/154642 | 12/2008 |
| WO | WO 2009/158369 | 12/2009 |
| WO | WO 2010/017060 | 2/2010 |
| WO | WO 2010/024356 | 3/2010 |
| WO | WO 2010/031750 | 3/2010 |
| WO | WO 2010/032147 | 3/2010 |
| WO | WO 2010/100475 | 9/2010 |
| WO | WO 2011/005355 A1 | 1/2011 |
| WO | WO 2011/045703 A2 | 4/2011 |
| WO | WO 2011/073845 A1 | 6/2011 |
| WO | WO 2011/132712 | 10/2011 |
| WO | WO 2012/154204 A1 | 11/2012 |
| WO | WO 2013/039947 A1 | 3/2013 |
| WO | WO 2013/170030 A1 | 11/2013 |
| WO | WO 2013/170165 A1 | 11/2013 |

OTHER PUBLICATIONS

Anderson, "The Process of Structure-Based Drug Design", Chemistry & Biology, 10:787-797 (2003).
Angus et al., "Outer Membrane Permeability in Pseudomonas aeruginosa: Comparison of Wild-type with an Antibiotic-Supersusceptible Mutant", Antimicrob. Agents Chemother., 21(2):299-309 (1982).
Arcadi et al., "Synthesis of New Cardanol Derivatives through Combined Iodination/Palladium-Catalysed Cross-Coupling Reactions", Synthesis, 15:2523-2530 (2006).
Auwers et al., "Uber halogenierte Indazole and Raumisomerie bei freien Indazolen", Berichte der Deutschen Chemischen Gesellschaft, 55(3):1139-1173 (1922). (and English Abstract).
Baker et al., "An Antimalarial Alkaloid from Hydrangea. XV. Synthesis of 5-, 6-, 7-, and 8-Derivatives with Two Identical Substituents", J. Org. Chem., 17(1):149-156, 1952.
Barb et al. , "Inhibition of Lipid A Biosynthesis as the Primary Mechanism of CHIR-090 Antibiotic Activity in Escherichia coli", Biochemistry, 46(12):3793-3802 (2007).
Bergeron et al., "Effects of C-4 Stereochemistry and C-4' Hydroxylation on the Iron Clearing Efficiency and Toxicity of Desferrithiocin Analogues", J. Med. Chem., 42(13):2432-2440 (1999).
Boyce et al., "Total Synthesis of Thiangazole, A Novel Naturally Occurring HIV-1 Inhibitor from Polyangium sp.", Tetrahedron, 51:7321-7330 (1995).
Brooks et al., "Modulators of Leukotriene Biosynthesis and Receptor Activation", J. Med. Chem., 39(14):2629-2654 (1996).
Brown et al., "Potent Inhibitors of LpxC for the Treatment of Gram-Negative Infections", J. Med. Chem., 55(2):914-923 (2012).
Burger's Medicinal Chemistry and Drug Discovery, 5th Ed., vol. 1, Manfred E. Wolff ed., John Wiley & Sons, NY, pp. 975-977 (1995).
Byrne et al., "Antibiotic Treatment of Experimental Pneumonic Plague in Mice", Antimicrob. Agents Chemother., 42(3):675-678 (1998).
CAS Registry Database, CAS Registry 71972-38-8 (1984).
CAS Registry Database, CAS Registry 202273-66-3 (1998).
Charette et al., "Mild Method for the Synthesis of Thiazolines from Secondary and Tertiary Amines", J. Org. Chem., 63(4):908-909 (1998).
Chen et al., "Carbohydroxamido-Oxazolidines: Antibacterial Agents to Target Lipid A Biosynthesis", Bioorg. Med. Chem. Lett., 9:313-318 (1999).
Clements et al., "Antibacterial Activities and Characterization of Novel Inhibitors of LpxC", Antibacterial Agents and Chemotherapy, 46(6):1793-1799 (2002).
Coghlan et al., "A one-pot three-component synthesis of b-nitro-a-amino acids and their N-alkyl derivatives", J. Chem. Soc., Perkin Trans., 1:2659-2660 (1999).
Cuny, G. D., "A new class of UDP-3-O-(R-3-hydroxymyristol)-N-acetylglucosamine deacetylase (LpxC) inhibitors for the treatment of Gram-negative infections: PCT application WO 2008027466", Exp. Opin. Ther. Pat., 19(6):893-899 (2009).
Daku et al, "Suzuki cross-coupling reactions using reverse-phase glass beads in aqueous media", Tetrahedron Lett., 44(27):5095-5098 (2003).
Dong et al., "Total Synthesis of Exochelin MN and Analogues", J. Org. Chem., 67(14):4759-4770 (2002).
Farnum et al., "The Nuclear Magnetic Resonance Spectra of Cyclic 1,3-Diphenylallyl Cations. Some Observations on 1,3-Orbital Interaction", J. Org. Chem., 36(5):698-702 (1971).
Fernandez et al., "Novel Synthesis of 2-Thioazolines", Tetrahedron Lett., 41:3381-3384 (2000).
Fourneau, E., "Amino Alcohols and Derivatives with Therapeutic Properties. II", Database CAPLUS on STN, Acc. No. 1911:22205.
Fushiya et al., "4-N-Hydroxy-L-2,4-diaminobutyric Acid. A Strong Inhibitor of Glutamine Synthetase", J. Med. Chem., 31(2):480-483 (1988).
Galéotti et al., "Synthesis of Peptidyl Aldehydes from Thiazolines", Tetrahedron Lett., 38(14):2459-2462 (1997).
Gallant et al., "Structure-Activity Relationship of Triaryl Propionic Acid Analogues on the Human EP3 Prostanoid Receptor", Bioorg. Med. Chem. Lett., 13(21):3813-3816 (2003).
Goodman & Gilman, "The Pharmacological Basis of Therapeutics", Sixth Edition, pp. 1097-1098 (1980).

(56) References Cited

OTHER PUBLICATIONS

Greco et al., "The Search for Synergy: A Critical Review from a Response Surface Perspective", *Pharmacol. Rev.*, 47(2):331-385 (1995).
Guyton, A.C., "Measurement of the Respiratory Volumes of Laboratory Animals", *Am. J. Physiol.*, 150:70-77 (1947).
Hartings et al., "The automated bioaerosol exposure system: Preclinical platform development and a respiratory dosimetry application with nonhyman primates", *J. Pharmacol. Toxicol. Methods*, 49:39-55 (2004).
Hyland et al., "Cloning, Expression, and Purification of UDP-3-O-Acyl-GlcNAc Deacetylase from Pseudomon as a Metalloamidase of the Lipid a Biosynthesis Pathway", *J. Bacteriol.*, 179(6):2029-2037 (1997).
Ito et al., "Synthetic Reactions by Complex Catalysts. XXXI, A Novel and Versatile Method of Cyclic Imino Ethers and Imino Thioethers", *J. Am. Chem. Soc.*, 95(13):4447-4448 (1973).
Ito et al., "Synthetic Reactions by Complex Catalysts. XXXV. A Facile Synthetic Method of Cyclic Imino Ethers and Imino Thioethers", *Synthetic Comm.*, 4(2):97-103 (1974).
Jackman et al., "Antibacterial agents that target lipid A biosynthesis in gram-negative bacteria. Inhibition of diverse UDP-3-O-(r-3-hydroxymiristoyl)-n-acetylglucosamine deacetylases by substrate analogs containing zinc binding motifs", *J. Biol. Chem.*, 275(15):11002-11009 (2000).
Jeng et al., "Endothelin Converting Enzyme Inhibitors", *Curr. Pharm. Des.*, 3(6):597-614 (1997).
Jones, R. N., "Resistance Patterns Among Nosocomial Pathogens: Trends Over the Past Few Years", *Chest*, 119(Supp 2):397S-404S (2001).
Juaristi et al., "Use of Hexamethylphosphoramide (HMPA) in the Alkylation of Aromatic Amines: Synthesis of Azetidines, Pyrrolidines, Piperidines and Hexahydroazephines", *Tetrahedron*, 45(3):629-636 (1989).
Khan et al., "An Alternative Method for the Synthesis of g-Lactones by Using Cesium Fluoride-Celite/Acetonitrile Combination", *Synthetic Comm.*, 33(19)3:435-3453 (2003).
Khan et al., "A Facile and Convenient Solid-phase Procedure for Synthesizing Nucleoside Hydroxam+A92ic Acids", *Tetrahedron Lett.*, 39:8031-8034 (1998).
Kline et al., "Potent, Novel in Vitro Inhibitors of the Pseudomonas aeruginosa Deacetylase LpxC", *J. Med. Chem.*, 45(14):3112-3129 (2002).
Kline et al., Database CAPLUS on STN, Acc. No. 2002:429779, *J. Med. Chem.*, 45(14):3112-3129 (2002). (Abstract 1 page).
Kleinman, Database CAPLUS on STN, Acc. No. 1997:224101, WO 9705105 (Feb. 13, 1997) (Abstract 1 page).
Krasovitskii et al., "4-(5-aryl-2-oxazolyl)phthalic anhydrides", *Chem. Het. Compounds*, 15(1): 28-31 (1979).
Lee et al., "Species-Specific and Inhibitor-Dependent Conformations of LpxC: Implications for Antibiotic Design", *Chem. Biol.*, 18:38-47 (2011).
Liang et al., "Syntheses, structures and antibiotic activities of LpxC inhibitors based on the diacetylene scaffold", *Bioorg. Med. Chem.* 19:852-860 (2011).
Lopez et al., "Potency and Efficacy of Small Molecule Inhibitors of the Gram-Negative Bacterial Enzyme LpxC Against Yersinia Pestis and Other Enterobacteriaceae", Poster W032, Poster presentation, the Chemical and Biological Defense Science and Technology (CBD S&T) Conference, Dallas, Texas, Nov. 2009 (1 pages).
Lopez et al., "Small Molecule LpxC Inhibitors of Burkholderia Mallei and Burkholderia Psuedomallei: In Vitro and In Vivo Potency and Efficacy", Poster WO33, Poster presentation, the Chemical and Biological Defense Science and Technology (CBD S&T) Conference, Dallas, Texas, Nov. 2009 (1 page).
Matier et al., "Antihypertensive Agents. Synthesis and Biological Properties of 2-Amino-4-aryl-2imidazolines", *J. Med. Chem.* 16(8):901-908 (1973).
Matsuda et al., "Nucleosides and nucleotides. 95. Improved synthesis of 1-(2-azido-2-deoxy-beta-D-arabinofuranosyl)cytosine (cytarazid) and -thymine. Inhibitory spectrum of cytarazid on the growth of various human tumor cells in vitro", *J. Med. Chem.*, 34(3):999-1002 (1991).
May, K. R., "The Collison Nebulizer: Description, Performance and Application", *Aerosol Science*, 4:235-243 (1973).
McClerren et al., "A Slow Tight-Binding Inhibitor of the Zinc-Dependent Deacetylase LpxC of Lipid A Biosynthesis with Antibiotic Activity Comparable to Ciprofloxacin", *Biochemistry*, 44(50):167574-16583 (XP002499759) (2005).
Mellor et al., "N-Fmoc-Aminoxy-2-Chlortrityl Polystyrene Resin: A Facile Solid-Phase Methodology for the synthesis of hydroxyamic acids", *Tetrahedron Lett.*, 38(18):3311-3314 (1997).
Metcalf et al., "Catalytic Irreversible Inhibition of Mammalian Ornithine Decarboxylase (E. C. 4.1.1.17) by Substrate and Product Analogues", *J. Am. Chem. Soc.*, 100(8):2551-2553 (1978).
"Modern Pharmaceutics", 3rd ed., Gilbert S. Banker et al., ed., Marcel Dekker, Inc., NY, p. 596 (1996).
Montgomery et al., "Pyridone Methylsulfone Hydroxamate LpxC Inhibitors for the Treatment of Serious Gram-Negative Infections", *J. Med. Chem.*, 44(4):1662-70 (2012).
Mori et al., "Sonogashira Coupling with Aqueous Ammonia", *Chem. Lett.*, 31(7):756-757 (2002).
Nakatani, S. et al., "Design and synthesis of novel metalloproteinase inhibitors", *Bioorg. Med. Chem.* 14: 5402-5422 (2006).
Neset et al., "Synthesis of Cyclic Hydroxamic Acids by Oxidation of Secondary Amines with Dimethyldioxirane", *Acta Chemica Scandinavica*, 47:1141-1143 (1993).
Neumeyer et al., "Isoquinolines. 2. 3-(Dialkylaminoalkylamino)isoquinolines as Potential Antimalarial Drugs", *J. Med. Chem.*, 13(5):999-1002 (1970).
Ngu and Patel, "A New and Efficient Solid Phase Synthesis of Hydroxamic Acids", *J. Org. Chem.*, 62(21):7088-7089 (1997).
Nicolaus, "Symbiotic Approach to Drug Design", in Decision Making in Drug Research, 173-186, Franz Gross ed. (1983).
Nikaido, H., "Antibacterial Resistance Caused by Gram-negative Multidrug Efflux Pumps", *Clin. Infect. Dis.*, 27(Supp 1):S32-S41 (1998).
Numata et al., "General Synthetic Method for Naphthyridines and Their N-Oxides Containing Isoquinolinic Nitrogen", *Synthesis*, 2:306-3011 (1999).
Onishi et al., "Antibacterial Agents that Inhibit Lipid A Biosynthesis", *Science*, 274:980-982 (1996).
O'Shea et al., "Physicochemical Properties of Antibacterial Compounds: Implications for Drug Discovery", *J. Med. Chem.*, 51(10):2871-2878 (2008).
Oslo (editor), Remington's Pharmaceutical Sciences, Philadelphia College of Pharmaceutical Science, Chapter 27: Structure-Activity Relationship and Drug Design, pp. 420-435 (1990).
Padwa et al., "1,3-Dipolar Cycloadditions of Nitrones Derived from the Reaction of Acetylenes with Hydroxylamines", *J. Org. Chem*, 51(16):3125-3133 (1986).
Patani et al., "Bioisosterism: A Rational Approach in Drug Design", *Chem. Rev.*, 96:3147-3176 (1996).
Patchett et al., Database CAPLUS on STN, Acc. No. 1997:746038, WO 9742179 (Nov. 13, 1997) (Abstract, 2 pages).
Pattenden et al., "Naturally Occurring Linear Fused Thiazoline-Thiazole Containing Metabolites: Total Synthesis of (−) Didehydromirabazole A, a Cytotoxic Alkaloid from Blue-Green Algae", *J.Chem. Soc. Perkin Trans.*, 1:1629-1636 (1993).
Pirrung et al., "A Convenient Procedure for the Preparation of Amino Acid Hydroxamates from Esters", *J. Org. Chem.*, 60(24):8084-8085 (1995).
Pirrung et al., "Inhibition of the antibacterial target UDP-(3-O-acyl)-N-acetylglucosamine deacetylase (LpxC): isoxazoline zinc amidase inhibitors bearing diverse metal binding groups", *J. Med. Chem.*, 45(19):4359-4370 (2002).
Pirrung et al., "High-Throughput Catch-and-Release Synthesis of Oxazoline Hydroxamates. Structure-Activity Relationships in Novel Inhibitors of *Escherichia coli* LpxC: In Vitro Enzyme Inhibition and Antibacterial Properties", *J. Am. Chem. Soc.*, 125(6):1575-1586 (2003).

(56) References Cited

OTHER PUBLICATIONS

Powell et al., "Practical Synthesis of 1-Aryl-6-(hydroxymethyl)-2-ketopiperazines via a 6-exo Amide-Epoxide Cyclization", *Org. Lett.*, 6(22):4069-4072 (2004).
Raman et al., "Titanium (IV)-mediated Tandem Deprotection-cyclodehydration of Protected Cysteine N-Amides: Biomimetic Synthesis of Thiazoline- and Thiazole-containing Heterocycles", *Org. Lett.*, 2(21):3289-3292 (2000).
Righi et al., "Solution- and Solid-Phase Synthesis of 4-Hydroxy-4,5-dihydroisoxazole Derivatives from Enantiomerically Pure N-Tosyl-2,3-aziridine Alcohols", *Org. Lett.*, 4(4):497-500 (2002).
Sahm et al., "Evaluation of Current Activities of Fluoroquinolones Against Gram-Negative Bacilli Using Centralized In Vitro Testing and Electronic Surveillance", *Antimicrob. Agents Chemother.*, 45(1):267-274, (2001).
Sam et al., "Benzoxazoles: Potent Skeletal Muscle Relaxants", *J. Pharm. Sciences*, 53(5):538-544 (1964).
Scribner et al., "Activities of Various βLactams and Aminoglycosides Along and in Combination, Against Isolates of Pseudomonas aeruginosa from Patients with Cystic Fibrosis", *Antimicrob. Agents Chemother.*, 21(6):939-943 (1982).
Shen et al., "Synthesis of 1,3-Diynes via Palladium-catalyzed Reaction of 1,1-Dibromo-1-alkenes", *Org. Lett.*, 2(18):2857-2860 (2000).
Shen et al., "The Stille Reaction of 1,1-Dibromo-1-alkenes: Preparation of Trisubstituted Alkenes and Internal Alkynes", *J. Org. Chem.*, 64(24):8873-8879 (1999).
Sigman et al., "Free Energy and Structure Dependence of Intramolecular Triplet Energy Transfer in Organic Model Compounds", *J. Phys. Chem.*, 95(13):5012-5017 (1991).
Skotnicki et al., "Design Strategies for the Identification of MMP-13 and TACE Inhibitors", *Curr. Opin. Drug Disc. Devel.*, 6(5):742-759 (2003).
Stella et al., "Biotechnology: Pharmaceutical Aspects", *Prodrugs: Challenges and Rewards, Part 1* (2007) (3 pages).
Stobbe et al., "Lichtreaktionen der trans- und cis-Zimtsauren", *Berichte der Deutschen Chemischen Gesellschaft*, 55(8):2225-2245 (1922).
Susse et al., "Chinazolincarbonsauren. VII. Mitteilung. Ein enfacher Zugang zu(4-Oxo-3,4-dihydrochinazolin-3-yl)-alkansauren, (4-Oxo-3,4-dihydro-1,2,3-benzotriazin-3-yl)-alkansauren und deren estern", H*elv. Chim. Acta*, 68:892-899 (1985). (and English Abstract).
Thiel, "Structure-aided drug design's next generation", *Nature Biotechnol.*, 22(5):513-519 (2004).
Vaara et al., "Antibiotic-Supersusceptible Mutants of *Escherichia coli* and *Salmonella typhimurium*", *Antimicrob. Agents Chemother.*, 37(11):2255-2260 (1993).
Vachal et al., "General facile synthesis of 2,5-diarylheteropentalenes", *Tetrahedron Lett.*, 45:7157-7161 (2004).
Van Den Haak et al., "Chichibabin Amination of 1,X-Napthyridines. Nuclear magnetic Resonance Studies on the s Adducts of Heterocyclic Systems with Nucleophiles", *J. Org. Chem.*, 46(10):2134-2137 (1981).
Williams et al., "Drug Design and Relationship of Functional Groups to Pharmacological Activity", Foye's Principles of Medicinal Chemistry, Fifth Edition, Lippincott Williams & Wilkins, 2:59-63 (2002).
Wipf et al., "Thiolysis of Oxazolines: A New, Selective Method for the Direct Conversion of Peptide Oxazolines into Thiazolines", *Tetrahedron Lett.*, 36(36):6395-6398 (1995).
Witte et al., "Cyclische Imidsäureester aus Nitrilen und Aminoalkoholen", *Liebigs Ann. Chem.*, 996-1009 (1974). (and English Abstract).
Wyckoff et al., "Antibacterial and Anti-inflammatory Agents That Target Endotoxin", *Trends Microbiol.*, 6(4):154-159 (1998).
Yoon et al., "Oxygen-Promoted Palladium (II) Catalysis: Facile C(sp2)-C(sp2) Bond Formation via Cross Coupling of Alkenylboronic Compounds and Olefins", *Org. Lett.*, 6(22):4037-4039 (2004).
Young et al., "Leakage of Periplasmic Enzymes from envA1 Strains of *Escherichia coli* ", *J. Bacteriol.*, 173(12):3609-3614 (1991).
Youngman et al., "The Synthesis of Novel cis- α-Substituted-β-aminotetralins", *Synth. Comm.* 33(13):2215-2227 (2003).
Zask et al., "Inhibition of Matrix Metalloproteinases: Structure Based Design", *Curr. Pharm. Des.*, 2(6):624-661 (1996).
Zhang et al., "Design, Combinatorial Chemical Synthesis, and in vitro Characterization of Novel Urea Based Gelatinase Inhibitors", *Bioorg. Med. Chem. Lett.* 9:2823-2826 (1999).
Zhu et al., "Isoquinoline-pyridine-based protein kinase B/Akt antagonists: SAR and in vivo antitumor activity", *Bioorg. Med. Chem. Lett.*, 16(12):3150-3155 (2006).

\* cited by examiner

ANTIBACTERIAL AGENTS

I. CROSS-REFERENCE TO RELATED APPLICATION

This application is a continuation of U.S. application Ser. No. 14/537,048, filed Nov. 10, 2014 (now allowed), which is a continuation of International PCT Application No. PCT/US2013/040571, which was filed on May 10, 2013, which claims the benefit under 35 U.S.C. §119(e) of U.S. Provisional Patent Application No. 61/645,439, filed May 10, 2012. The foregoing applications are incorporated herein by reference in their entireties.

II. BACKGROUND OF THE INVENTION

A. Field of the Invention

This invention pertains generally to treating infections caused by gram-negative bacteria. More specifically, the invention described herein pertains to treating gram-negative infections by inhibiting activity of UDP-3-O—(R-3-hydroxydecanoyl)-N-acetylglucosamine deacetylase (LpxC). The present invention provides small molecule inhibitors of LpxC, pharmaceutical formulations containing such inhibitors, methods of treating subjects with such pharmaceutical formulations, and methods of preparing such pharmaceutical formulations and inhibitors. The invention described herein pertains to treating gram-negative infections by administering compounds capable of inhibiting activity of UDP-3-O—(R-3-hydroxydecanoyl)-N-acetylglucosamine deacetylase (LpxC), either alone or in combination with administering a second antibacterial compound.

B. Introduction

Over the past several decades, the frequency of antimicrobial resistance and its association with serious infectious diseases have increased at alarming rates. The problem of antibacterial resistance is compounded by the existence of bacterial strains resistant to multiple antibacterials. Thus there is a need for new antibacterials, particularly antibacterials with novel mechanisms of action. A previously unexploited but highly conserved target, LpxC, provides a new opportunity for developing broad-spectrum antibacterial small molecules that comprise a new class of active bactericidal chemical entities that should encounter little, if any, naturally-occurring, target-related resistance. LpxC (the enzyme uridyldiphospho-3-O—(R-hydroxydecanoyl)-N-acetylglucosamine deacetylase) is present across all Gram-negative bacterial species of interest and is involved in the first committed step in outer membrane biosynthesis. Thus LpxC is essential for survival and presents an ideal target for antibiotic activity in Gram-negative bacterial species.

Researchers have identified some compounds with antibacterial activity that target lipid A biosynthesis. For example, Jackman et al. (J. Biol. Chem., 2000, 275(15), 11002-11009); Wyckoff et al. (Trends in Microbiology, 1998, 6(4), 154-159); U.S. Patent Application Publication No. 2001/0053555 (published 20 Dec. 2001, corresponding to International PCT Publication No. WO 98/18754, published 7 May 1998); International PCT Publication No. WO 00/61134 (published 19 Oct. 2000); U.S. Patent Application Publication No. 2004/0229955 (published 18 Nov. 2004); International PCT Publication No. WO 2008/027466 (published 6 Mar. 2008); International PCT Publication No. WO 2008/105515 (published 4 Sep. 2008); International PCT Publication No. WO 2008/154642 (published 18 Dec. 2008); International PCT Publication No. WO 2009/158369 (published 30 Dec. 2009); International PCT Publication No. WO 2010/017060 (published 11 Feb. 2010); International PCT Publication No. WO 2010/024356 (published 4 Mar. 2010); International PCT Publication No. WO 2010/031750 (published 25 Mar. 2010); International PCT Publication No. WO 2010/032147 (published 25 Mar. 2010); International PCT Publication No. WO 2010/100475 (published 10 Sep. 2010); International PCT Publication No. WO 2011/045703 (published 21 Apr. 2011); International PCT Publication No. WO 2011/073845 (published 23 Jun. 2011); and International PCT Publication No. WO 2011/132712 (published 27 Oct. 2011) all disclose compounds having antibacterial anti-LpxC activity. The commercial development of these LpxC inhibitors has been complicated by toxicity of these compounds in mammalian animals at concentrations at or near those required for antibacterial activity.

Although there have been advances in the field, there remains a need for LpxC inhibitors that have activity as bactericidal agents against gram-negative bacteria and have an acceptable efficacy and toxicity/tolerance profile. It is, accordingly, an object of this invention to provide compounds and combinations of such compounds for use in the preparation of non-toxic antibacterials and other pharmaceuticals capable of inhibiting gram-negative bacterial infections.

III. BRIEF SUMMARY OF THE INVENTION

The present invention provides novel compounds, pharmaceutical formulations including the compounds, methods of inhibiting UDP-3-O—(R-3-hydroxydecanoyl)-N-acetylglucosamine deacetylase (LpxC), and methods of treating gram-negative bacterial infections.

In one aspect, the invention provides compounds of formula I:

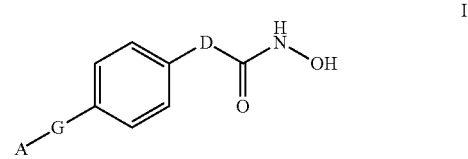

and stereoisomers and, pharmaceutically acceptable salts thereof, wherein

A is selected from the group consisting of:
(a) substituted $C_1$-$C_6$ alkyl, wherein at least one substituent is hydroxy; and
(b) substituted $C_3$-$C_6$ cycloalkyl, wherein at least one substituent is selected from hydroxy and hydroxyalkyl;

G is selected from the group consisting of:

(a) —C≡C—;

(b) —CH=CH—C≡C—;

(c) —C≡C—CH=CH—;

(d) —C≡C—C≡C—;

(e) 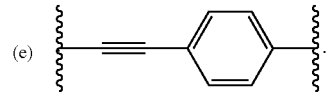

(f) 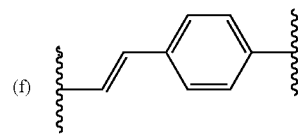

and
(g) phenyl; and
D is selected from the group consisting of:

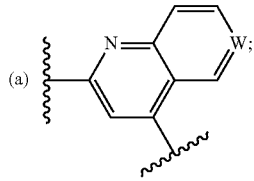

(a)

wherein W is N or N⁺—O⁻;

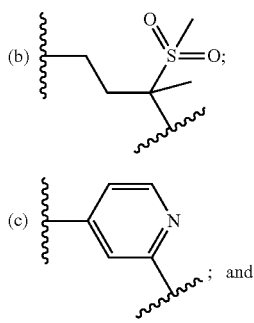

(b)

(c)

; and (d)

wherein
R¹ and R² are each independently selected from hydrogen and methyl; and
E is —C(CH₃)₂SCH₃, —C(CH₃)₂S(O)CH₃, —C(CH₃)₂S(O)₂CH₃, or —C(O)NHCH₃.

In one aspect, the invention provides compounds of formula II:

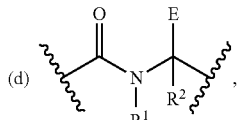

II and stereoisomers and pharmaceutically acceptable salts thereof, wherein
A is selected from the group consisting of:
(a) substituted C₁-C₆ alkyl, wherein at least one substituent is hydroxy; and
(b) substituted C₃-C₆ cycloalkyl, wherein at least one substituent is selected from hydroxy and hydroxyalkyl;
G is selected from the group consisting of:

(a) —C≡C—;
(b) —CH=CH—C≡C—;
(c) —C≡C—CH=CH—;
(d) —C≡C—C≡C—;

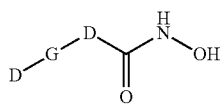

(e)

(f)

and
(g) phenyl; and
D is selected from the group consisting of:

(a)

(b)

(c)

wherein
Q is O or NR, wherein R is hydrogen or an unsubstituted C₁-C₃ alkyl;
R¹ and R² independently are selected from the group consisting of hydrogen, and substituted or unsubstituted C₁-C₃ alkyl, or R¹ and R², together with the carbon atom to which they are attached, form an unsubstituted C₃-C₆ cycloalkyl group or an unsubstituted 4-6 membered heterocyclic group; and
R³ is selected from the group consisting of hydrogen, substituted or unsubstituted C₁-C₆-alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl.

In another aspect, the present invention provides a pharmaceutical composition comprising a compound of Formula I, or a stereoisomer or pharmaceutically acceptable salt thereof, and a pharmaceutically acceptable carrier or diluent.

In another aspect, the present invention provides a pharmaceutical composition comprising a compound of Formula II, or a stereoisomer or pharmaceutically acceptable salt thereof, and a pharmaceutically acceptable carrier or diluent.

In another aspect, the present invention provides a pharmaceutical composition comprising an effective amount of an antibacterial compound of Formula I, or a stereoisomer or pharmaceutically acceptable salt thereof, and a pharmaceutically acceptable carrier or diluent. In another aspect, the present invention provides a pharmaceutical composition comprising an effective amount of an antibacterial compound of Formula II, or a stereoisomer or pharmaceutically acceptable salt thereof, and a pharmaceutically acceptable carrier or diluent.

In another aspect, the present invention provides a method of inhibiting a deacetylase enzyme in gram-negative bacteria, thereby affecting bacterial growth, comprising administering to a subject in need of such inhibition an LpxC-inhibitory compound of Formula I or a stereoisomer or pharmaceutically acceptable salt thereof. In another aspect, the present invention provides a method of inhibiting a deacetylase enzyme in gram-negative bacteria, thereby affecting bacterial growth, comprising administering to a subject in need of such inhibition an LpxC-inhibitory compound of Formula II or a stereoisomer or pharmaceutically acceptable salt thereof.

In another aspect, the present invention provides a method of inhibiting LpxC, thereby modulating the virulence of a bacterial infection, comprising administering to a subject in need of such inhibition an LpxC-inhibitory compound of Formula I or a stereoisomer or pharmaceutically acceptable salt thereof. In another aspect, the present invention provides a method of inhibiting LpxC, thereby modulating the virulence of a bacterial infection, comprising administering to a subject in need of such inhibition an LpxC-inhibitory compound of Formula II or a stereoisomer or pharmaceutically acceptable salt thereof.

In another aspect, the present invention provides a method for treating a subject having a bacterial infection comprising administering to the subject in need thereof an antibacterially effective amount of a compound of Formula I, or a stereoisomer or pharmaceutically acceptable salt thereof. In another aspect, the present invention provides a method for treating a subject having a bacterial infection comprising administering to the subject in need thereof an antibacterially effective amount of a compound of Formula II, or a stereoisomer or pharmaceutically acceptable salt thereof. In a more specific embodiment of the method of treatment, the bacterial infection is a gram-negative bacterial infection. In a further specific embodiment the subject is a mammal and in certain embodiments, a human.

In another aspect, the present invention provides a method of administering an antibacterially effective amount of a compound of Formula I, or a stereoisomer or pharmaceutically acceptable salt thereof, to a subject infected with a fermentative or non-fermentative gram-negative bacteria. In another aspect, the present invention provides a method of administering an antibacterially effective amount of a compound of Formula II, or a stereoisomer or pharmaceutically acceptable salt thereof, to a subject infected with a fermentative or non-fermentative gram-negative bacteria. Examples of such bacteria include *Pseudomonas aeruginosa, Stenotrophomonas maltophila, Burkholderia cepacia, Alcaligenes xylosoxidans, Enterobacteriaceae, Haemophilus, Franciscellaceae* (e.g., *Franciscella tularensis*) and *Neisseria* species.

In another aspect, the present invention provides a method of administering an antibacterially effective amount of a compound of Formula I, or a stereoisomer or pharmaceutically acceptable salt thereof, to a subject infected with gram-negative bacteria. In another aspect, the present invention provides a method of administering an antibacterially effective amount of a compound of Formula II, or a stereoisomer or pharmaceutically acceptable salt thereof, to a subject infected with gram-negative bacteria. Examples of such bacteria include *Enterobacteriaceae*, such as *Serratia, Proteus, Klebsiella, Enterobacter, Citrobacter, Salmonella, Providencia, Yersinia* (e.g., *Yersinia pestis*), *Morganella, Cedecea, Edwardsiella* species and *Escherichia coli*.

These and other aspects of the invention will be evident upon reference to the following detailed description.

IV. DETAILED DESCRIPTION OF THE INVENTION

The present invention provides novel compounds, methods for inhibiting LpxC in gram-negative bacteria, and novel methods for treating bacterial infections. The compounds provided herein can be formulated into pharmaceutical formulations and medicaments that are useful in the methods of the invention. The invention also provides for the use of the compounds in preparing medicaments and pharmaceutical formulations, for use of the compounds in inhibiting LpxC, and for use of the compounds in treating bacterial infections in a subject. The invention further provides compositions and methods for treating gram-negative infections by administering compounds capable of inhibiting activity of UDP-3-O—(R-3-hydroxydecanoyl)-N-acetylglucosamine deacetylase (LpxC), either alone or in combination with administering a second antibacterial compound A. Definitions The following abbreviations and definitions are used throughout this application:

"LpxC" is an abbreviation that stands for UDP-3-O—(R-3-hydroxydecanoyl)-N-acetylglucosamine deacetylase.

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkoxy" refers to the group —O-alkyl, wherein alkyl is as defined herein. Alkoxy includes methoxy, ethoxy, n-propoxy, isopropoxy, n-butoxy, t-butoxy, sec-butoxy, n-pentoxy, and the like.

"Amino" refers to the group —$NH_2$.

"Primary alcohol" refers to the group -alkyl-OH, wherein the hydroxyl radical is connected to a primary carbon. Examples include —$CH_2OH$ (hydroxymethyl), —$CH_2CH_2OH$ (hydroxymethyl) and —$CH(CH_3)CH_2OH$ (1-hydroxypropan-2-yl).

"Alkenyl" refers to straight chain or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic —C≡C— unsaturation. Examples of such alkynyl groups include acetylenyl (—C≡CH), and propargyl (—CH$_2$C≡CH).

"Carboxyl" or "carboxy" refers to —COOH or salts thereof.

"Cyano" or "nitrile" refers to the group —CN.

"Cycloalkyl" refers to cyclic alkyl groups of from 3 to 13 carbon atoms having single. Examples of cycloalkyl groups include cyclopropyl, cyclobutyl, cyclopentyl, cyclooctyl, and the like.

"Guanidino" refers to the group —NHC(=NH)NH$_2$.

"Halo" or "halogen" refers to fluoro, chloro, bromo, and iodo and is typically fluoro or chloro.

"Hydroxy" or "hydroxyl" refers to the group —OH.

"Heterocycle," "heterocyclic," and "heterocyclyl" refer to a saturated or unsaturated group having a single ring, and having from 3 to 15 ring atoms, including 1 to 4 hetero atoms. These ring atoms are selected from the group consisting of nitrogen, sulfur, or oxygen. In one implementation, the nitrogen and/or sulfur atom(s) of the heterocyclic group are optionally oxidized to provide for the N-oxide, —S(O)—, or —SO$_2$— moieties.

"Nitro" refers to the group —NO$_2$.

"Nitroso" refers to the group —NO.

"Oxo" refers to the atom (=O).

"Substituted" refers to a group having one or more hydrogens replaced with substituents selected from the group consisting of alkoxy, acyl, acylamino, acyloxy, amino, aminocarbonyl, aminothiocarbonyl, aminocarbonylamino, aminothiocarbonylamino, aminocarbonyloxy, amidino, carboxyl, carboxyl ester, (carboxyl ester)amino, (carboxyl ester)oxy, cyano, guanidino, halo, hydroxy, nitro, SO$_3$H, sulfonyl, sulfonyloxy, thioacyl, thiol, and alkylthio, wherein said substituents are as defined herein. In certain substituted cyclic groups, "substituted" also refers to a group having two hydrogens replaced with a single double bonded oxygen atom (an oxo group) or a single double bonded sulfur atom (thioxo). In some implementations, the substituted group has 1 to 3 of the aforementioned substituents. In other implementations, the substituted group has 1 to 2 of the aforementioned substituents "Sulfonyl" refers to the group —SO$_2$-alkyl, —SO$_2$-substituted alkyl, —SO$_2$— alkenyl, —SO$_2$-substituted alkenyl, wherein alkyl, substituted alkyl, alkenyl, substituted alkenyl, alkynyl, and substituted alkynyl are as defined herein. Sulfonyl includes groups such as methyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-alkynyl, —OSO$_2$-substituted alkynyl, wherein alkyl, substituted alkyl, alkenyl, substituted alkenyl, alkynyl, and substituted alkynyl are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, and substituted alkynyl-C(S)—, wherein alkyl, substituted alkyl, alkenyl, substituted alkenyl, alkynyl, and substituted alkynyl are as defined herein.

"Thiol" refers to the group —SH.

"Thioxo" refers to the atom (=S).

"Alkylthio" refers to the group —S-alkyl, wherein alkyl is as defined herein. In other implementations, sulfur may be oxidized to —S(O)—. The sulfoxide may exist as one or more stereoisomers.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

Generally, reference to a certain element such as hydrogen or H is meant to include all isotopes of that element. For example, if a substituent group is defined to include hydrogen or H, it also includes deuterium and tritium.

The subject invention also includes isotopically-labeled compounds of the present invention, that are structurally identical to those disclosed herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$F, $^{32}$F, $^{35}$S, $^{18}$ and $^{36}$Cl, respectively. Compounds of the present invention, prodrugs thereof, and pharmaceutically acceptable salts of said compounds and of said prodrugs that contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

"Subject" refers to human and non-human animals, especially mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, phosphate, sulfate and the like.

"Pharmaceutically effective amount" and "therapeutically effective amount" refer to an amount of a compound sufficient to treat a specified disorder or disease or one or more of its symptoms and/or to prevent the occurrence of the disease or disorder.

"Co-administration" can be in the form of a single formulation (combining, for example, a compound of the present invention and a second antibacterial agent with pharmaceutically acceptable excipients, optionally segregating the two active ingredients in different excipient mixtures designed to independently control their respective release rates and durations) or by independent administration of separate formulations containing the active agents. "Coadministration" further includes concurrent administration (administration of a compound of the present invention and a second antibacterial agent at the same time) and time varied administration (administration of a compound of the present invention at a time different from that of the second antibacterial agent), as long as both the compound of the present invention and the second antibacterial agent are present in the body in therapeutically effective concentrations during at least partially overlapping times.

The term "antibacterial agent" refers to agents that have either bactericidal or bacteriostatic activity. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

B. Compounds, Compositions and Use Thereof

In one aspect, the invention provides compounds of formula I:

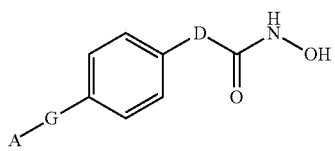

and stereoisomers, pharmaceutically acceptable salts, and esters thereof, wherein A is selected from the group consisting of:
(a) substituted $C_1$-$C_6$ alkyl, wherein at least one substituent is hydroxy; and
(b) substituted $C_3$-$C_6$ cycloalkyl, wherein at least one substituent is selected from hydroxy and hydroxyalkyl;

G is selected from the group consisting of:

 (a)

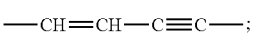 (b)

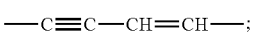 (c)

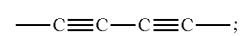 (d)

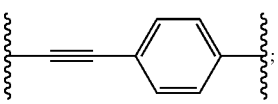 (e)

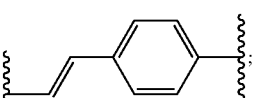 (f)

and
(g) phenyl; and
D is selected from the croup consisting of:

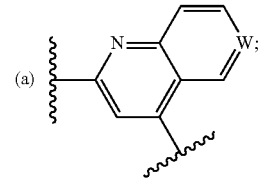 (a)

wherein W is N or $N^+$—$O^-$;

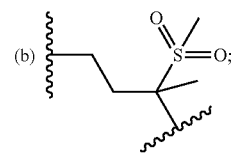 (b)

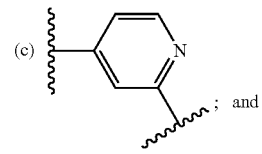 (c) ; and

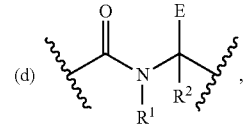 (d) , wherein
$R^1$ and $R^2$ are each independently selected from hydrogen and methyl; and
E is —$C(CH_3)_2SCH_3$, —$C(CH_3)_2S(O)CH_3$, —$C(CH_3)_2S(O)_2CH_3$, or —$C(O)NHCH_3$.

In one aspect, the invention provides compounds of formula II:

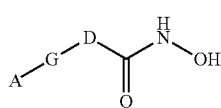

II and stereoisomers, pharmaceutically acceptable salts, and esters thereof, wherein A is selected from the group consisting of:
(a) substituted $C_1$-$C_6$ alkyl, wherein at least one substituent is hydroxy; and
(b) substituted $C_3$-$C_6$ cycloalkyl, wherein at least one substituent is selected from hydroxy and hydroxyalkyl;

G is selected from the group consisting of:

(a) —C≡C—;
(b) —CH=CH—C≡C—;
(c) —C≡C—CH=CH—;
(d) —C≡C—C≡C—;

(e) 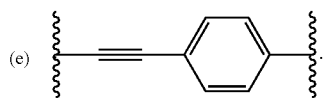

(f) 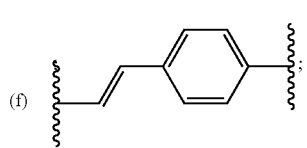

and
(g) phenyl; and

D is selected from the group consisting of:

(a) 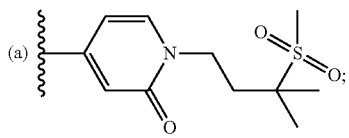

(b) 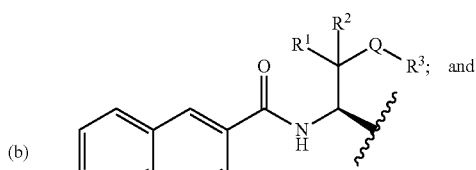

(c) 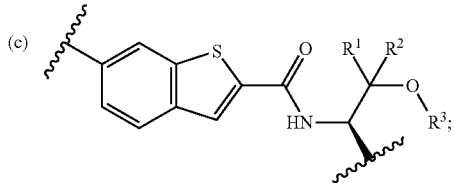

wherein
Q is O or NR, wherein R is hydrogen or an unsubstituted $C_1$-$C_3$ alkyl;

$R^1$ and $R^2$ independently are selected from the group consisting of hydrogen, and substituted or unsubstituted $C_1$-$C_3$ alkyl, or $R^1$ and $R^2$, together with the carbon atom to which they are attached, form an unsubstituted $C_3$-$C_6$ cycloalkyl group or an unsubstituted 4-6 membered heterocyclic group; and $R^3$ is selected from the group consisting of hydrogen, substituted or unsubstituted $C_1$-$C_6$-alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl.

In certain embodiments, A is substituted $C_1$-$C_6$ alkyl, wherein at least one substituent is hydroxy. In certain embodiments, A is substituted $C_1$-$C_6$ alkyl, wherein at least two substituents are hydroxy. For example, in certain embodiments A is hydroxymethyl, hydroxyethyl, hydroxypropyl or dihydroxpropyl.

In other embodiments, A is substituted $C_3$-$C_6$ cycloalkyl, wherein at least one substituent is selected from hydroxy and hydroxyalkyl. In certain embodiments, A is substituted $C_3$-$C_6$ cycloalkyl, wherein at least one substituent is hydroxymethyl. For example, in certain embodiments A is hydroxymethylcyclopropyl. In other embodiments, A is substituted $C_3$-$C_6$ cycloalkyl, wherein at least one substiuent is hydroxy.

In certain embodiments, G is —C≡C—C≡C—.

In certain embodiments of compounds of Formula I, D is

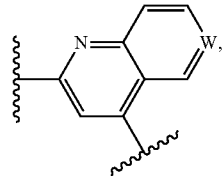

wherein W is N or $N^+$—$O^-$. In other embodiments of compounds of Formula I, D is

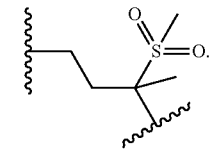 [SMILES: *CCC(*)(C)S(C)(=O)=O]

In still other embodiments of compounds of Formula I, D is

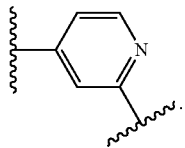 [SMILES: *c1ccnc(*)c1]

Finally, in still other embodiments of compounds of Formula I, D is

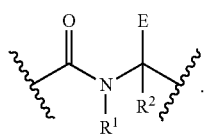

In certain embodiments, $R^1$ is hydrogen. Similarly, in certain embodiments, $R^2$ is hydrogen. In certain embodiments of compounds of Formula I, E is —C(CH$_3$)$_2$SCH$_3$. In other embodiments, E is —C(CH$_3$)$_2$S(O)$_2$CH$_3$. In still other embodiments, E is —C(CH$_3$)$_2$S(O)CH$_3$. In still other embodiments, E is —C(O)NHCH$_3$. The compounds of the invention include the compounds of Table I below.

TABLE 1

| # | structure | name |
|---|---|---|
| 1 | 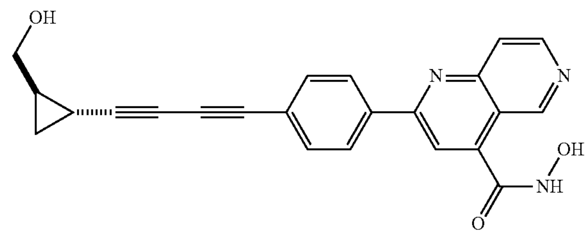 [SMILES: O=C(NO)c1cc(-c2ccc(C#CC#C[C@@H]3C[C@H]3CO)cc2)nc2ccncc12] | N-hydroxy-2-(4-(((trans)-2-(hydroxymethyl)cyclopropyl)buta-1,3-diynyl)phenyl)-1,6-naphthyridine-4-carboxamide |
| 2 | 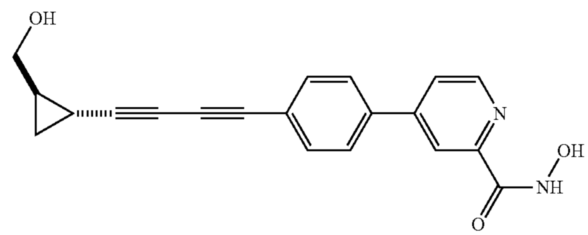 [SMILES: O=C(NO)c1cc(-c2ccc(C#CC#C[C@@H]3C[C@H]3CO)cc2)ccn1] | N-hydroxy-4-(4-(((trans)-2-(hydroxymethyl)cyclopropyl)buta-1,3-diynyl)phenyl)picolinamide |
| 3 | 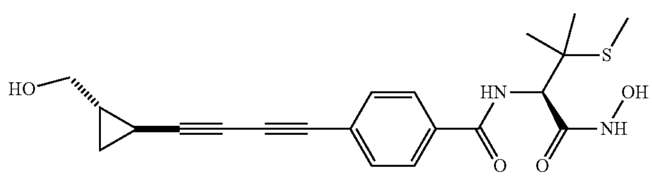 [SMILES: CSC(C)(C)[C@H](NC(=O)c1ccc(C#CC#C[C@H]2C[C@@H]2CO)cc1)C(=O)NO] | N-((R)-1-(hydroxyamino)-3-methyl-3-(methylthio)-1-oxobutan-2-yl)-4-(((trans)-2-(hydroxymethyl)cyclopropyl)buta-1,3-diynyl)benzamide |
| 4 | 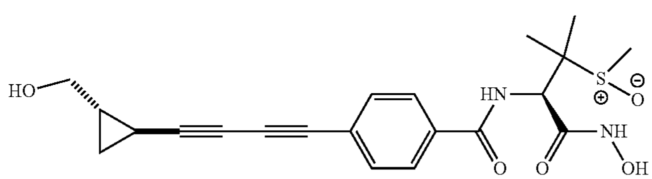 [SMILES: C[S+]([O-])C(C)(C)[C@H](NC(=O)c1ccc(C#CC#C[C@H]2C[C@@H]2CO)cc1)C(=O)NO] | N-((2R)-1-(hydroxyamino)-3-methyl-3-(methylsulfinyl)-1-oxobutan-2-yl)-4-(((trans)-2-(hydroxymethyl)cyclopropyl)buta-1,3-diynyl)benzamide |
| 5 | 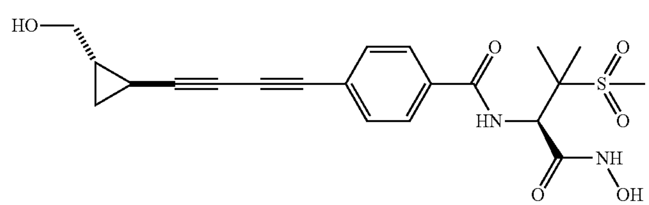 [SMILES: CC(C)([C@H](NC(=O)c1ccc(C#CC#C[C@H]2C[C@@H]2CO)cc1)C(=O)NO)S(C)(=O)=O] | N-((R)-1-(hydroxyamino)-3-methyl-3-(methylsulfonyl)-1-oxobutan-2-yl)-4-(((trans)-2-(hydroxymethyl)cyclopropyl)buta-1,3-diynyl)benzamide |
| 6 | 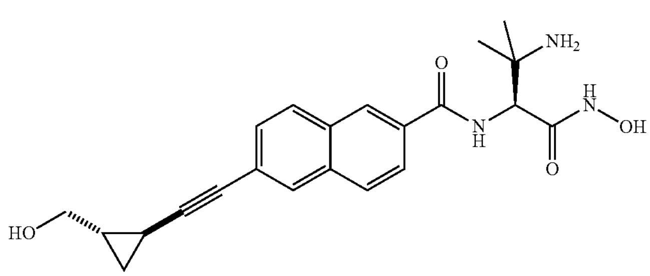 [SMILES: CC(C)(N)[C@H](NC(=O)c1ccc2cc(C#C[C@H]3C[C@@H]3CO)ccc2c1)C(=O)NO] | N-((S)-3-amino-1-(hydroxyamino)-3-methyl-1-oxobutan-2-yl)-6-(((trans)-2-(hydroxymethyl)cyclopropyl)ethynyl)-2-naphthamide |

TABLE 1-continued

| # | structure | name |
|---|---|---|
| 7 | 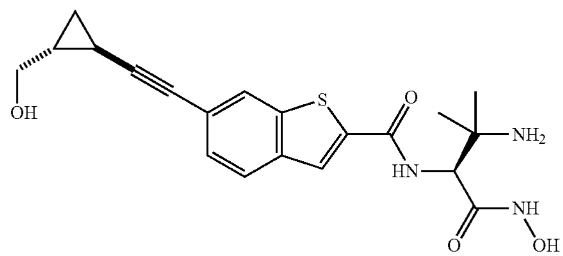 | N-((S)-3-amino-1-(hydroxyamino)-3-methyl-1-oxobutan-2-yl)-6-(((trans)-2-(hydroxymethyl)cyclopropyl)ethynyl)benzo[b]thiophene-2-carboxamide |
| 8 | 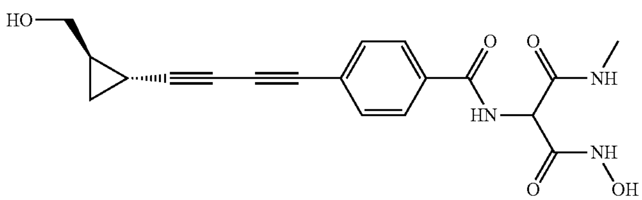 [SMILES: CNC(=O)C(NC(=O)c1ccc(C#CC#C[C@@H]2C[C@H]2CO)cc1)C(=O)NO] | N1-hydroxy-2-(4-(((1R,2R)-2-(hydroxymethyl)cyclopropyl)buta-1,3-diynyl)benzamido)-N3-methylmalonamide |
| 9 | 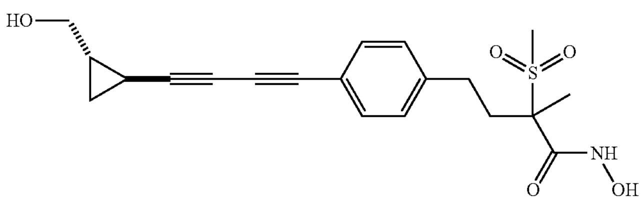 [SMILES: CC(CCc1ccc(C#CC#C[C@H]2C[C@@H]2CO)cc1)(C(=O)NO)S(C)(=O)=O] | N-hydroxy-4-(4-(((trans)-2-(hydroxymethyl)cyclopropyl)buta-1,3-diynyl)phenyl)-2-methyl-2-(methylsulfonyl)butanamide |
| 10 | 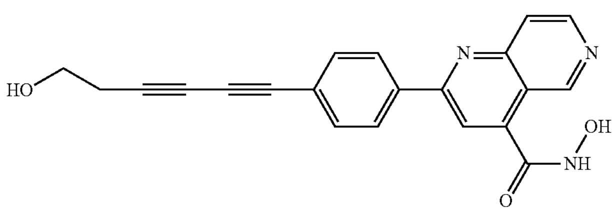 [SMILES: O=C(NO)c1cc(-c2ccc(C#CC#CCCO)cc2)nc2ccncc12] | N-hydroxy-2-(4-(6-hydroxyhexa-1,3-diynyl)phenyl)-1,6-naphthyridine-4-carboxamide |
| 11 | 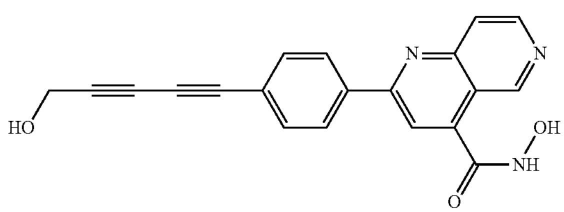 [SMILES: O=C(NO)c1cc(-c2ccc(C#CC#CCO)cc2)nc2ccncc12] | N-hydroxy-2-(4-(5-hydroxypenta-1,3-diynyl)phenyl)-1,6-naphthyridine-4-carboxamide |
| 12 | 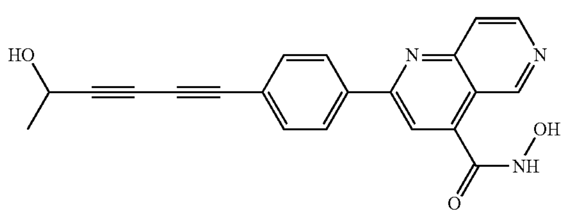 [SMILES: CC(O)C#CC#Cc1ccc(-c2cc(C(=O)NO)c3cnccc3n2)cc1] | N-hydroxy-2-(4-(5-hydroxyhexa-1,3-diynyl)phenyl)-1,6-naphthyridine-4-carboxamide |
| 13 | 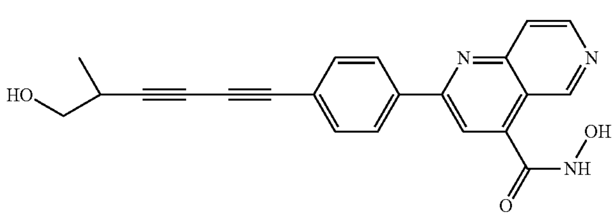 [SMILES: CC(C#CC#Cc1ccc(-c2cc(C(=O)NO)c3cnccc3n2)cc1)CO] | N-hydroxy-2-(4-(6-hydroxy-5-methylhexa-1,3-diynyl)phenyl)-1,6-naphthyridine-4-carboxamide |

TABLE 1-continued

| # | structure | name |
|---|---|---|
| 14 | 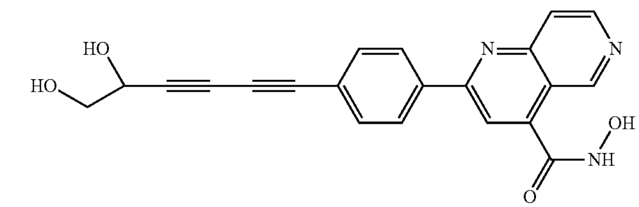 | 2-(4-(5,6-dihydroxyhexa-1,3-diynyl)phenyl)-N-hydroxy-1,6-naphthyridine-4-carboxamide |
| 15 | 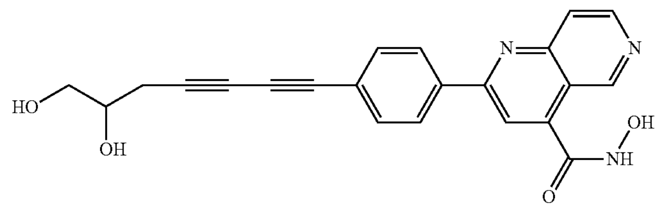 [SMILES: O=C(NO)c1cc(-c2ccc(C#CC#CCC(O)CO)cc2)nc2ccncc12] | 2-(4-(6,7-dihydroxyhepta-1,3-diynyl)phenyl)-N-hydroxy-1,6-naphthyridine-4-carboxamide |
| 16 | 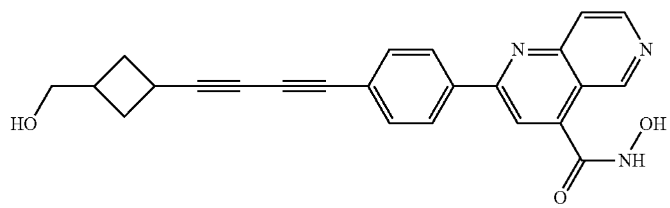 [SMILES: O=C(NO)c1cc(-c2ccc(C#CC#CC3CC(CO)C3)cc2)nc2ccncc12] | N-hydroxy-2-(4-((3-(hydroxymethyl)cyclobutyl)buta-1,3-diynyl)phenyl)-1,6-naphthyridine-4-carboxamide |
| 17 | 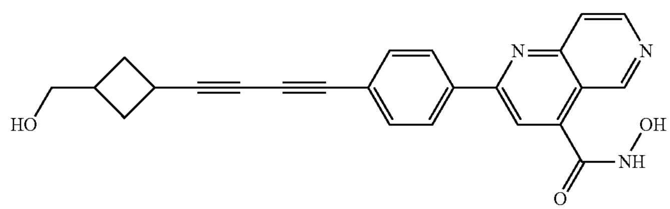 [SMILES: O=C(NO)c1cc(-c2ccc(C#CC#CC3CC(CO)C3)cc2)nc2ccncc12] | N-hydroxy-2-(4-((3-(hydroxymethyl)cyclobutyl)buta-1,3-diynyl)phenyl)-1,6-naphthyridine-4-carboxamide |
| 18 | 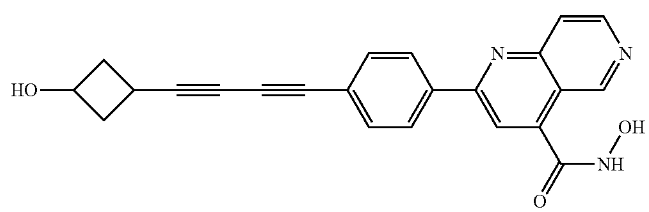 [SMILES: O=C(NO)c1cc(-c2ccc(C#CC#CC3CC(O)C3)cc2)nc2ccncc12] | N-hydroxy-2-(4-((3-hydroxycyclobutyl)buta-1,3-diynyl)phenyl)-1,6-naphthyridine-4-carboxamide |
| 19 | 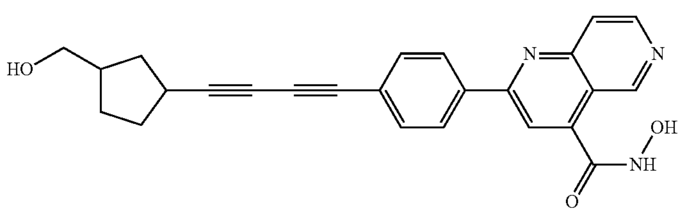 [SMILES: O=C(NO)c1cc(-c2ccc(C#CC#CC3CCC(CO)C3)cc2)nc2ccncc12] | N-hydroxy-2-(4-((3-(hydroxymethyl)cyctopentyl)buta-1,3-diynyl)phenyl)-1,6-naphthyridine-4-carboxamide |
| 20 | 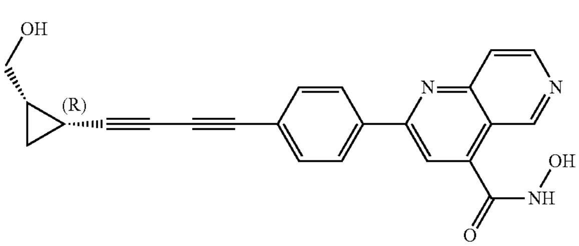 | N-hydroxy-2-(4-(((1R,2S)-2-(hydroxymethyl)cyclopropyl)buta-1,3-diynyl)phenyl)-1,6-naphthyridine-4-carboxamide |

TABLE 1-continued

| # | structure | name |
|---|-----------|------|
| 21 | 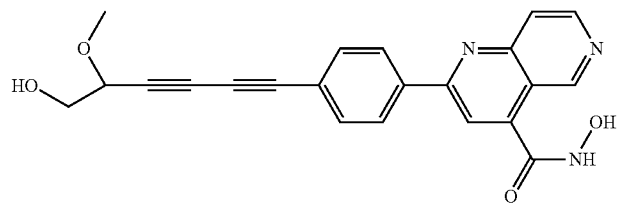 [SMILES: COC(C#CC#Cc1ccc(-c2cc(C(=O)NO)c3cnccc3n2)cc1)CO] | N-hydroxy-2-(4-(6-hydroxy-5-methoxyhexa-1,3-diynyl)phenyl)-1,6-naphthyridine-4-carboxamide |
| 22 | 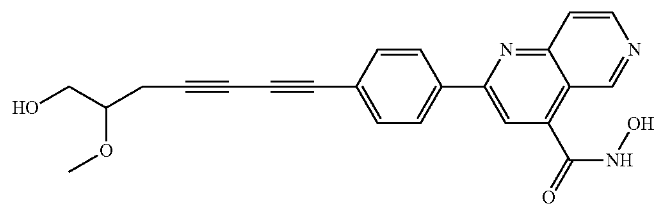 [SMILES: COC(CO)CC#CC#Cc1ccc(-c2cc(C(=O)NO)c3cnccc3n2)cc1] | N-hydroxy-2-(4-(7-hydroxy-6-methoxyhepta-1,3-diynyl)phenyl)-1,6-naphthyridine-4-carboxamide |
| 23 | 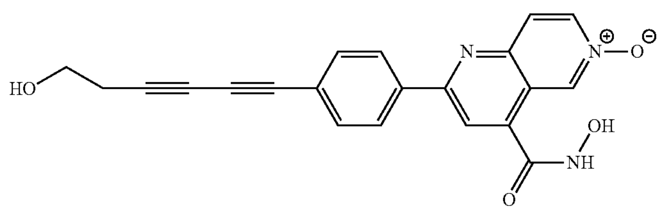 [SMILES: O=C(NO)c1cc(-c2ccc(C#CC#CCCO)cc2)nc2cc[n+]([O-])cc12] | 4-(hydroxycarbamoyl)-2-(4-(6-hydroxyhexa-1,3-diynyl)phenyl)-1,6-naphthyridine 6-oxide |
| 24 | 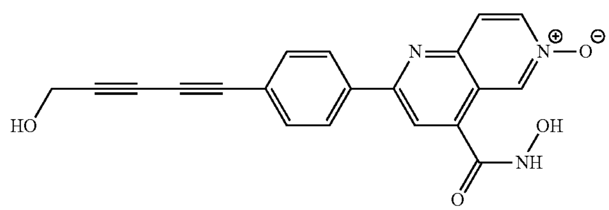 [SMILES: O=C(NO)c1cc(-c2ccc(C#CC#CCO)cc2)nc2cc[n+]([O-])cc12] | 4-(hydroxycarbamoyl)-2-(4-(5-hydroxypenta-1,3-diynyl)phenyl)-1,6-naphthyridine 6-oxide |
| 25 | 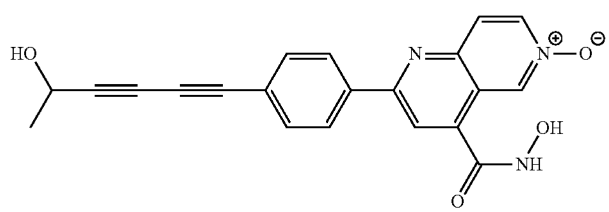 [SMILES: CC(O)C#CC#Cc1ccc(-c2cc(C(=O)NO)c3c[n+]([O-])ccc3n2)cc1] | 4-(hydroxycarbamoyl)-2-(4-(5-hydroxyhexa-1,3-diynyl)phenyl)-1,6-naphthyridine 6-oxide |
| 26 | 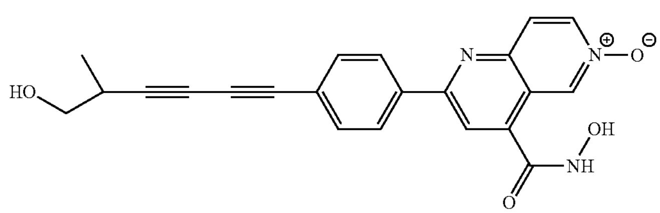 [SMILES: CC(C#CC#Cc1ccc(-c2cc(C(=O)NO)c3c[n+]([O-])ccc3n2)cc1)CO] | 2-(4-(6-hydroxy-5-methylhexa-1,3-diynyl)phenyl)-4-(hydroxycarbamoyl)-1,6-naphthyridine 6-oxide |
| 27 | 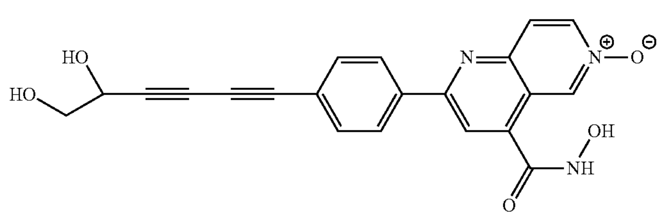 [SMILES: O=C(NO)c1cc(-c2ccc(C#CC#CC(O)CO)cc2)nc2cc[n+]([O-])cc12] | 2-(4-(5,6-dihydroxyhexa-1,3-diynyl)phenyl)-4-(hydroxycarbamoyl)-1,6-naphthyridine 6-oxide |

TABLE 1-continued

| # | structure | name |
|---|---|---|
| 28 | 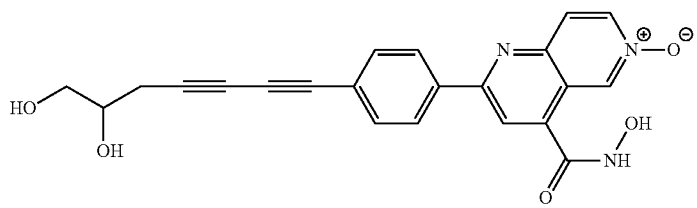 [SMILES: O=C(NO)c1cc(-c2ccc(C#CC#CCC(O)CO)cc2)nc2cc[n+]([O-])cc12] | 2-(4-(6,7-dihydroxyhepta-1,3-diynyl)phenyl)-4-(hydroxycarbamoyl)-1,6-naphthyridine 6-oxide |
| 29 | 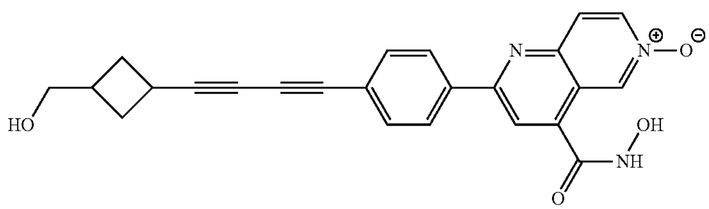 [SMILES: O=C(NO)c1cc(-c2ccc(C#CC#CC3CC(CO)C3)cc2)nc2cc[n+]([O-])cc12] | 4-(hydroxycarbamoyl)-2-(4-((3-(hydroxymethyl)cyclobutyl)buta-1,3-diynyl)phenyl)-1,6-naphthyridine 6-oxide |
| 30 | 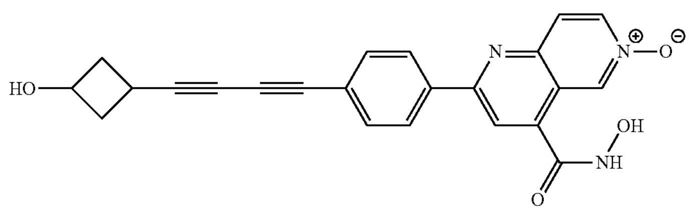 [SMILES: O=C(NO)c1cc(-c2ccc(C#CC#CC3CC(O)C3)cc2)nc2cc[n+]([O-])cc12] | 4-(hydroxycarbamoyl)-2-(4-((3-hydroxycyclobutyl)buta-1,3-diynyl)phenyl)-1,6-naphthyridine 6-oxide |
| 31 | 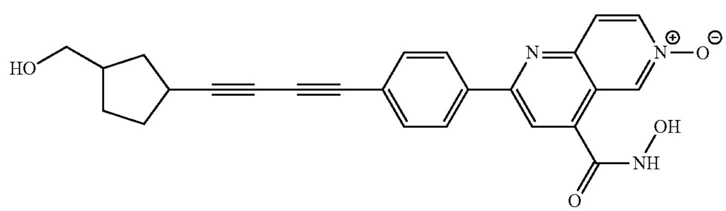 [SMILES: O=C(NO)c1cc(-c2ccc(C#CC#CC3CCC(CO)C3)cc2)nc2cc[n+]([O-])cc12] | 4-(hydroxycarbamoyl)-2-(4-((3-(hydroxymethyl)cyclopentyl)buta-1,3-diynyl)phenyl)-1,6-naphthyridine 6-oxide |
| 32 | 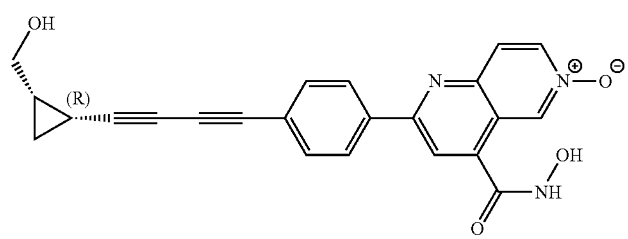 | 4-(hydroxycarbamoyl)-2-(4-(((1R,2S)-2-(hydroxymethyl)cyclopropyl)buta-1,3-diynyl)phenyl)-1,6-naphthyridine 6-oxide |
| 33 | 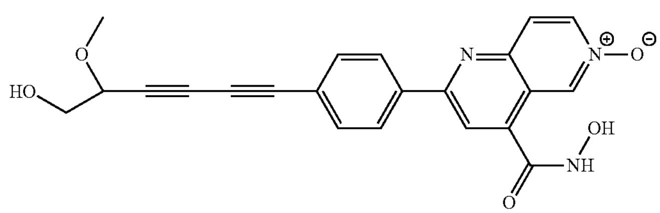 [SMILES: COC(C#CC#Cc1ccc(-c2cc(C(=O)NO)c3c[n+]([O-])ccc3n2)cc1)CO] | 2-(4-(6-hydroxy-5-methoxyhexa-1,3-diynyl)phenyl)-4-(hydroxycarbamoyl)-1,6-naphthyridine 6-oxide |
| 34 | 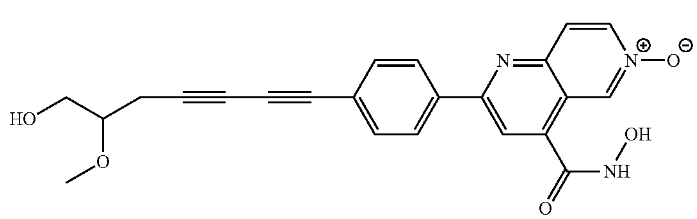 | 2-(4-(7-hydroxy-6-methoxyhepta-1,3-diynyl)phenyl)-4-(hydroxycarbamoyl)-1,6-naphthyridine 6-oxide |

TABLE 1-continued

| # | structure | name |
|---|---|---|
| 35 | 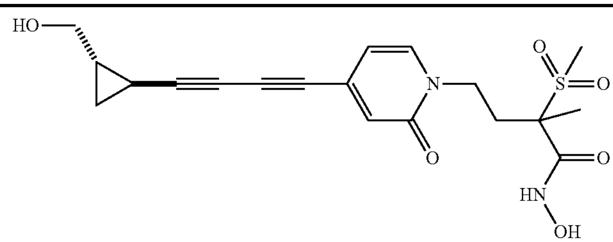 | N-hydroxy-4-(4-(((1S,2S)-2-(hydroxymethyl)cyclopropyl)buta-1,3-diynyl)-2-oxopyridin-1(2H)-yl)-2-methyl-2-(methylsulfonyl)butanamide |
| 36 | 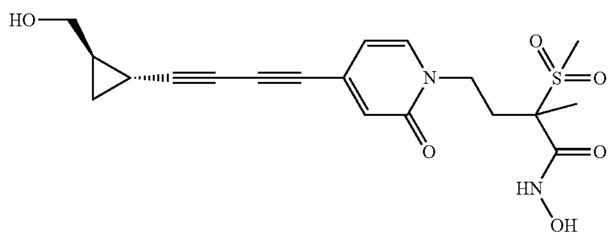 [SMILES: CC(CCn1ccc(C#CC#C[C@@H]2C[C@H]2CO)cc1=O)(C(=O)NO)S(C)(=O)=O] | N-hydroxy-4-(4-(((1R,2R)-2-(hydroxymethyl)cyclopropyl)buta-1,3-diynyl)-2-oxopyridin-1(2H)-yl)-2-methyl-2-(methylsulfonyl)butanamide |
| 37 | 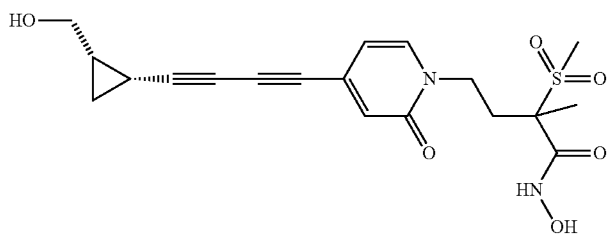 [SMILES: CC(CCn1ccc(C#CC#C[C@@H]2C[C@@H]2CO)cc1=O)(C(=O)NO)S(C)(=O)=O] | N-hydroxy-4-(4-(((1R,2S)-2-(hydroxymethyl)cyclopropyl)buta-1,3-diynyl)-2-oxopyridin-1(2H)-yl)-2-methyl-2-(methylsulfonyl)butanamide |
| 38 | 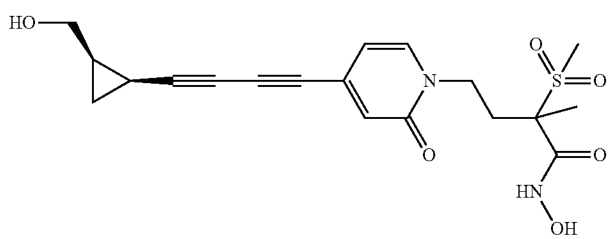 [SMILES: CC(CCn1ccc(C#CC#C[C@H]2C[C@H]2CO)cc1=O)(C(=O)NO)S(C)(=O)=O] | N-hydroxy-4-(4-(((1S,2R)-2-(hydroxymethyl)cyclopropyl)buta-1,3-diynyl)-2-oxopyridin-1(2H)-yl)-2-methyl-2-(methylsulfonyl)butanamide |
| 39 | 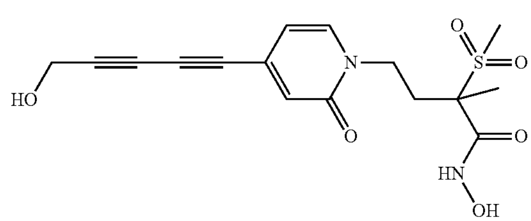 [SMILES: CC(CCn1ccc(C#CC#CCO)cc1=O)(C(=O)NO)S(C)(=O)=O] | N-hydroxy-4-(4-(5-hydroxypenta-1,3-diynyl)-2-oxopyridin-1(2H)-yl)-2-methyl-2-(methylsulfonyl)butanamide |
| 40 | 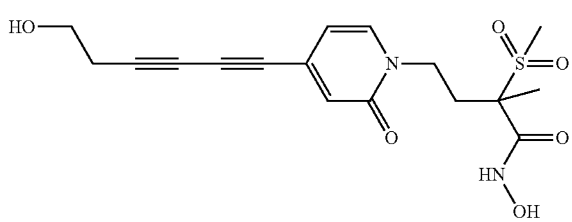 [SMILES: CC(CCn1ccc(C#CC#CCCO)cc1=O)(C(=O)NO)S(C)(=O)=O] | N-hydroxy-4-(4-(6-hydroxyhexa-1,3-diynyl)-2-oxopyridin-1(2H)-yl)-2-methyl-2-(methylsulfonyl)butanamide |
| 41 | 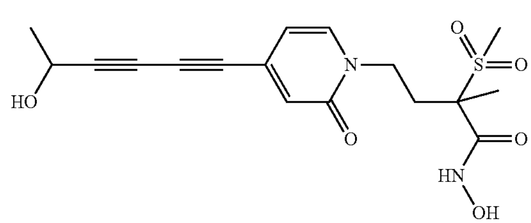 [SMILES: CC(O)C#CC#Cc1ccn(CCC(C)(C(=O)NO)S(C)(=O)=O)c(=O)c1] | N-hydroxy-4-(4-(5-hydroxyhexa-1,3-diynyl)-2-oxopyridin-1(2H)-yl)-2-methyl-2-(methylsulfonyl)butanamide |

TABLE 1-continued

| # | structure | name |
|---|---|---|
| 42 | 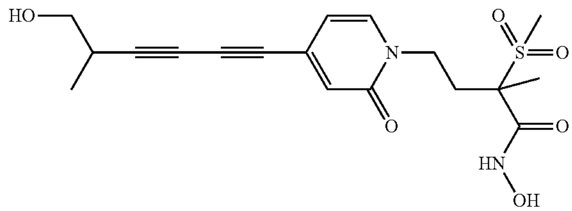 | N-hydroxy-4-(4-(6-hydroxy-5-methylhexa-1,3-diynyl)-2-oxopyridin-1(2H)-yl)-2-methyl-2-(methylsulfonyl)butanamide |
| 43 | 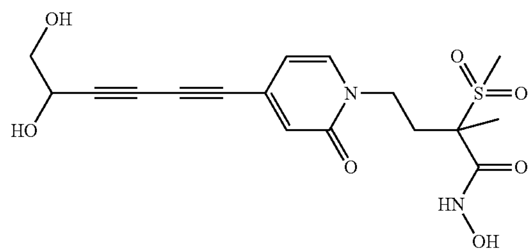 [SMILES: CC(CCn1ccc(C#CC#CC(O)CO)cc1=O)(C(=O)NO)S(C)(=O)=O] | 4-(4-(5,6-dihydroxyhexa-1,3-diynyl)-2-oxopyridin-1(2H)-yl)-N-hydroxy-2-methyl-2-(methylsulfonyl)butanamide |
| 44 | 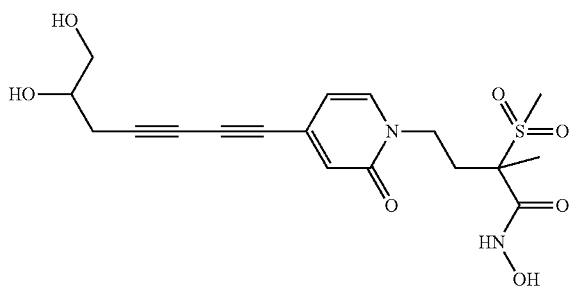 [SMILES: CC(CCn1ccc(C#CC#CCC(O)CO)cc1=O)(C(=O)NO)S(C)(=O)=O] | 4-(4-(6,7-dihydroxyhepta-1,3-diynyl)-2-oxopyridin-1(2H)-yl)-N-hydroxy-2-methyl-2-(methylsulfonyl)butanamide |
| 45 | 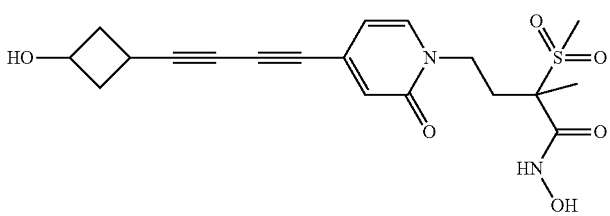 [SMILES: CC(CCn1ccc(C#CC#CC2CC(O)C2)cc1=O)(C(=O)NO)S(C)(=O)=O] | N-hydroxy-4-(4-((3-hydroxycyclobutyl)buta-1,3-diynyl)-2-oxopyridin-1(2H)-yl)-2-methyl-2-(methylsulfonyl)butanamide |
| 46 | 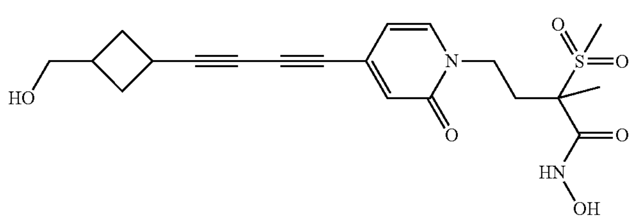 [SMILES: CC(CCn1ccc(C#CC#CC2CC(CO)C2)cc1=O)(C(=O)NO)S(C)(=O)=O] | N-hydroxy-4-(4-((3-(hydroxymethyl)cyclobutyl)buta-1,3-diynyl)-2-oxopyridin-1(2H)-yl)-2-methyl-2-(methylsulfonyl)butanamide |
| 47 | 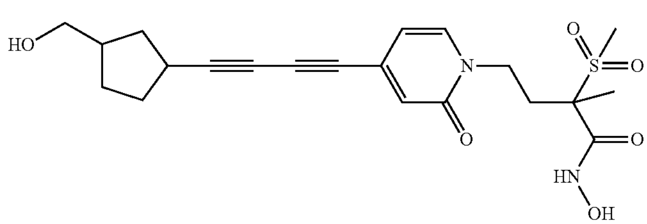 [SMILES: CC(CCn1ccc(C#CC#CC2CCC(CO)C2)cc1=O)(C(=O)NO)S(C)(=O)=O] | N-hydroxy-4-(4-((3-(hydroxymethyl)cyclopentyl)buta-1,3-diynyl)-2-oxopyridin-1(2H)-yl)-2-methyl-2-(methylsulfonyl)butanamide |

TABLE 1-continued

| # | structure | name |
|---|---|---|
| 48 | 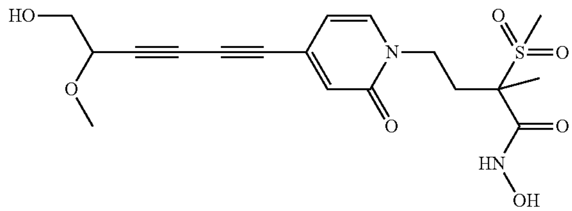 | N-hydroxy-4-(4-(6-hydroxy-5-methoxyhexa-1,3-diynyl)-2-oxopyridin-1(2H)-yl)-2-methyl-2-(methylsulfonyl)butanamide |
| 49 | 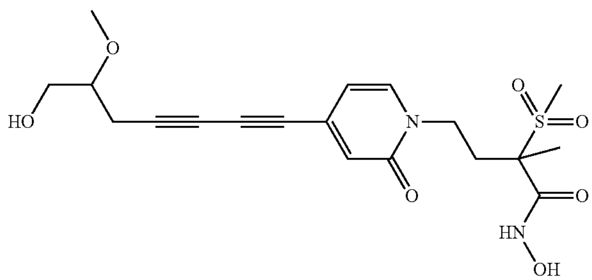 [SMILES: COC(CO)CC#CC#Cc1ccn(CCC(C)(C(=O)NO)S(C)(=O)=O)c(=O)c1] | N-hydroxy-4-(4-(7-hydroxy-6-methoxyhepta-1,3-diynyl)-2-oxopyridin-1(2H)-yl)-2-methyl-2-(methylsulfonyl)butanamide |
| 50 | 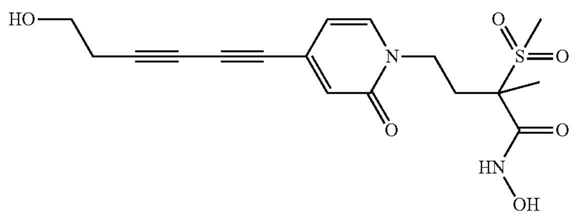 [SMILES: CC(CCn1ccc(C#CC#CCCO)cc1=O)(C(=O)NO)S(C)(=O)=O] | N-hydroxy-4-(4-(6-hydroxyhexa-1,3-diynyl)-2-oxopyridin-1(2H)-yl)-2-methyl-2-(methylsulfonyl)butanamide |
| 51 | 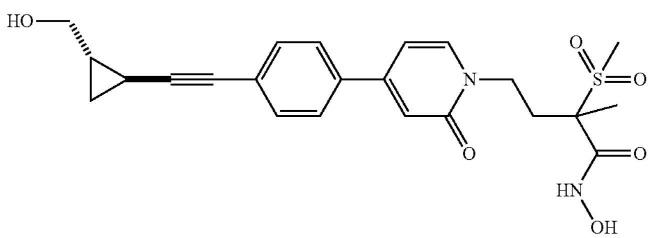 [SMILES: CC(CCn1ccc(-c2ccc(C#C[C@H]3C[C@@H]3CO)cc2)cc1=O)(C(=O)NO)S(C)(=O)=O] | N-hydroxy-4-(4-(4-(((1S,2S)-2-(hydroxymethyl)cyclopropyl)ethynyl)phenyl)-2-oxopyridin-1(2H)-yl)-2-methyl-2-(methylsulfonyl)butanamide |
| 52 | 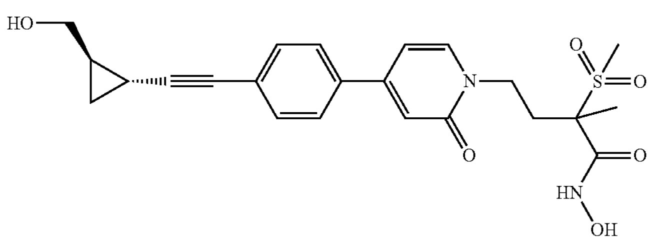 [SMILES: CC(CCn1ccc(-c2ccc(C#C[C@@H]3C[C@H]3CO)cc2)cc1=O)(C(=O)NO)S(C)(=O)=O] | N-hydroxy-4-(4-(4-(((1R,2R)-2-(hydroxymethyl)cyclopropyl)ethynyl)phenyl)-2-oxopyridin-1(2H)-yl)-2-methyl-2-(methylsulfonyl)butanamide |
| 53 | 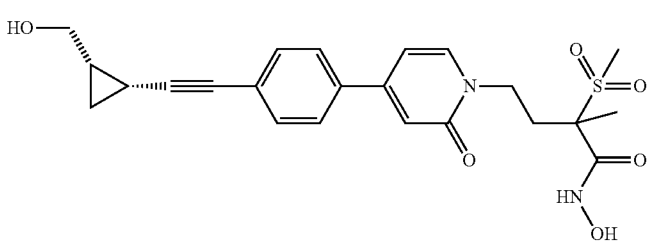 [SMILES: CC(CCn1ccc(-c2ccc(C#C[C@@H]3C[C@@H]3CO)cc2)cc1=O)(C(=O)NO)S(C)(=O)=O] | N-hydroxy-4-(4-(4-(((1R,2S)-2-(hydroxymethyl)cyclopropyl)ethynyl)phenyl)-2-oxopyridin-1(2H)-yl)-2-methyl-2-(methylsulfonyl)butanamide |

TABLE 1-continued

| # | structure | name |
|---|---|---|
| 54 | 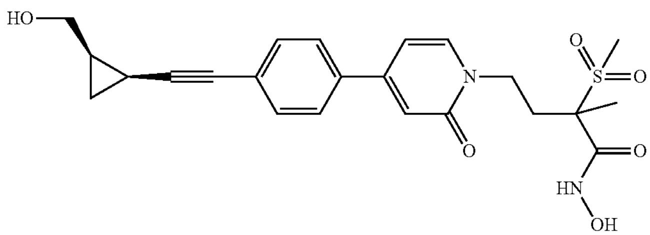 [SMILES: CC(CCn1ccc(-c2ccc(C#C[C@H]3C[C@H]3CO)cc2)cc1=O)(C(=O)NO)S(C)(=O)=O] | N-hydroxy-4-(4-(4-(((1S,2R)-2-(hydroxymethyl)cyclopropyl)ethynyl)phenyl)-2-oxopyridin-1(2H)-yl)-2-methyl-2-(methylsulfonyl)butanamide |
| 55 | 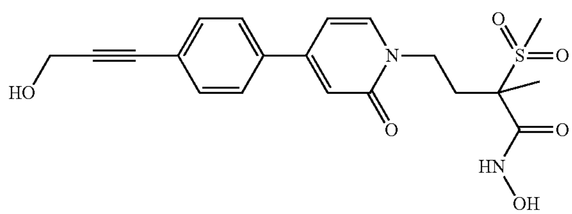 [SMILES: CC(CCn1ccc(-c2ccc(C#CCO)cc2)cc1=O)(C(=O)NO)S(C)(=O)=O] | N-hydroxy-4-(4-(4-(3-hydroxyprop-1-ynyl)phenyl)-2-oxopyridin-1(2H)-yl)-2-methyl-2-(methylsulfonyl)butanamide |
| 56 | 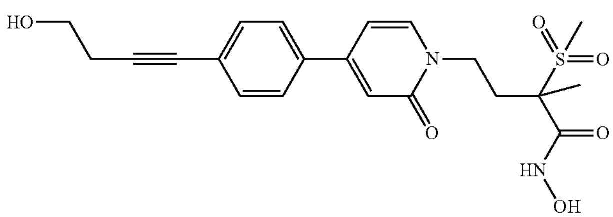 | N-hydroxy-4-(4-(4-(4-hydroxybut-1-ynyl)phenyl)-2-oxopyridin-1(2H)-yl)-2-methyl-2-(methylsulfonyl)butanamide |
| 57 | 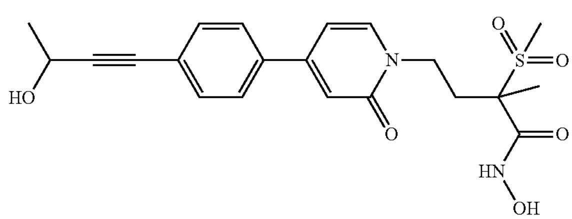 [SMILES: CC(O)C#Cc1ccc(-c2ccn(CCC(C)(C(=O)NO)S(C)(=O)=O)c(=O)c2)cc1] | N-hydroxy-4-(4-(4-(3-hydroxybut-1-ynyl)phenyl)-2-oxopyridin-1(2H)-yl)-2-methyl-2-(methylsulfonyl)butanamide |
| 58 | 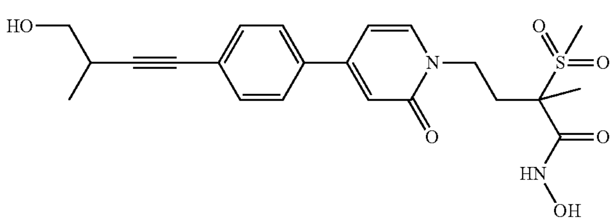 [SMILES: CC(C#Cc1ccc(-c2ccn(CCC(C)(C(=O)NO)S(C)(=O)=O)c(=O)c2)cc1)CO] | N-hydroxy-4-(4-(4-(4-hydroxy-3-methylbut-1-ynyl)phenyl)-2-oxopyridin-1(2H)-yl)-2-methyl-2-(methylsulfonyl)butanamide |
| 59 | 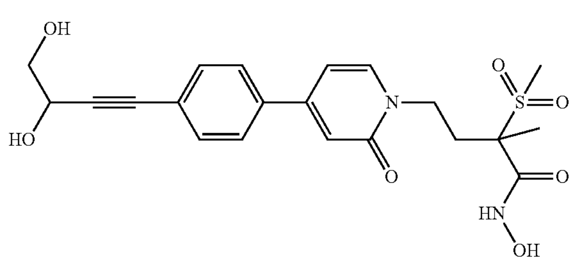 [SMILES: CC(CCn1ccc(-c2ccc(C#CC(O)CO)cc2)cc1=O)(C(=O)NO)S(C)(=O)=O] | 4-(4-(4-(3,4-dihydroxybut-1-ynyl)phenyl)-2-oxopyridin-1(2H)-yl)-N-hydroxy-2-methyl-2-(methylsulfonyl)butanamide |

TABLE 1-continued

| # | structure | name |
|---|---|---|
| 60 | 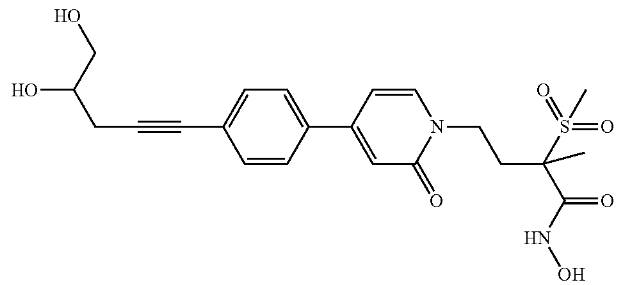 [SMILES: CC(CCn1ccc(-c2ccc(C#CCC(O)CO)cc2)cc1=O)(C(=O)NO)S(C)(=O)=O] | 4-(4-(4-(4,5-dihydroxypent-1-ynyl)phenyl)-2-oxopyridin-1(2H)-yl)-N-hydroxy-2-methyl-2-(methylsulfonyl)butanamide |
| 61 | 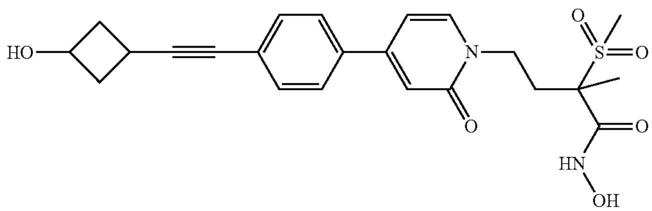 [SMILES: CC(CCn1ccc(-c2ccc(C#CC3CC(O)C3)cc2)cc1=O)(C(=O)NO)S(C)(=O)=O] | N-hydroxy-4-(4-(4-((3-hydroxycyclobutyl)ethynyl)phenyl)-2-oxopyridin-1(2H)-yl)-2-methyl-2-(methylsulfonyl)butanamide |
| 62 | 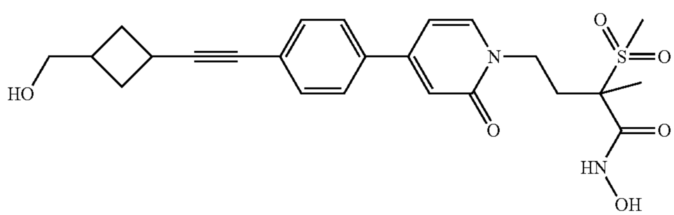 [SMILES: CC(CCn1ccc(-c2ccc(C#CC3CC(CO)C3)cc2)cc1=O)(C(=O)NO)S(C)(=O)=O] | N-hydroxy-4-(4-(4-((3-(hydroxymethyl)cyclobutyl)ethynyl)phenyl)-2-oxopyridin-1(2H)-yl)-2-methyl-2-(methylsulfonyl)butanamide |
| 63 | 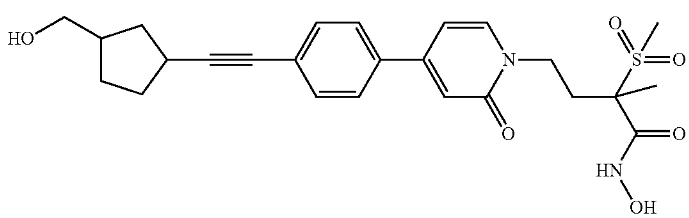 [SMILES: CC(CCn1ccc(-c2ccc(C#CC3CCC(CO)C3)cc2)cc1=O)(C(=O)NO)S(C)(=O)=O] | N-hydroxy-4-(4-(4-((3-(hydroxymethyl)cyclopentyl)ethynyl)phenyl)-2-oxopyridin-1(2H)-yl)-2-methyl-2-(methylsulfonyl)butanamide |
| 64 | 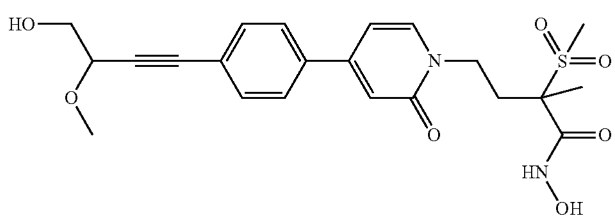 [SMILES: COC(C#Cc1ccc(-c2ccn(CCC(C)(C(=O)NO)S(C)(=O)=O)c(=O)c2)cc1)CO] | N-hydroxy-4-(4-(4-(4-hydroxy-3-methoxybut-1-ynyl)phenyl)-2-oxopyridin-1(2H)-yl)-2-methyl-2-(methylsulfonyl)butanamide |
| 65 | 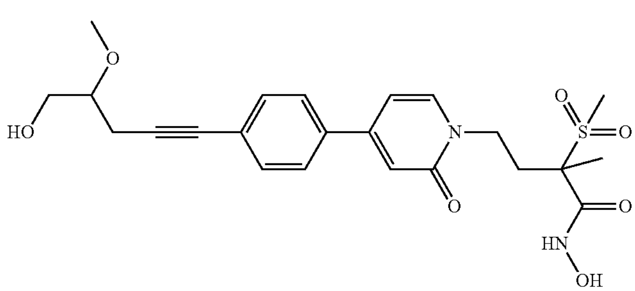 [SMILES: COC(CO)CC#Cc1ccc(-c2ccn(CCC(C)(C(=O)NO)S(C)(=O)=O)c(=O)c2)cc1] | N-hydroxy-4-(4-(4-(5-hydroxy-4-methoxypent-1-ynyl)phenyl)-2-oxopyridin-1(2H)-yl)-2-methyl-2-(methylsulfonyl)butanamide |

TABLE 1-continued

| # | structure | name |
|---|---|---|
| 66 | 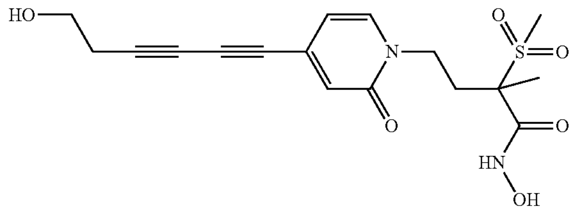 [SMILES: CC(CCn1ccc(C#CC#CCCO)cc1=O)(C(=O)NO)S(C)(=O)=O] | N-hydroxy-4-(4-(6-hydroxyhexa-1,3-diynyl)-2-oxopyridin-1(2H)-yl)-2-methyl-2-(methylsulfonyl)butanamide |
| 67 | 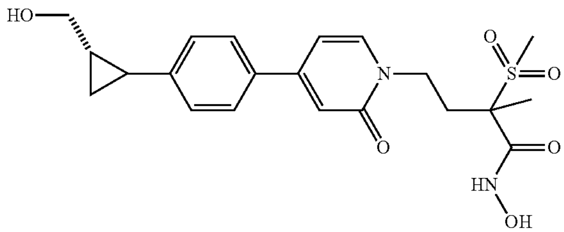 [SMILES: CC(CCn1ccc(-c2ccc(C3C[C@@H]3CO)cc2)cc1=O)(C(=O)NO)S(C)(=O)=O] | N-hydroxy-4-(4-(4-((2S)-2-(hydroxymethyl)cyclopropyl)phenyl)-2-oxopyridin-1(2H)-yl)-2-methyl-2-(methylsulfonyl)butanamide |
| 68 | 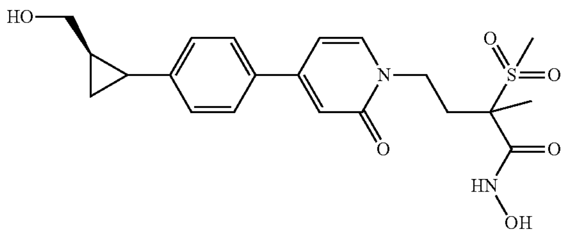 [SMILES: CC(CCn1ccc(-c2ccc(C3C[C@H]3CO)cc2)cc1=O)(C(=O)NO)S(C)(=O)=O] | N-hydroxy-4-(4-(4-((2R)-2-(hydroxymethyl)cyclopropyl)phenyl)-2-oxopyridin-1(2H)-yl)-2-methyl-2-(methylsulfonyl)butanamide |
| 69 | 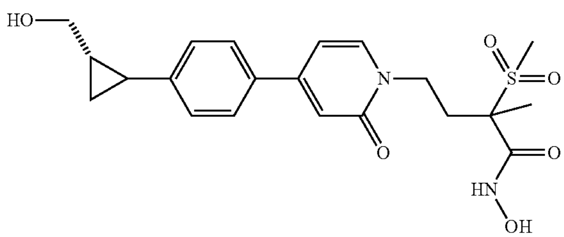 [SMILES: CC(CCn1ccc(-c2ccc(C3C[C@@H]3CO)cc2)cc1=O)(C(=O)NO)S(C)(=O)=O] | N-hydroxy-4-(4-(4-((2S)-2-(hydroxymethyl)cyclopropyl)phenyl)-2-oxopyridin-1(2H)-yl)-2-methyl-2-(methylsulfonyl)butanamide |
| 70 | 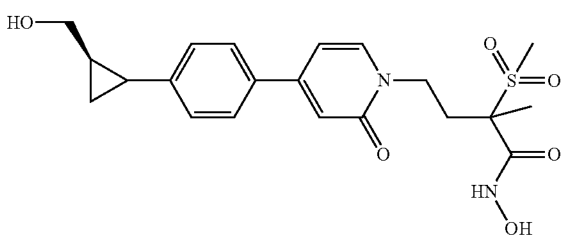 [SMILES: CC(CCn1ccc(-c2ccc(C3C[C@H]3CO)cc2)cc1=O)(C(=O)NO)S(C)(=O)=O] | N-hydroxy-4-(4-(4-((2R)-2-(hydroxymethyl)cyclopropyl)phenyl)-2-oxopyridin-1(2H)-yl)-2-methyl-2-(methylsulfonyl)butanamide |
| 71 | 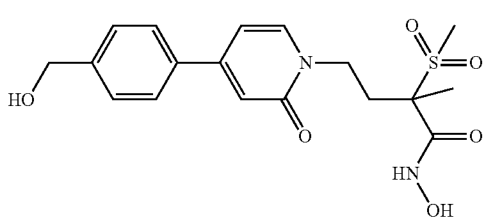 [SMILES: CC(CCn1ccc(-c2ccc(CO)cc2)cc1=O)(C(=O)NO)S(C)(=O)=O] | N-hydroxy-4-(4-(4-(hydroxymethyl)phenyl)-2-oxopyridin-1(2H)-yl)-2-methyl-2-(methylsulfonyl)butanamide |
| 72 | 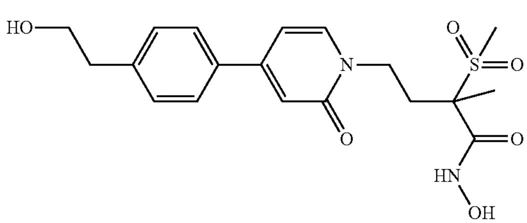 [SMILES: CC(CCn1ccc(-c2ccc(CCO)cc2)cc1=O)(C(=O)NO)S(C)(=O)=O] | N-hydroxy-4-(4-(4-(2-hydroxyethyl)phenyl)-2-oxopyridin-1(2H)-yl)-2-methyl-2-(methylsulfonyl)butanamide |

TABLE 1-continued

| # | structure | name |
|---|---|---|
| 73 | 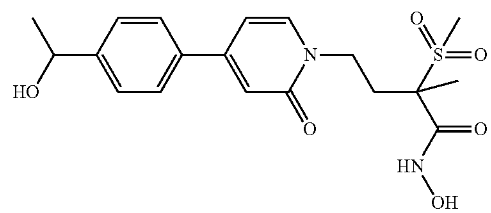 [SMILES: CC(O)c1ccc(-c2ccn(CCC(C)(C(=O)NO)S(C)(=O)=O)c(=O)c2)cc1] | N-hydroxy-4-(4-(4-(1-hydroxyethyl)phenyl)-2-oxopyridin-1(2H)-yl)-2-methyl-2-(methylsulfonyl)butanamide |
| 74 | 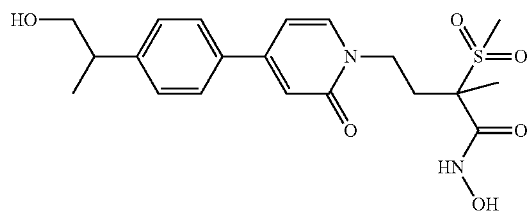 | N-hydroxy-4-(4-(4-(1-hydroxypropan-2-yl)phenyl)-2-oxopyridin-1(2H)-yl)-2-methyl-2-(methylsulfonyl)butanamide |
| 75 | 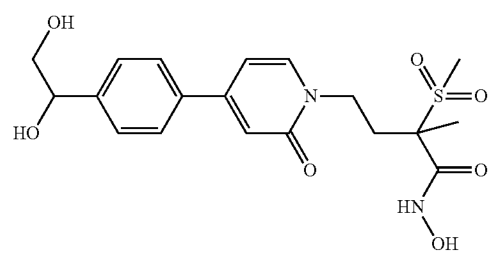 [SMILES: CC(CCn1ccc(-c2ccc(C(O)CO)cc2)cc1=O)(C(=O)NO)S(C)(=O)=O] | 4-(4-(4-(1,2-dihydroxyethyl)phenyl)-2-oxopyridin-1(2H)-yl)-N-hydroxy-2-methyl-2-(methylsulfonyl)butanamide |
| 76 | 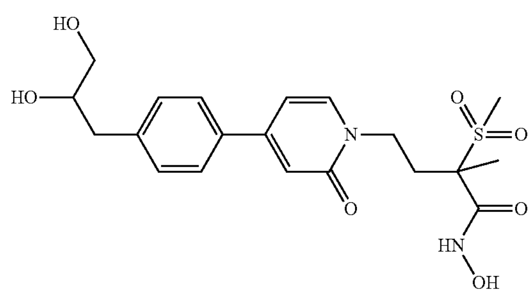 [SMILES: CC(CCn1ccc(-c2ccc(CC(O)CO)cc2)cc1=O)(C(=O)NO)S(C)(=O)=O] | 4-(4-(4-(2,3-dihydroxypropyl)phenyl)-2-oxopyridin-1(2H)-yl)-N-hydroxy-2-methyl-2-(methylsulfonyl)butanamide |
| 77 | 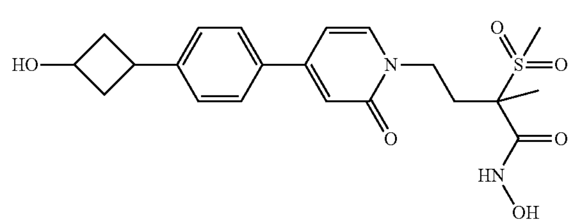 [SMILES: CC(CCn1ccc(-c2ccc(C3CC(O)C3)cc2)cc1=O)(C(=O)NO)S(C)(=O)=O] | N-hydroxy-4-(4-(4-(3-hydroxycyclobutyl)phenyl)-2-oxopyridin-1(2H)-yl)-2-methyl-2-(methylsulfonyl)butanamide |
| 78 | 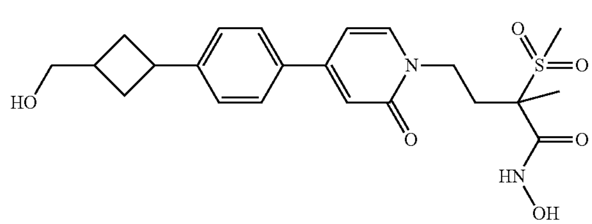 [SMILES: CC(CCn1ccc(-c2ccc(C3CC(CO)C3)cc2)cc1=O)(C(=O)NO)S(C)(=O)=O] | N-hydroxy-4-(4-(4-(3-(hydroxymethyl)cyclobutyl)phenyl)-2-oxopyridin-1(2H)-yl)-2-methyl-2-(methylsulfonyl)butanamide |

TABLE 1-continued

| # | structure | name |
|---|---|---|
| 79 | 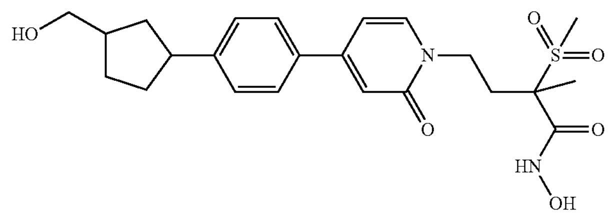 [SMILES: CC(CCn1ccc(-c2ccc(C3CCC(CO)C3)cc2)cc1=O)(C(=O)NO)S(C)(=O)=O] | N-hydroxy-4-(4-(4-(3-(hydroxymethyl)cyclopentyl)phenyl)-2-oxopyridin-1(2H)-yl)-2-methyl-2-(methylsulfonyl)butanamide |
| 80 | 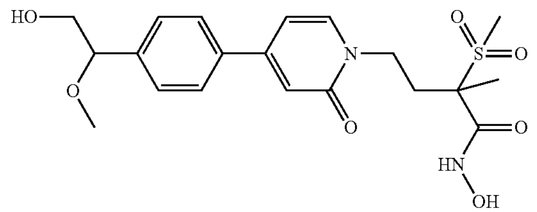 [SMILES: COC(CO)c1ccc(-c2ccn(CCC(C)(C(=O)NO)S(C)(=O)=O)c(=O)c2)cc1] | N-hydroxy-4-(4-(4-(2-hydroxy-1-methoxyethyl)phenyl)-2-oxopyridin-1(2H)-yl)-2-methyl-2-(methylsulfonyl)butanamide |
| 81 | 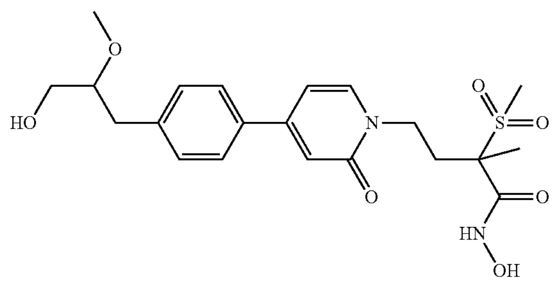 [SMILES: COC(CO)Cc1ccc(-c2ccn(CCC(C)(C(=O)NO)S(C)(=O)=O)c(=O)c2)cc1] | N-hydroxy-4-(4-(4-(3-hydroxy-2-methoxypropyl)phenyl)-2-oxopyridin-1(2H)-yl)-2-methyl-2-(methylsulfonyl)butanamide |
| 82 | 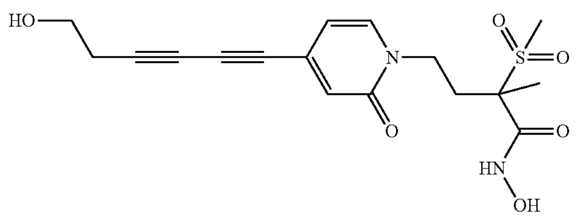 [SMILES: CC(CCn1ccc(C#CC#CCCO)cc1=O)(C(=O)NO)S(C)(=O)=O] | N-hydroxy-4-(4-(6-hydroxyhexa-1,3-diynyl)-2-oxopyridin-1(2H)-yl)-2-methyl-2-(methylsulfonyl)butanamide |
| 83 | 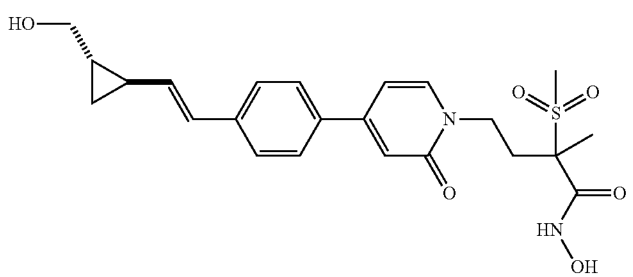 | N-hydroxy-4-(4-(4-((E)-2-((1R,2S)-2-(hydroxymethyl)cyclopropyl)vinyl)phenyl)-2-oxopyridin-1(2H)-yl)-2-methyl-2-(methylsulfonyl)butanamide |
| 84 | 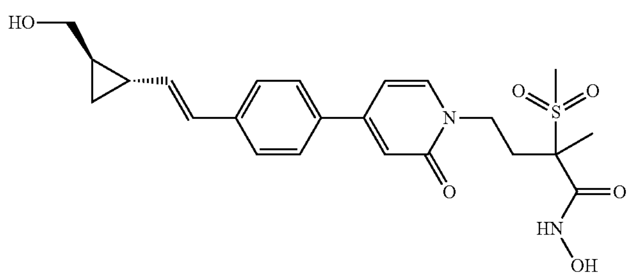 [SMILES: CC(CCn1ccc(-c2ccc(/C=C/[C@@H]3C[C@H]3CO)cc2)cc1=O)(C(=O)NO)S(C)(=O)=O] | N-hydroxy-4-(4-(4-((E)-2-((1S,2R)-2-(hydroxymethyl)cyclopropyl)vinyl)phenyl)-2-oxopyridin-1(2H)-yl)-2-methyl-2-(methylsulfonyl)butanamide |

TABLE 1-continued

| # | structure | name |
|---|---|---|
| 85 | 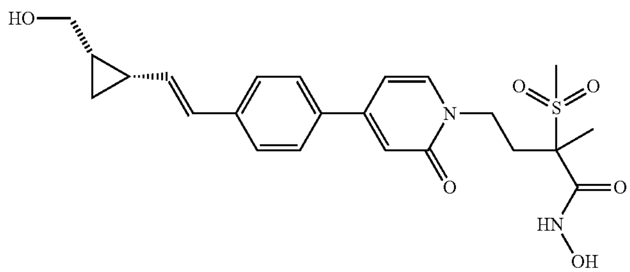 [SMILES: CC(CCn1ccc(-c2ccc(/C=C/[C@@H]3C[C@@H]3CO)cc2)cc1=O)(C(=O)NO)S(C)(=O)=O] | N-hydroxy-4-(4-(4-((E)-2-((1S,2S)-2-(hydroxymethyl)cyclopropyl)vinyl)phenyl)-2-oxopyridin-1(2H)-yl)-2-methyl-2-(methylsulfonyl)butanamide |
| 86 | 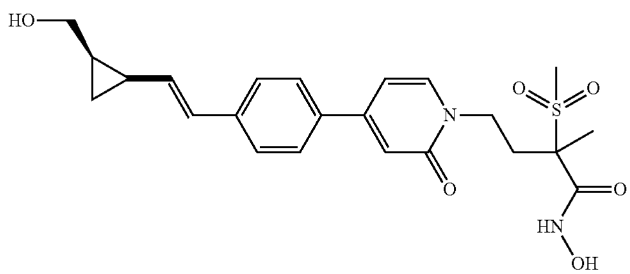 | N-hydroxy-4-(4-(4-((E)-2-((1R,2R)-2-(hydroxymethyl)cyclopropyl)vinyl)phenyl)-2-oxopyridin-1(2H)-yl)-2-methyl-2-(methylsulfonyl)butanamide |
| 87 | 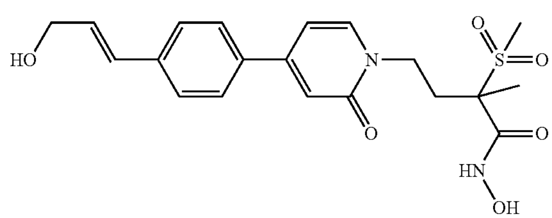 [SMILES: CC(CCn1ccc(-c2ccc(/C=C/CO)cc2)cc1=O)(C(=O)NO)S(C)(=O)=O] | (E)-N-hydroxy-4-(4-(4-(3-hydroxyprop-1-enyl)phenyl)-2-oxopyridin-1(2H)-yl)-2-methyl-2-(methylsulfonyl)butanamide |
| 88 | 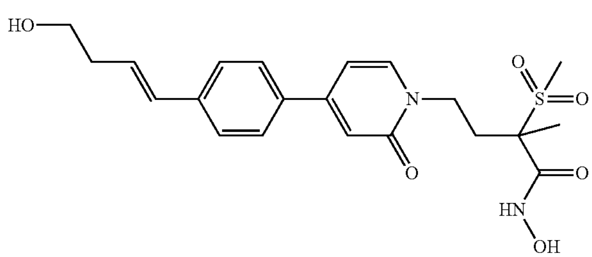 [SMILES: CC(CCn1ccc(-c2ccc(/C=C/CCO)cc2)cc1=O)(C(=O)NO)S(C)(=O)=O] | (E)-N-hydroxy-4-(4-(4-(4-hydroxybut-1-enyl)phenyl)-2-oxopyridin-1(2H)-yl)-2-methyl-2-(methylsulfonyl)butanamide |
| 89 | 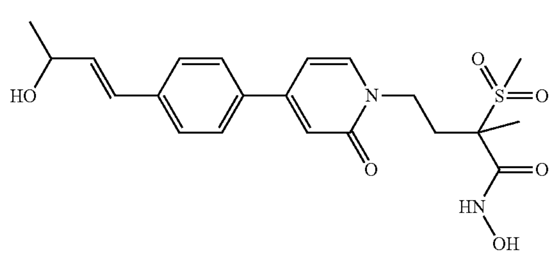 [SMILES: CC(O)/C=C/c1ccc(-c2ccn(CCC(C)(C(=O)NO)S(C)(=O)=O)c(=O)c2)cc1] | (E)-N-hydroxy-4-(4-(4-(3-hydroxybut-1-enyl)phenyl)-2-oxopyridin-1(2H)-yl)-2-methyl-2-(methylsulfonyl)butanamide |
| 90 | 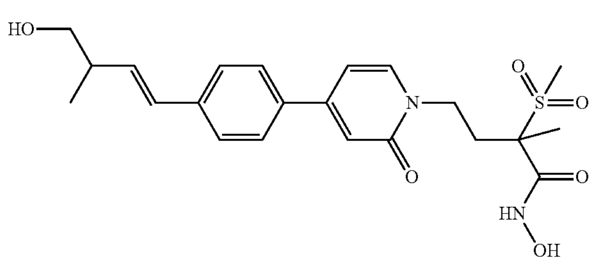 | (E)-N-hydroxy-4-(4-(4-(4-hydroxy-3-methylbut-1-enyl)phenyl)-2-oxopyridin-1(2H)-yl)-2-methyl-2-(methylsulfonyl)butanamide |

TABLE 1-continued

| # | structure | name |
|---|---|---|
| 91 | 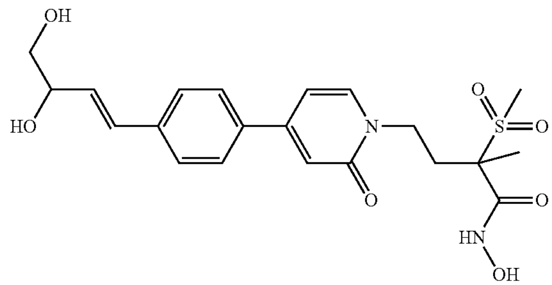 [SMILES: CC(CCn1ccc(-c2ccc(/C=C/C(O)CO)cc2)cc1=O)(C(=O)NO)S(C)(=O)=O] | (E)-4-(4-(4-(3,4-dihydroxybut-1-enyl)phenyl)-2-oxopyridin-1(2H)-yl)-N-hydroxy-2-methyl-2-(methylsulfonyl)butanamide |
| 92 | 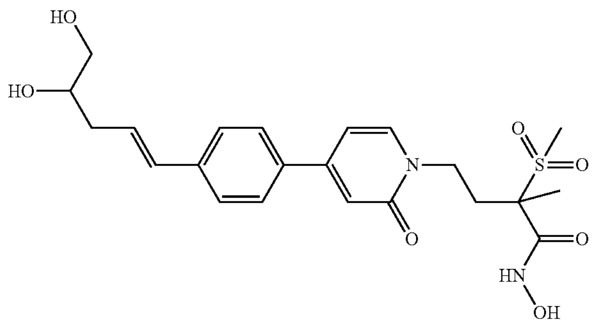 [SMILES: CC(CCn1ccc(-c2ccc(/C=C/CC(O)CO)cc2)cc1=O)(C(=O)NO)S(C)(=O)=O] | (E)-4-(4-(4-(4,5-dihydroxypent-1-enyl)phenyl)-2-oxopyridin-1(2H)-yl)-N-hydroxy-2-methyl-2-(methylsulfonyl)butanamide |
| 93 | 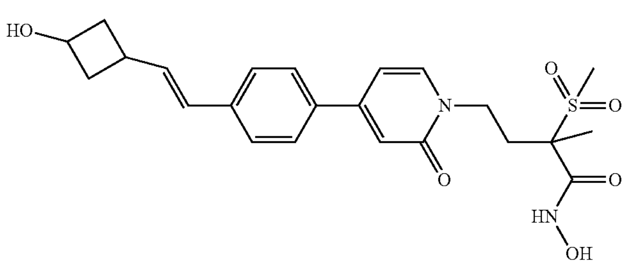 [SMILES: CC(CCn1ccc(-c2ccc(/C=C/C3CC(O)C3)cc2)cc1=O)(C(=O)NO)S(C)(=O)=O] | (E)-N-hydroxy-4-(4-(4-(2-(3-hydroxycyclobutyl)vinyl)phenyl)-2-oxopyridin-1(2H)-yl)-2-methyl-2-(methylsulfonyl)butanamide |
| 94 | 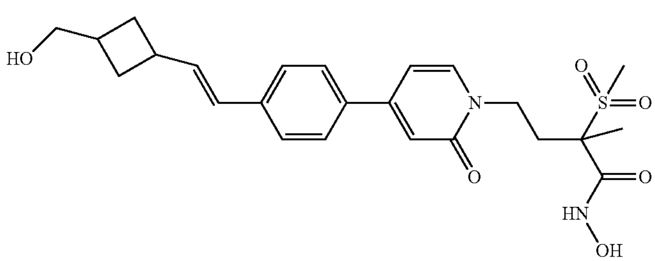 [SMILES: CC(CCn1ccc(-c2ccc(/C=C/C3CC(CO)C3)cc2)cc1=O)(C(=O)NO)S(C)(=O)=O] | (E)-N-hydroxy-4-(4-(4-(2-(3-(hydroxymethyl)cyclobutyl)vinyl)phenyl)-2-oxopyridin-1(2H)-yl)-2-methyl-2-(methylsulfonyl)butanamide |
| 95 | 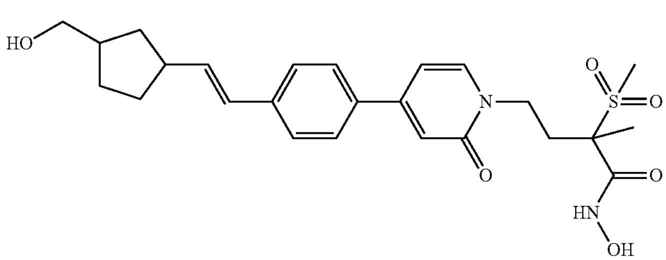 [SMILES: CC(CCn1ccc(-c2ccc(/C=C/C3CCC(CO)C3)cc2)cc1=O)(C(=O)NO)S(C)(=O)=O] | (E)-N-hydroxy-4-(4-(4-(2-(3-(hydroxymethyl)cyclopentyl)vinyl)phenyl)-2-oxopyridin-1(2H)-yl)-2-methyl-2-(methylsulfonyl)butanamide |

TABLE 1-continued

| # | structure | name |
|---|---|---|
| 96 | 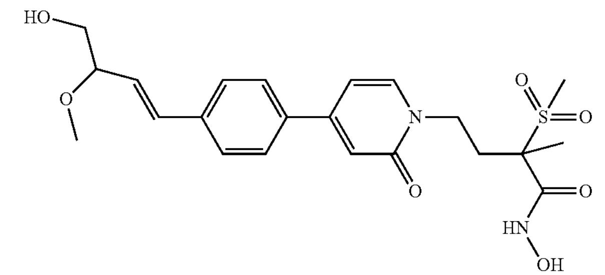 [SMILES: COC(/C=C/c1ccc(-c2ccn(CCC(C)(C(=O)NO)S(C)(=O)=O)c(=O)c2)cc1)CO] | (E)-N-hydroxy-4-(4-(4-(4-hydroxy-3-methoxybut-1-enyl)phenyl)-2-oxopyridin-1(2H)-yl)-2-methyl-2-(methylsulfonyl)butanamide |
| 97 | 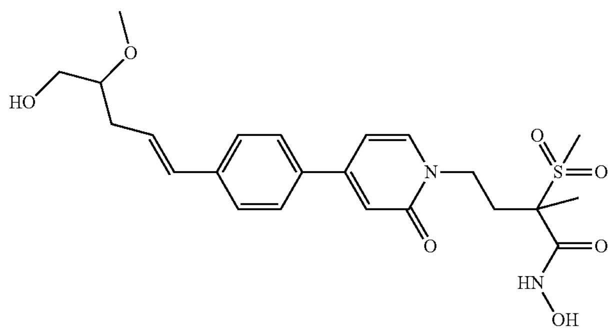 [SMILES: COC(CO)C/C=C/c1ccc(-c2ccn(CCC(C)(C(=O)NO)S(C)(=O)=O)c(=O)c2)cc1] | (E)-N-hydroxy-4-(4-(4-(5-hydroxy-4-methoxypent-1-enyl)phenyl)-2-oxopyridin-1(2H)-yl)-2-methyl-2-(methylsulfonyl)butanamide |
| 98 | 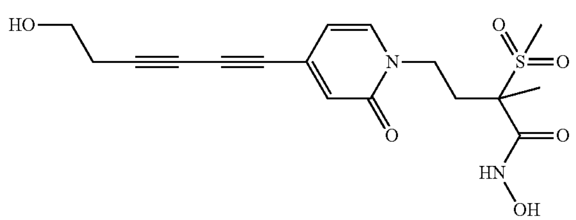 | N-hydroxy-4-(4-(6-hydroxyhexa-1,3-diynyl)-2-oxopyridin-1(2H)-yl)-2-methyl-2-(methylsulfonyl)butanamide |
| 99 | 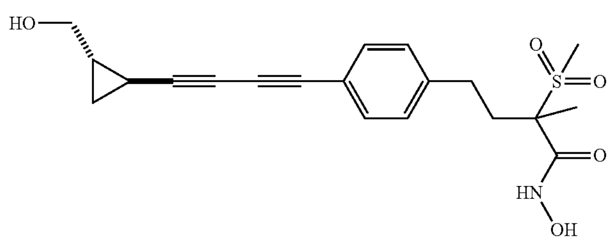 | N-hydroxy-4-(4-(((1S,2S)-2-(hydroxymethyl)cyclopropyl)buta-1,3-diynyl)phenyl)-2-methyl-2-(methylsulfonyl)butanamide |
| 100 | 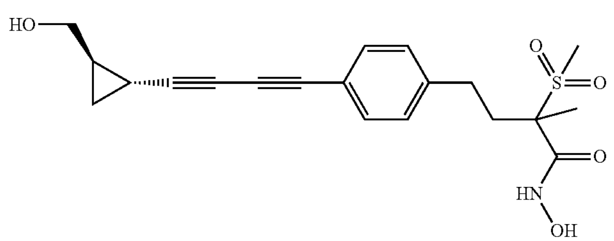 [SMILES: CC(CCc1ccc(C#CC#C[C@@H]2C[C@H]2CO)cc1)(C(=O)NO)S(C)(=O)=O] | N-hydroxy-4-(4-(((1R,2R)-2-(hydroxymethyl)cyclopropyl)buta-1,3-diynyl)phenyl)-2-methyl-2-(methylsulfonyl)butanamide |
| 101 | 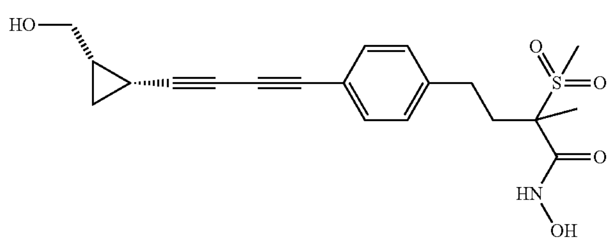 [SMILES: CC(CCc1ccc(C#CC#C[C@@H]2C[C@@H]2CO)cc1)(C(=O)NO)S(C)(=O)=O] | N-hydroxy-4-(4-(((1R,2S)-2-(hydroxymethyl)cyclopropyl)buta-1,3-diynyl)phenyl)-2-methyl-2-(methylsulfonyl)butanamide |

TABLE 1-continued

| # | structure | name |
|---|---|---|
| 102 | 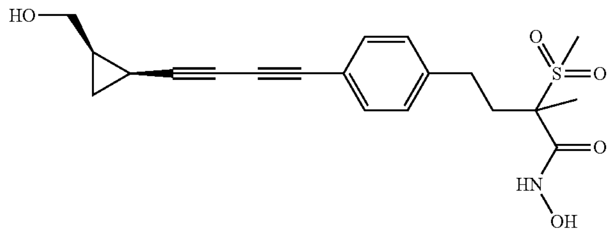 [SMILES: CC(CCc1ccc(C#CC#C[C@H]2C[C@H]2CO)cc1)(C(=O)NO)S(C)(=O)=O] | N-hydroxy-4-(4-(((1S,2R)-2-(hydroxymethyl)cyclopropyl)buta-1,3-diynyl)phenyl)-2-methyl-2-(methylsulfonyl)butanamide |
| 103 | 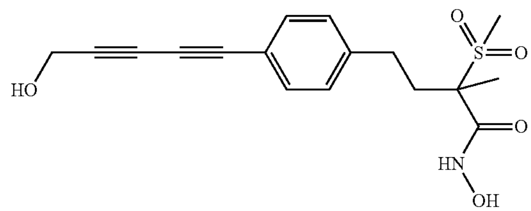 | N-hydroxy-4-(4-(5-hydroxypenta-1,3-diynyl)phenyl)-2-methyl-2-(methylsulfonyl)butanamide |
| 104 | 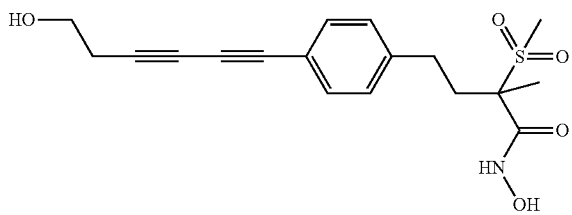 [SMILES: CC(CCc1ccc(C#CC#CCCO)cc1)(C(=O)NO)S(C)(=O)=O] | N-hydroxy-4-(4-(6-hydroxyhexa-1,3-diynyl)phenyl)-2-methyl-2-(methylsulfonyl)butanamide |
| 105 | 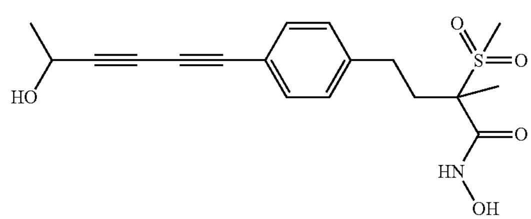 [SMILES: CC(O)C#CC#Cc1ccc(CCC(C)(C(=O)NO)S(C)(=O)=O)cc1] | N-hydroxy-4-(4-(5-hydroxyhexa-1,3-diynyl)phenyl)-2-methyl-2-(methylsulfonyl)butanamide |
| 106 | 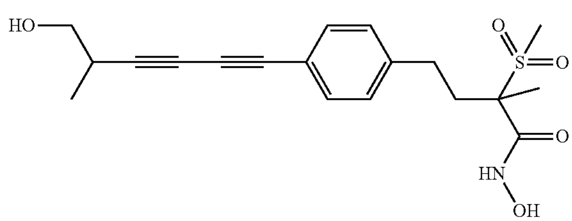 [SMILES: CC(C#CC#Cc1ccc(CCC(C)(C(=O)NO)S(C)(=O)=O)cc1)CO] | N-hydroxy-4-(4-(6-hydroxy-5-methylhexa-1,3-diynyl)phenyl)-2-methyl-2-(methylsulfonyl)butanamide |
| 107 | 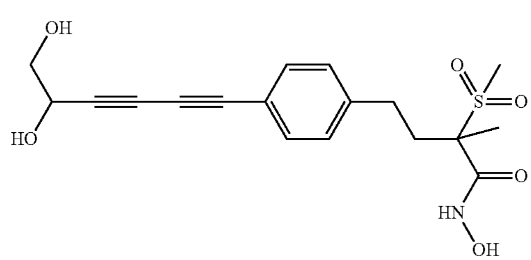 [SMILES: CC(CCc1ccc(C#CC#CC(O)CO)cc1)(C(=O)NO)S(C)(=O)=O] | 4-(4-(5,6-dihydroxyhexa-1,3-diynyl)phenyl)-N-hydroxy-2-methyl-2-(methylsulfonyl)butanamide |

TABLE 1-continued

| # | structure | name |
|---|---|---|
| 108 | 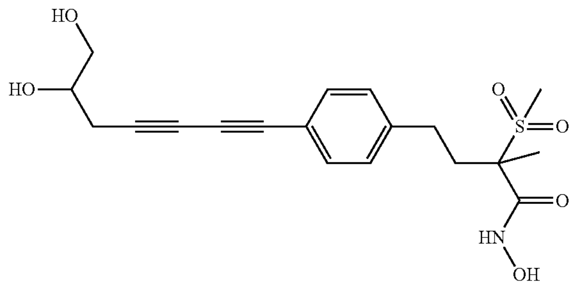 [SMILES: CC(CCc1ccc(C#CC#CCC(O)CO)cc1)(C(=O)NO)S(C)(=O)=O] | 4-(4-(6,7-dihydroxyhepta-1,3-diynyl)phenyl)-N-hydroxy-2-methyl-2-(methylsulfonyl)butanamide |
| 109 | 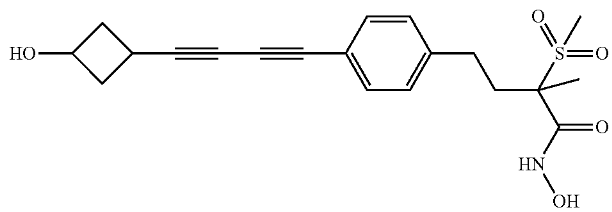 | N-hydroxy-4-(4-((3-hydroxycyclobutyl)buta-1,3-diynyl)phenyl)-2-methyl-2-(methylsulfonyl)butanamide |
| 110 | 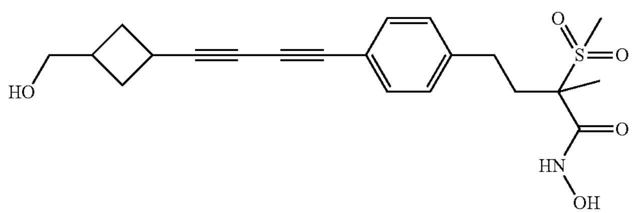 [SMILES: CC(CCc1ccc(C#CC#CC2CC(CO)C2)cc1)(C(=O)NO)S(C)(=O)=O] | N-hydroxy-4-(4-((3-(hydroxymethyl)cyclobutyl)buta-1,3-diynyl)phenyl)-2-methyl-2-(methylsulfonyl)butanamide |
| 111 | 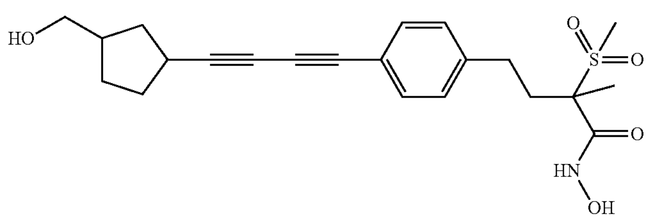 [SMILES: CC(CCc1ccc(C#CC#CC2CCC(CO)C2)cc1)(C(=O)NO)S(C)(=O)=O] | N-hydroxy-4-(4-((3-(hydroxymethyl)cyclopentyl)buta-1,3-diynyl)phenyl)-2-methyl-2-(methylsulfonyl)butanamide |
| 112 | 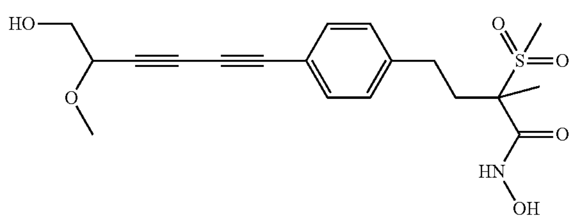 [SMILES: COC(C#CC#Cc1ccc(CCC(C)(C(=O)NO)S(C)(=O)=O)cc1)CO] | N-hydroxy-4-(4-(6-hydroxy-5-methoxyhexa-1,3-diynyl)phenyl)-2-methyl-2-(methylsulfonyl)butanamide |
| 113 | 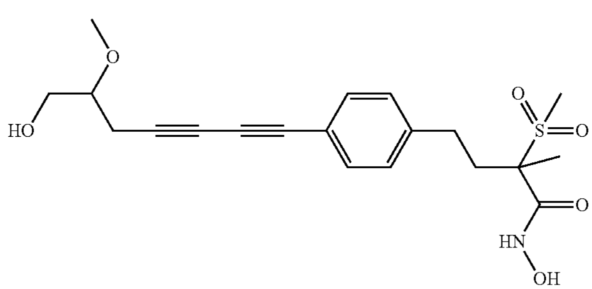 [SMILES: COC(CO)CC#CC#Cc1ccc(CCC(C)(C(=O)NO)S(C)(=O)=O)cc1] | N-hydroxy-4-(4-(7-hydroxy-6-methoxyhepta-1,3-diynyl)phenyl)-2-methyl-2-(methylsulfonyl)butanamide |

TABLE 1-continued

| # | structure | name |
|---|---|---|
| 114 | 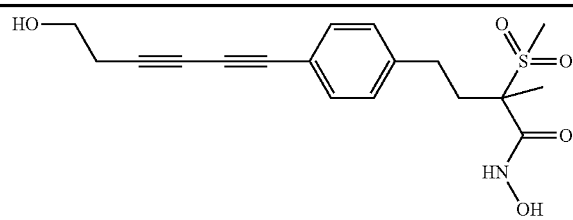 | N-hydroxy-4-(4-(6-hydroxyhexa-1,3-diynyl)phenyl)-2-methyl-2-(methylsulfonyl)butanamide |
| 115 | 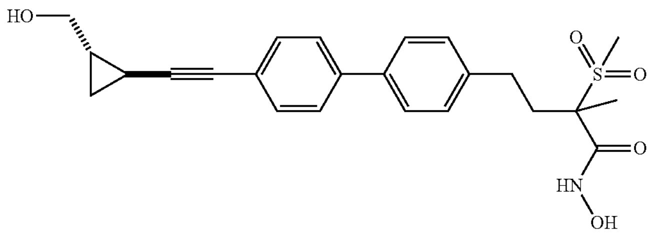 | N-hydroxy-4-(4'-(((1S,2S)-2-(hydroxymethyl)cyclopropyl)ethynyl)biphenyl-4-yl)-2-methyl-2-(methylsulfonyl)butanamide |
| 116 | 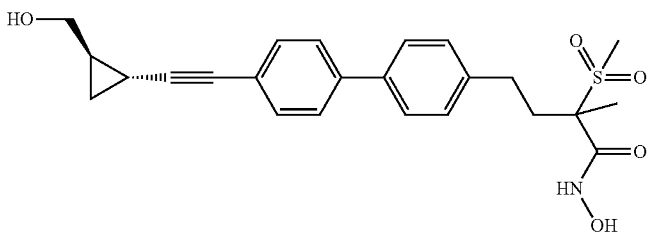 [SMILES: CC(CCc1ccc(-c2ccc(C#C[C@@H]3C[C@H]3CO)cc2)cc1)(C(=O)NO)S(C)(=O)=O] | N-hydroxy-4-(4'-(((1R,2R)-2-(hydroxymethyl)cyclopropyl)ethynyl)biphenyl-4-yl)-2-methyl-2-(methylsulfonyl)butanamide |
| 117 | 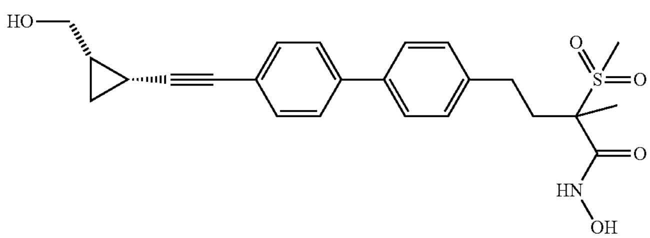 [SMILES: CC(CCc1ccc(-c2ccc(C#C[C@@H]3C[C@@H]3CO)cc2)cc1)(C(=O)NO)S(C)(=O)=O] | N-hydroxy-4-(4'-(((1R,2S)-2-(hydroxymethyl)cyclopropyl)ethynyl)biphenyl-4-yl)-2-methyl-2-(methylsulfonyl)butanamide |
| 118 | 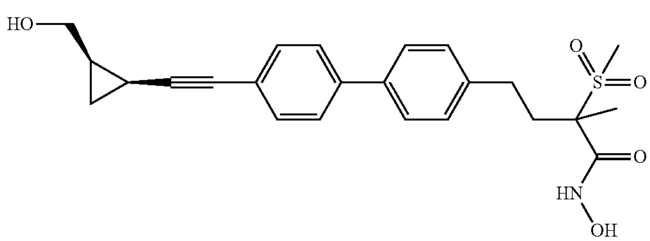 [SMILES: CC(CCc1ccc(-c2ccc(C#C[C@H]3C[C@H]3CO)cc2)cc1)(C(=O)NO)S(C)(=O)=O] | N-hydroxy-4-(4'-(((1S,2R)-2-(hydroxymethyl)cyclopropyl)ethynyl)biphenyl-4-yl)-2-methyl-2-(methylsulfonyl)butanamide |
| 119 | 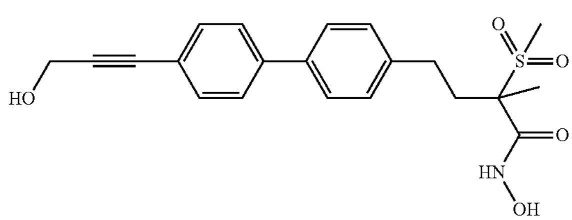 [SMILES: CC(CCc1ccc(-c2ccc(C#CCO)cc2)cc1)(C(=O)NO)S(C)(=O)=O] | N-hydroxy-4-(4'-(3-hydroxyprop-1-ynyl)biphenyl-4-yl)-2-methyl-2-(methylsulfonyl)butanamide |
| 120 | 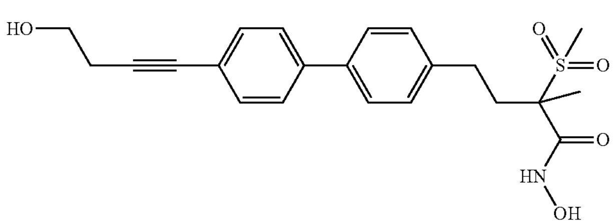 | N-hydroxy-4-(4'-(4-hydroxybut-1-ynyl)biphenyl-4-yl)-2-methyl-2-(methylsulfonyl)butanamide |

TABLE 1-continued

| # | structure | name |
|---|---|---|
| 121 | 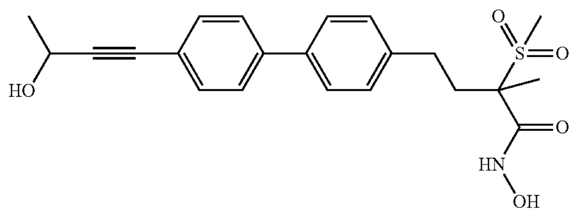 [SMILES: CC(O)C#Cc1ccc(-c2ccc(CCC(C)(C(=O)NO)S(C)(=O)=O)cc2)cc1] | N-hydroxy-4-(4'-(3-hydroxybut-1-ynyl)biphenyl-4-yl)-2-methyl-2-(methylsulfonyl)butanamide |
| 122 | 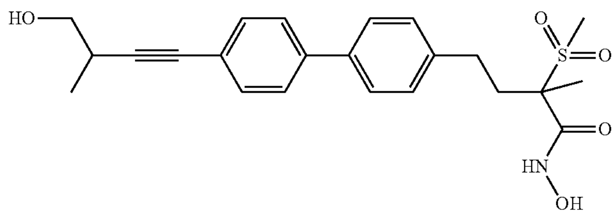 [SMILES: CC(C#Cc1ccc(-c2ccc(CCC(C)(C(=O)NO)S(C)(=O)=O)cc2)cc1)CO] | N-hydroxy-4-(4'-(4-hydroxy-3-methylbut-1-ynyl)biphenyl-4-yl)-2-methyl-2-(methylsulfonyl)butanamide |
| 123 | 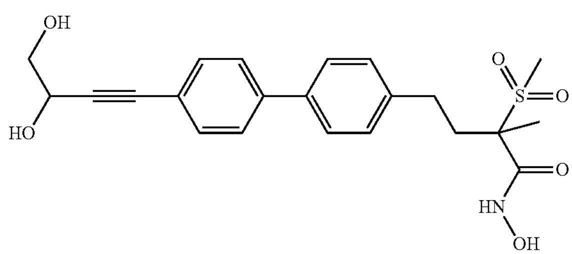 [SMILES: CC(CCc1ccc(-c2ccc(C#CC(O)CO)cc2)cc1)(C(=O)NO)S(C)(=O)=O] | 4-(4'-(3,4-dihydroxybut-1-ynyl)biphenyl-4-yl)-N-hydroxy-2-methyl-2-(methylsulfonyl)butanamide |
| 124 | 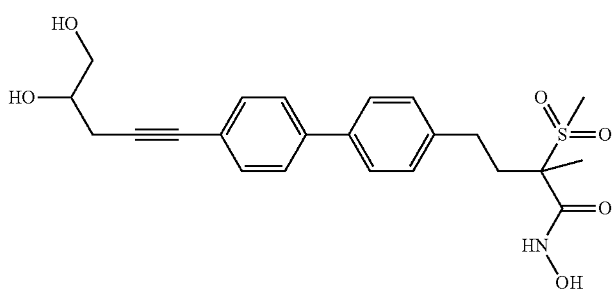 [SMILES: CC(CCc1ccc(-c2ccc(C#CCC(O)CO)cc2)cc1)(C(=O)NO)S(C)(=O)=O] | 4-(4'-(4,5-dihydroxypent-1-ynyl)biphenyl-4-yl)-N-hydroxy-2-methyl-2-(methylsulfonyl)butanamide |
| 125 | 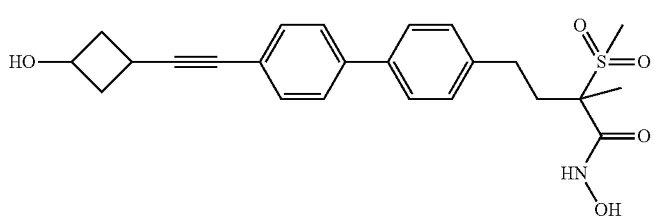 [SMILES: CC(CCc1ccc(-c2ccc(C#CC3CC(O)C3)cc2)cc1)(C(=O)NO)S(C)(=O)=O] | N-hydroxy-4-(4'-((3-hydroxycyclobutyl)ethynyl)biphenyl-4-yl)-2-methyl-2-(methylsulfonyl)butanamide |
| 126 | 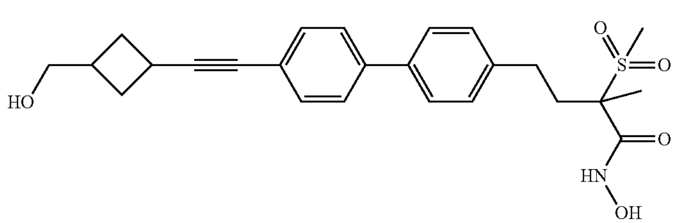 [SMILES: CC(CCc1ccc(-c2ccc(C#CC3CC(CO)C3)cc2)cc1)(C(=O)NO)S(C)(=O)=O] | N-hydroxy-4-(4'-((3-(hydroxymethyl)cyclobutyl)ethynyl)biphenyl-4-yl)-2-methyl-2-(methylsulfonyl)butanamide |

TABLE 1-continued

| # | structure | name |
|---|---|---|
| 127 | 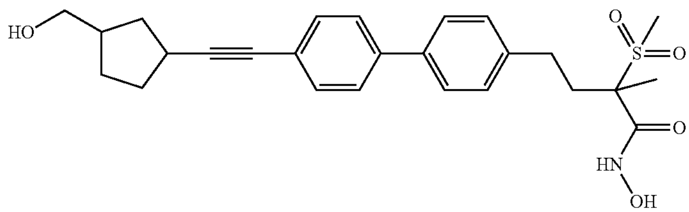 [SMILES: CC(CCc1ccc(-c2ccc(C#CC3CCC(CO)C3)cc2)cc1)(C(=O)NO)S(C)(=O)=O] | N-hydroxy-4-(4'-((3-(hydroxymethyl)cyclopentyl)ethynyl)biphenyl-4-yl)-2-methyl-2-(methylsulfonyl)butanamide |
| 128 | 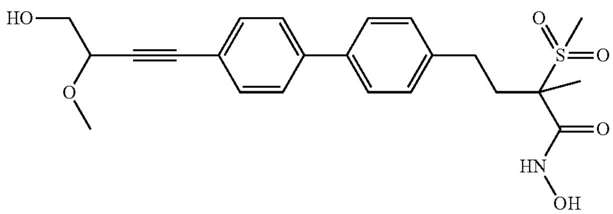 | N-hydroxy-4-(4'-(4-hydroxy-3-methoxybut-1-ynyl)biphenyl-4-yl)-2-methyl-2-(methylsulfonyl)butanamide |
| 129 | 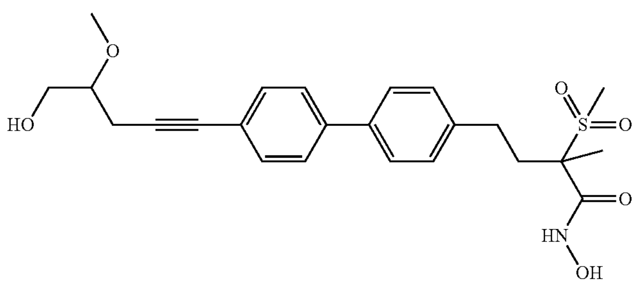 [SMILES: COC(CO)CC#Cc1ccc(-c2ccc(CCC(C)(C(=O)NO)S(C)(=O)=O)cc2)cc1] | N-hydroxy-4-(4'-(5-hydroxy-4-methoxypent-1-ynyl)biphenyl-4-yl)-2-methyl-2-(methylsulfonyl)butanamide |
| 130 | 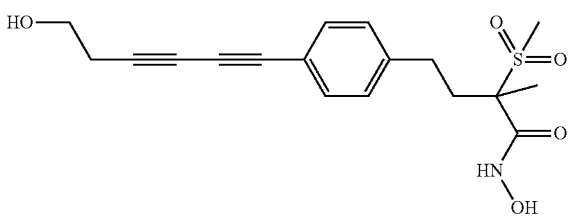 [SMILES: CC(CCc1ccc(C#CC#CCCO)cc1)(C(=O)NO)S(C)(=O)=O] | N-hydroxy-4-(4-(6-hydroxyhexa-1,3-diynyl)phenyl)-2-methyl-2-(methylsulfonyl)butanamide |
| 131 | 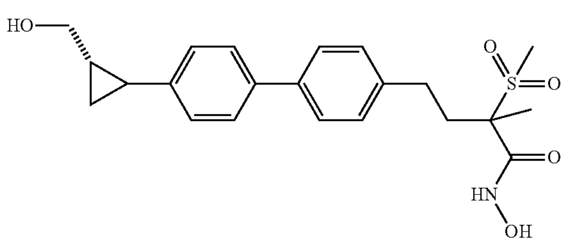 [SMILES: CC(CCc1ccc(-c2ccc(C3C[C@@H]3CO)cc2)cc1)(C(=O)NO)S(C)(=O)=O] | N-hydroxy-4-(4'-((2S)-2-(hydroxymethyl)cyclopropyl)biphenyl-4-yl)-2-methyl-2-(methylsulfonyl)butanamide |
| 132 | 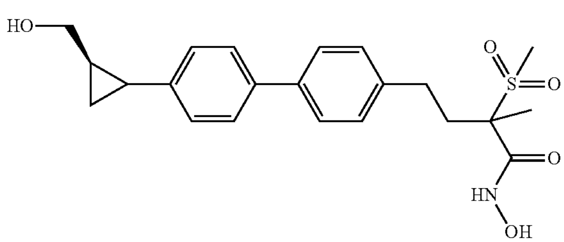 [SMILES: CC(CCc1ccc(-c2ccc(C3C[C@H]3CO)cc2)cc1)(C(=O)NO)S(C)(=O)=O] | N-hydroxy-4-(4'-((2R)-2-(hydroxymethyl)cyclopropyl)biphenyl-4-yl)-2-methyl-2-(methylsulfonyl)butanamide |

TABLE 1-continued

| # | structure | name |
|---|---|---|
| 133 | 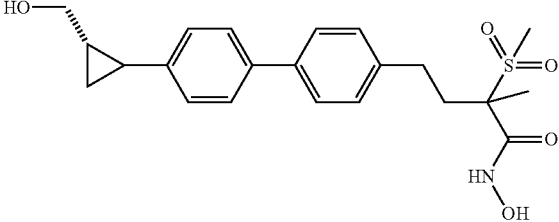 [SMILES: CC(CCc1ccc(-c2ccc(C3C[C@@H]3CO)cc2)cc1)(C(=O)NO)S(C)(=O)=O] | N-hydroxy-4-(4'-((2S)-2-(hydroxymethyl)cyclopropyl)biphenyl-4-yl)-2-methyl-2-(methylsulfonyl)butanamide |
| 134 | 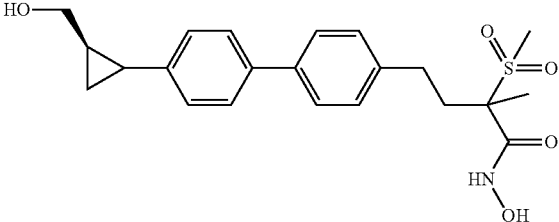 [SMILES: CC(CCc1ccc(-c2ccc(C3C[C@H]3CO)cc2)cc1)(C(=O)NO)S(C)(=O)=O] | N-hydroxy-4-(4'-((2R)-2-(hydroxymethyl)cyclopropyl)biphenyl-4-yl)-2-methyl-2-(methylsulfonyl)butanamide |
| 135 | 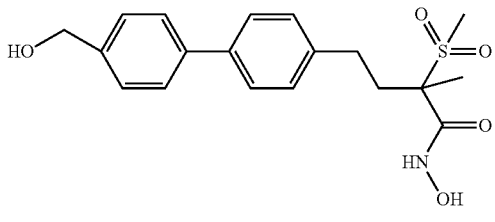 [SMILES: CC(CCc1ccc(-c2ccc(CO)cc2)cc1)(C(=O)NO)S(C)(=O)=O] | N-hydroxy-4-(4'-hydroxymethyl)biphenyl-4-yl)-2-methyl-2-(methylsulfonyl)butanamide |
| 136 | 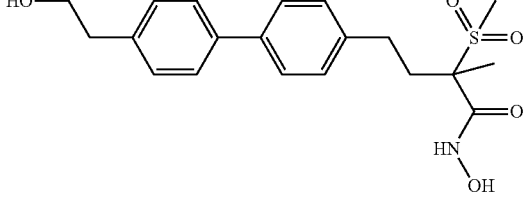 | N-hydroxy-4-(4'-(2-hydroxyethyl)biphenyl-4-yl)-2-methyl-2-(methylsulfonyl)butanamide |
| 137 | 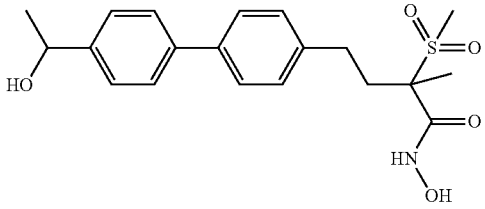 | N-hydroxy-4-(4'-(1-hydroxyethyl)biphenyl-4-yl)-2-methyl-2-(methylsulfonyl)butanamide |
| 138 | 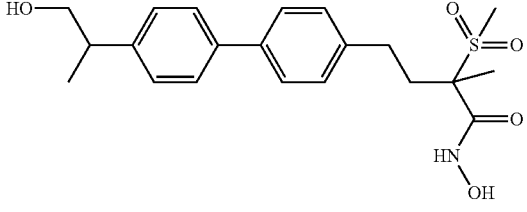 [SMILES: CC(CCc1ccc(-c2ccc(CCO)cc2)cc1)(C(=O)NO)S(C)(=O)=O] | N-hydroxy-4-(4'-(1-hydroxypropan-2-yl)biphenyl-4-yl)-2-methyl-2-(methylsulfonyl)butanamide |
| 139 | 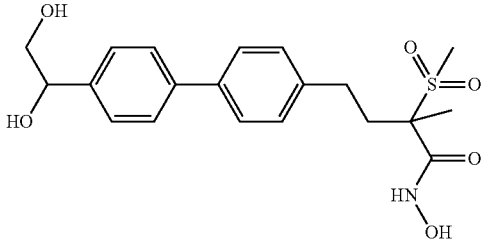 [SMILES: CC(CCc1ccc(-c2ccc(C(O)CO)cc2)cc1)(C(=O)NO)S(C)(=O)=O] | 4-(4'-(1,2-dihydroxyethyl)biphenyl-4-yl)-N-hydroxy-2-methyl-2-(methylsulfonyl)butanamide |

TABLE 1-continued

| # | structure | name |
|---|---|---|
| 140 | 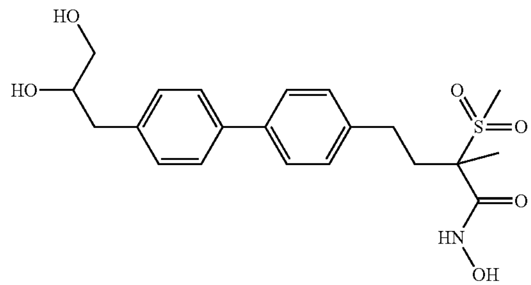 [SMILES: CC(CCc1ccc(-c2ccc(CC(O)CO)cc2)cc1)(C(=O)NO)S(C)(=O)=O] | 4-(4'-(2,3-dihydroxypropyl)biphenyl-4-yl)-N-hydroxy-2-methyl-2-(methylsulfonyl)butanamide |
| 141 | 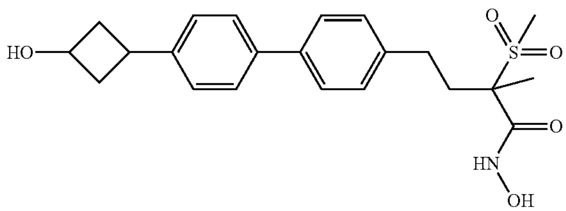 [SMILES: CC(CCc1ccc(-c2ccc(C3CC(O)C3)cc2)cc1)(C(=O)NO)S(C)(=O)=O] | N-hydroxy-4-(4'-(3-hydroxycyclobutyl)biphenyl-4-yl)-2-methyl-2-(methylsulfonyl)butanamide |
| 142 | 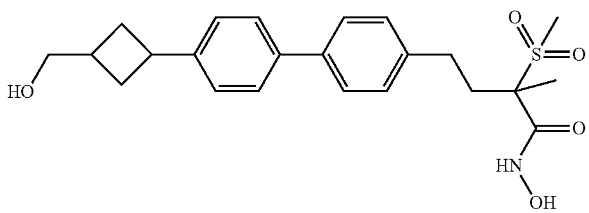 [SMILES: CC(CCc1ccc(-c2ccc(C3CC(CO)C3)cc2)cc1)(C(=O)NO)S(C)(=O)=O] | N-hydroxy-4-(4'-(3-(hydroxymethyl)cyclobutyl)biphenyl-4-yl)-2-methyl-2-(methylsulfonyl)butanamide |
| 143 | 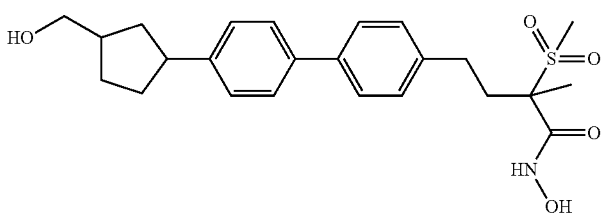 [SMILES: CC(CCc1ccc(-c2ccc(C3CCC(CO)C3)cc2)cc1)(C(=O)NO)S(C)(=O)=O] | N-hydroxy-4-(4'-(3-(hydroxymethyl)cyclopentyl)biphenyl-4-yl)-2-methyl-2-(methylsulfonyl)butanamide |
| 144 | 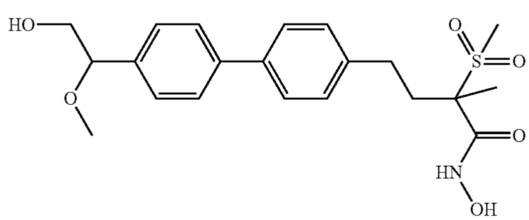 [SMILES: COC(CO)c1ccc(-c2ccc(CCC(C)(C(=O)NO)S(C)(=O)=O)cc2)cc1] | N-hydroxy-4-(4'-(2-hydroxy-1-methoxyethyl)biphenyl-4-yl)-2-methyl-2-(methylsulfonyl)butanamide |
| 145 | 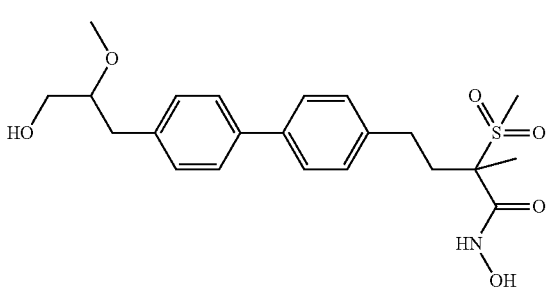 [SMILES: COC(CO)Cc1ccc(-c2ccc(CCC(C)(C(=O)NO)S(C)(=O)=O)cc2)cc1] | N-hydroxy-4-(4'-(3-hydroxy-2-methoxypropyl)biphenyl-4-yl)-2-methyl-2-(methylsulfonyl)butanamide |

TABLE 1-continued

| # | structure | name |
|---|---|---|
| 146 | 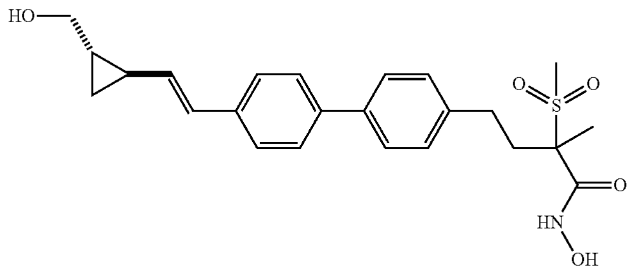 | N-hydroxy-4-(4'-((E)-2-((1R,2S)-2-(hydroxymethyl)cyclopropyl)vinyl)biphenyl-4-yl)-2-methyl-2-(methylsulfonyl)butanamide |
| 147 | 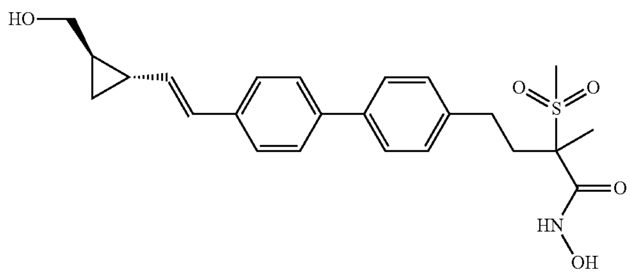 [SMILES: CC(CCc1ccc(-c2ccc(/C=C/[C@@H]3C[C@H]3CO)cc2)cc1)(C(=O)NO)S(C)(=O)=O] | N-hydroxy-4-(4'-((E)-2-((1S,2R)-2-(hydroxymethyl)cyclopropyl)vinyl)biphenyl-4-yl)-2-methyl-2-(methylsulfonyl)butanamide |
| 148 | 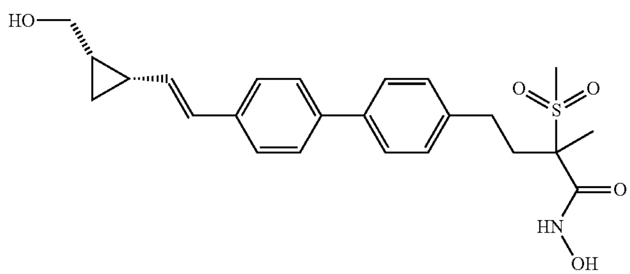 [SMILES: CC(CCc1ccc(-c2ccc(/C=C/[C@@H]3C[C@@H]3CO)cc2)cc1)(C(=O)NO)S(C)(=O)=O] | N-hydroxy-4-(4'-((E)-2-((1S,2S)-2-(hydroxymethyl)cyclopropyl)vinyl)biphenyl-4-yl)-2-methyl-2-(methylsulfonyl)butanamide |
| 149 | 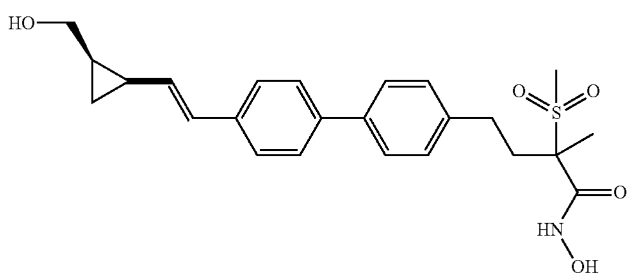 | N-hydroxy-4-(4'-((E)-2-((1R,2R)-2-(hydroxymethyl)cyclopropyl)vinyl)biphenyl-4-yl)-2-methyl-2-(methylsulfonyl)butanamide |
| 150 | 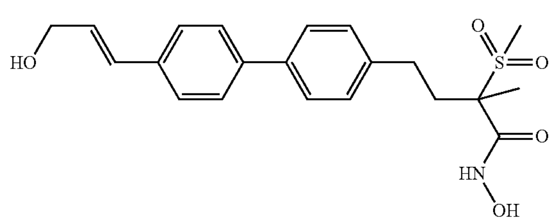 [SMILES: CC(CCc1ccc(-c2ccc(/C=C/CO)cc2)cc1)(C(=O)NO)S(C)(=O)=O] | (E)-N-hydroxy-4-(4'-(3-hydroxyprop-1-enyl)biphenyl-4-yl)-2-methyl-2-(methylsulfonyl)butanamide |
| 151 | 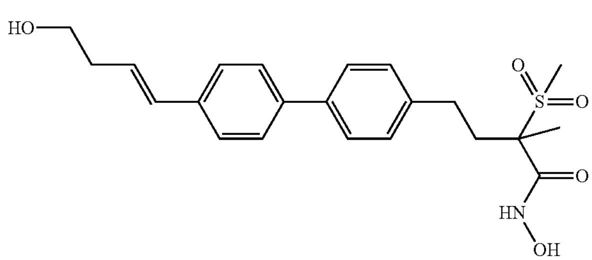 [SMILES: CC(CCc1ccc(-c2ccc(/C=C/CCO)cc2)cc1)(C(=O)NO)S(C)(=O)=O] | (E)-N-hydroxy-4-(4'-(4-hydroxybut-1-enyl) biphenyl-4-yl)-2-methyl-2-(methylsulfonyl)butanamide |

TABLE 1-continued

| # | structure | name |
|---|---|---|
| 152 | 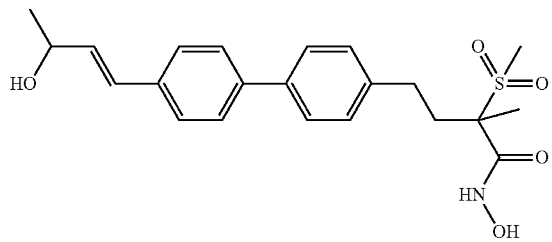 [SMILES: CC(O)/C=C/c1ccc(-c2ccc(CCC(C)(C(=O)NO)S(C)(=O)=O)cc2)cc1] | (E)-N-hydroxy-4-(4'-(3-hydroxybut-1-enyl)biphenyl-4-yl)-2-methyl-2-(methylsulfonyl)butanamide |
| 153 | 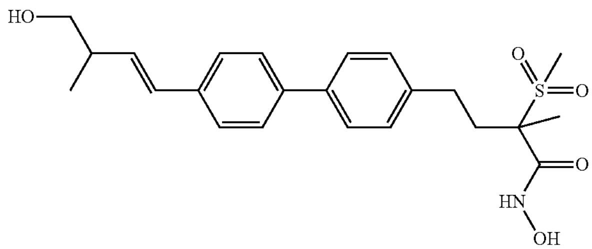 [SMILES: CC(/C=C/c1ccc(-c2ccc(CCC(C)(C(=O)NO)S(C)(=O)=O)cc2)cc1)CO] | (E)-N-hydroxy-4-(4'-(4-hydroxy-3-methylbut-1-enyl)biphenyl-4-yl)-2-methyl-2-(methylsulfonyl)butanamide |
| 154 | 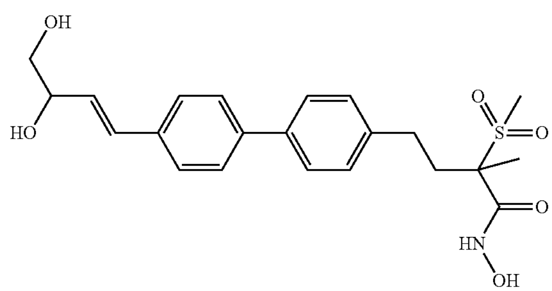 [SMILES: CC(CCc1ccc(-c2ccc(/C=C/C(O)CO)cc2)cc1)(C(=O)NO)S(C)(=O)=O] | (E)-4-(4'-(3,4-dihydroxybut-1-enyl)biphenyl-4-yl)-N-hydroxy-2-methyl-2-(methylsulfonyl)butanamide |
| 155 | 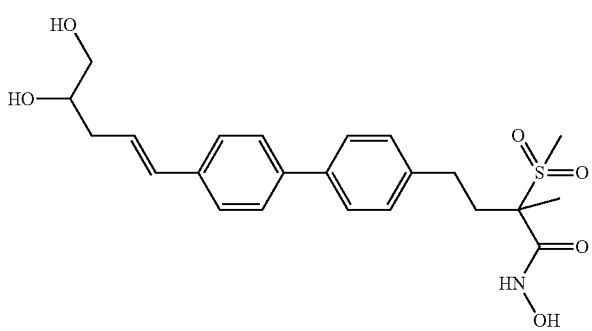 [SMILES: CC(CCc1ccc(-c2ccc(/C=C/CC(O)CO)cc2)cc1)(C(=O)NO)S(C)(=O)=O] | (E)-4-(4'-(4,5-dihydroxypent-1-enyl)biphenyl-4-yl)-N-hydroxy-2-methyl-2-(methylsulfonyl)butanamide |
| 156 | 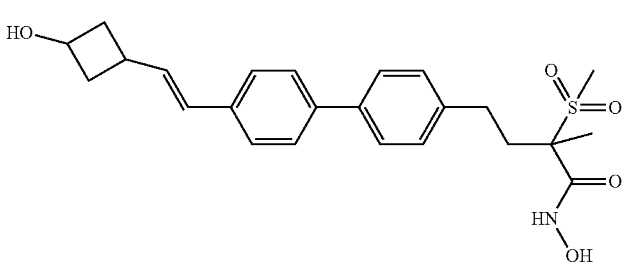 [SMILES: CC(CCc1ccc(-c2ccc(/C=C/C3CC(O)C3)cc2)cc1)(C(=O)NO)S(C)(=O)=O] | (E)-N-hydroxy-4-(4'-(2-(3-hydroxycyclobutyl)vinyl)biphenyl-4-yl)-2-methyl-2-(methylsulfonyl)butanamide |

TABLE 1-continued

| # | structure | name |
|---|---|---|
| 157 | 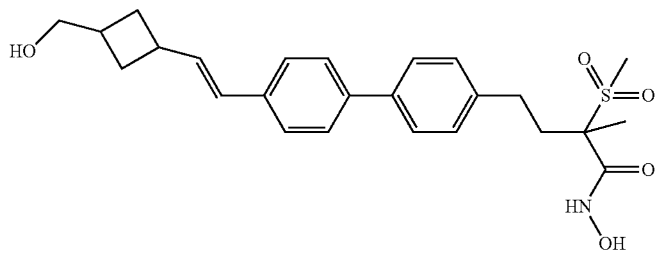 [SMILES: CC(CCc1ccc(-c2ccc(/C=C/C3CC(CO)C3)cc2)cc1)(C(=O)NO)S(C)(=O)=O] | (E)-N-hydroxy-4-(4'-(2-(3-(hydroxymethyl)cyclobutyl)vinyl)biphenyl-4-yl)-2-methyl-2-(methylsulfonyl)butanamide |
| 158 | 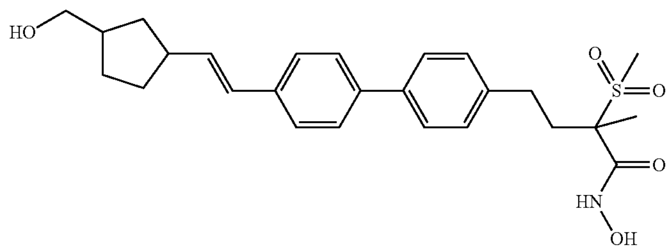 [SMILES: CC(CCc1ccc(-c2ccc(/C=C/C3CCC(CO)C3)cc2)cc1)(C(=O)NO)S(C)(=O)=O] | (E)-N-hydroxy-4-(4'-(2-(3-(hydroxymethyl)cyclopentyl)vinyl)biphenyl-4-yl)-2-methyl-2-(methylsulfonyl)butanamide |
| 159 | 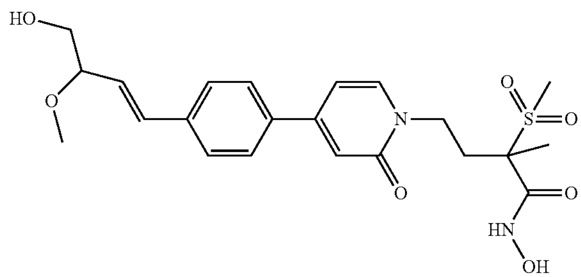 [SMILES: COC(/C=C/c1ccc(-c2ccn(CCC(C)(C(=O)NO)S(C)(=O)=O)c(=O)c2)cc1)CO] | (E)-N-hydroxy-4-(4-(4-(4-hydroxy-3-methoxybut-1-enyl)phenyl)-2-oxopyridin-1(2H)-yl)-2-methyl-2-(methylsulfonyl)butanamide |
| 160 | 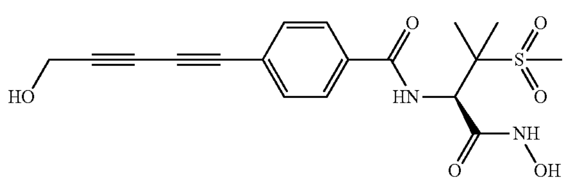 | (R)-N-(1-(hydroxyamino)-3-methyl-3-(methylsulfonyl)-1-oxobutan-2-yl)-4-(5-hydroxypenta-1,3-diynyl)benzamide |
| 161 | 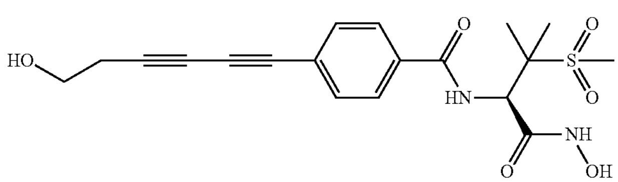 | (R)-N-(1-(hydroxyamino)-3-methyl-3-(methylsulfonyl)-1-oxobutan-2-yl)-4-(6-hydroxyhexa-1,3-diynyl)benzamide |
| 162 | 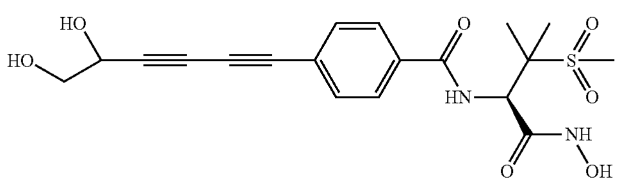 | 4-(5,6-dihydroxyhexa-1,3-diynyl)-N-((R)-1-(hydroxyamino)-3-methyl-3-(methylsulfonyl)-1-oxobutan-2-yl)benzamide |
| 163 | 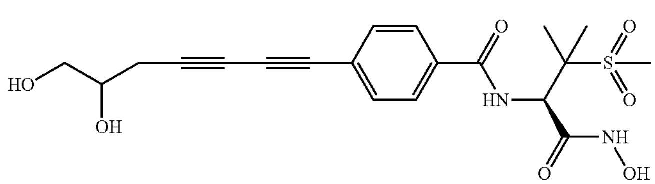 | 4-(6,7-dihydroxyhepta-1,3-diynyl)-N-((R)-1-(hydroxyamino)-3-methyl-3-(methylsulfonyl)-1-oxobutan-2-yl)benzamide |

TABLE 1-continued

| # | structure | name |
|---|---|---|
| 164 | 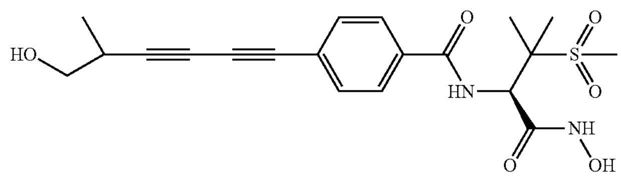 [SMILES: CC(C)([C@H](NC(=O)c1ccc(C#CC#CC(O)CO)cc1)C(=O)NO)S(C)(=O)=O] | 4-(6-hydroxy-5-methylhexa-1,3-diynyl)-N-((R)-1-(hydroxyamino)-3-methyl-3-(methylsulfonyl)-1-oxobutan-2-yl)benzamide |
| 165 | 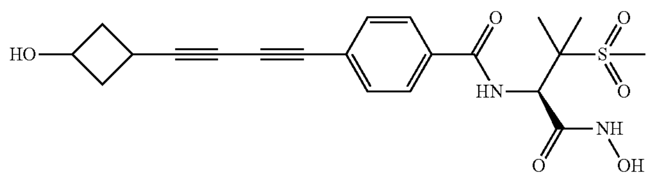 [SMILES: CC(C)([C@H](NC(=O)c1ccc(C#CC#CC2CC(O)C2)cc1)C(=O)NO)S(C)(=O)=O] | (R)-N-(1-(hydroxyamino)-3-methyl-3-(methylsulfonyl)-1-oxobutan-2-yl)-4-((3-hydroxycyclobutyl)buta-1,3-diynyl)benzamide |
| 166 | 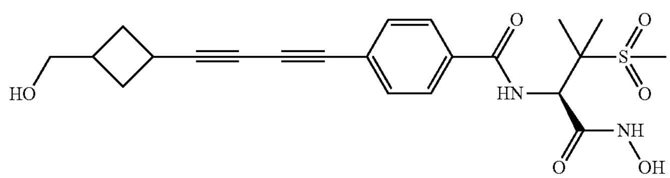 | (R)-N-(1-(hydroxyamino)-3-methyl-3-(methylsulfonyl)-1-oxobutan-2-yl)-4-((3-(hydroxymethyl)cyclobutyl)buta-1,3-diynyl)benzamide |
| 167 | 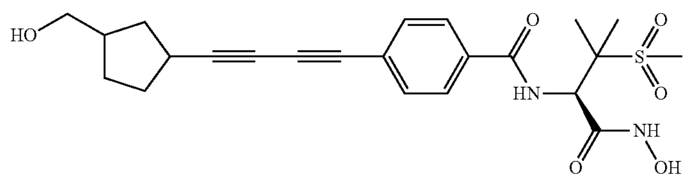 [SMILES: CC(C)([C@H](NC(=O)c1ccc(C#CC#CC2CCC(CO)C2)cc1)C(=O)NO)S(C)(=O)=O] | N-((R)-1-(hydroxyamino)-3-methyl-3-(methylsulfonyl)-1-oxobutan-2-yl)-4-((3-(hydroxymethyl)cyclopentyl)buta-1,3-diynyl)benzamide |
| 168 | 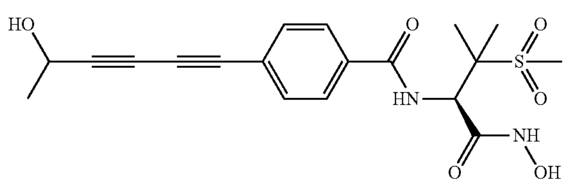 | N-((R)-1-(hydroxyamino)-3-methyl-3-(methylsulfonyl)-1-oxobutan-2-yl)-4-(5-hydroxyhexa-1,3-diynyl)benzamide |
| 169 | 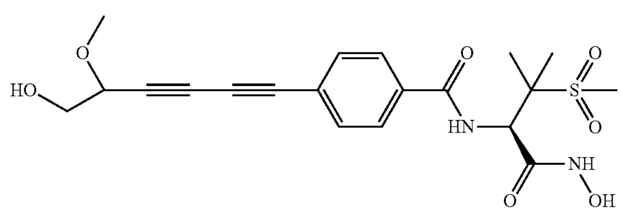 [SMILES: COC(C#CC#Cc1ccc(C(=O)N[C@H](C(=O)NO)C(C)(C)S(C)(=O)=O)cc1)CO] | 4-(6-hydroxy-5-methoxyhexa-1,3-diynyl)-N-((R)-1-(hydroxyamino)-3-methyl-3-(methylsulfonyl)-1-oxobutan-2-yl)benzamide |
| 170 | 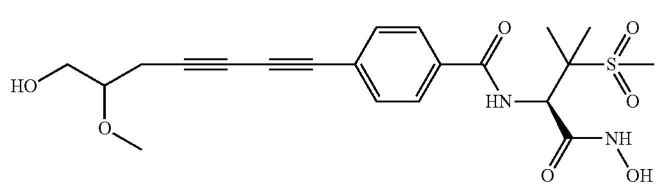 [SMILES: COC(CO)CC#CC#Cc1ccc(C(=O)N[C@H](C(=O)NO)C(C)(C)S(C)(=O)=O)cc1] | 4-(7-hydroxy-6-methoxyhepta-1,3-diynyl)-N-((R)-1-(hydroxyamino)-3-methyl-3-(methylsulfonyl)-1-oxobutan-2-yl)benzamide |
| 171 | 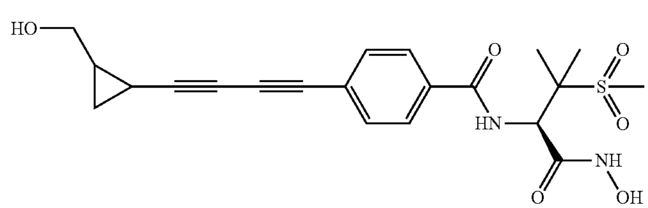 [SMILES: CC(C)([C@H](NC(=O)c1ccc(C#CC#CC2CC2CO)cc1)C(=O)NO)S(C)(=O)=O] | N-((R)-1-(hydroxyamino)-3-methyl-3-(methylsulfonyl)-1-oxobutan-2-yl)-4-((2-(hydroxymethyl)cyclopropyl)buta-1,3-diynyl)benzamide |

TABLE 1-continued

| # | structure | name |
|---|-----------|------|
| 172 | 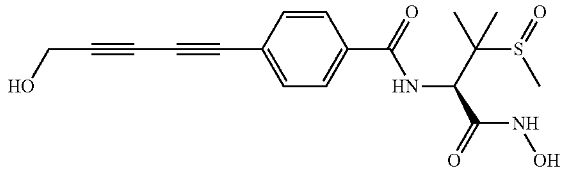 [SMILES: CS(=O)C(C)(C)[C@H](NC(=O)c1ccc(C#CC#CCO)cc1)C(=O)NO] | N-((2R)-1-(hydroxyamino)-3-methyl-3-(methylsulfinyl)-1-oxobutan-2-yl)-4-(5-hydroxypenta-1,3-diynyl)benzamide |
| 173 | 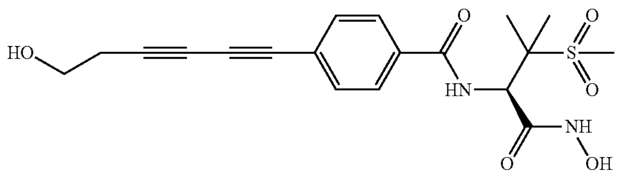 | N-((2R)-1-(hydroxyamino)-3-methyl-3-(methylsulfinyl)-1-oxobutan-2-yl)-4-(6-hydroxyhexa-1,3-diynyl)benzamide |
| 174 | 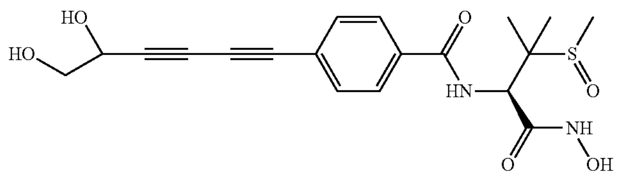 | 4-(5,6-dihydroxyhexa-1,3-diynyl)-N-((2R)-1-(hydroxyamino)-3-methyl-3-(methylsulfinyl)-1-oxobutan-2-yl)benzamide |
| 175 | 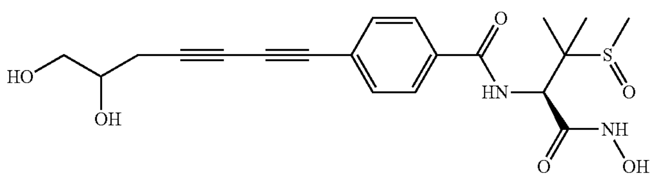 [SMILES: CS(=O)C(C)(C)[C@H](NC(=O)c1ccc(C#CC#CCC(O)CO)cc1)C(=O)NO] | 4-(6,7-dihydroxyhepta-1,3-diynyl)-N-((2R)-1-(hydroxyamino)-3-methyl-3-(methylsulfinyl)-1-oxobutan-2-yl)benzamide |
| 176 | 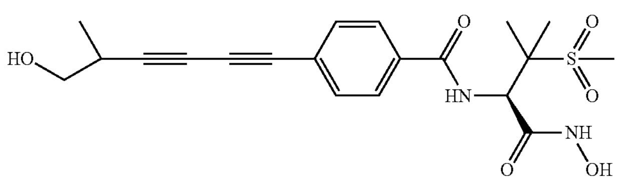 | 4-(6-hydroxy-5-methylhexa-1,3-diynyl)-N-((R)-1-(hydroxyamino)-3-methyl-3-(methylsulfonyl)-1-oxobutan-2-yl)benzamide |
| 177 | 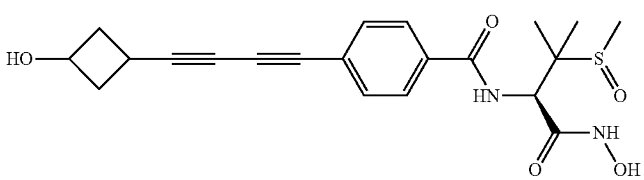 | N-((2R)-1-(hydroxyamino)-3-methyl-3-(methylsulfinyl)-1-oxobutan-2-yl)-4-((3-hydroxycyclobutyl)buta-1,3-diynyl)benzamide |
| 178 | 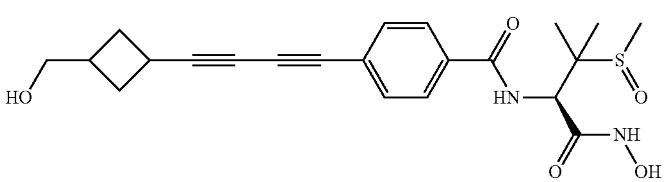 | N-((2R)-1-(hydroxyamino)-3-methyl-3-(methylsulfinyl)-1-oxobutan-2-yl)-4-((3-(hydroxymethyl)cyclobutyl)buta-1,3-diynyl)benzamide |
| 179 | 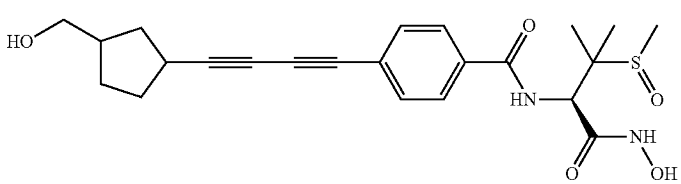 [SMILES: CS(=O)C(C)(C)[C@H](NC(=O)c1ccc(C#CC#CC2CCC(CO)C2)cc1)C(=O)NO] | N-((2R)-1-(hydroxyamino)-3-methyl-3-(methylsulfinyl)-1-oxobutan-2-yl)-4-((3-(hydroxymethyl)cyclopenlyl)buta-1,3-diynyl)benzamide |

TABLE 1-continued

| # | structure | name |
|---|---|---|
| 180 | 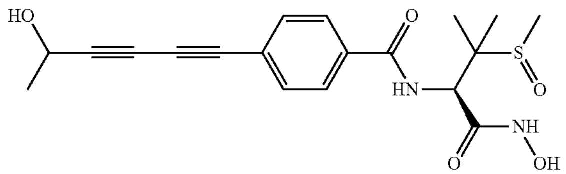 [SMILES: CC(O)C#CC#Cc1ccc(C(=O)N[C@H](C(=O)NO)C(C)(C)S(C)=O)cc1] | N-((2R)-1-(hydroxyamino)-3-methyl-3-(methylsulfinyl)-1-oxobutan-2-yl)-4-(5-hydroxyhexa-1,3-diynyl)benzamide |
| 181 | 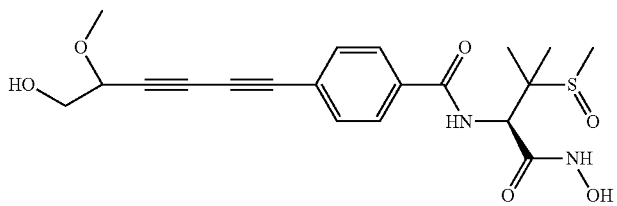 [SMILES: COC(C#CC#Cc1ccc(C(=O)N[C@H](C(=O)NO)C(C)(C)S(C)=O)cc1)CO] | 4-(6-hydroxy-5-methoxyhexa-1,3-diynyl)-N-((2R)-1-(hydroxyamino)-3-methyl-3-(methylsulfinyl)-1-oxobutan-2-yl)benzamide |
| 182 | 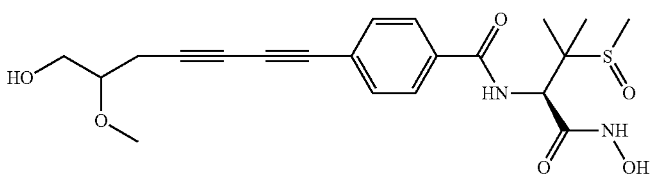 [SMILES: COC(CO)CC#CC#Cc1ccc(C(=O)N[C@H](C(=O)NO)C(C)(C)S(C)=O)cc1] | 4-(7-hydroxy-6-methoxyhepta-1,3-diynyl)-N-((2R)-1-(hydroxyamino)-3-methyl-3-(methylsulfinyl)-1-oxobutan-2-yl)benzamide |
| 183 | 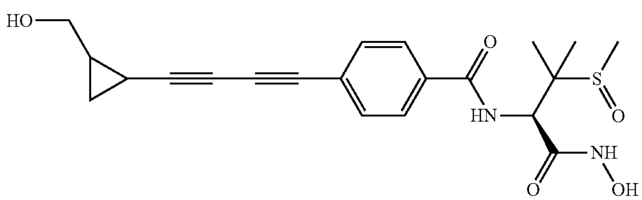 | N-((2R)-1-(hydroxyamino)-3-methyl-3-(methylsulfinyl)-1-oxobutan-2-yl)-4-((2-(hydroxymethyl)cyclopropyl)buta-1,3-diynyl)benzamide |
| 184 | 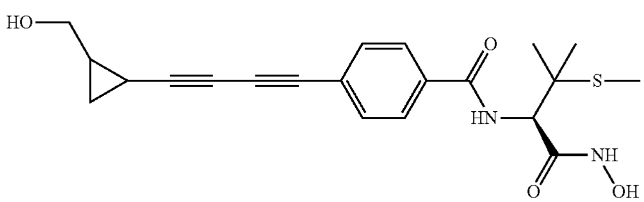 [SMILES: CSC(C)(C)[C@H](NC(=O)c1ccc(C#CC#CC2CC2CO)cc1)C(=O)NO] | N-((R)-1-(hydroxyamino)-3-methyl-3-(methylthio)-1-oxobutan-2-yl)-4-((2-(hydroxymethyl)cyclopropyl)buta-1,3-diynyl)benzamide |
| 185 | 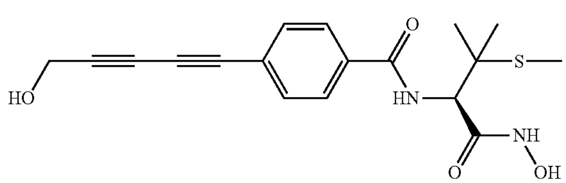 [SMILES: CSC(C)(C)[C@H](NC(=O)c1ccc(C#CC#CCO)cc1)C(=O)NO] | (R)-N-(1-(hydroxyamino)-3-methyl-3-(methylthio)-1-oxobutan-2-yl)-4-(5-hydroxypenta-1,3-diynyl)benzamide |
| 186 | 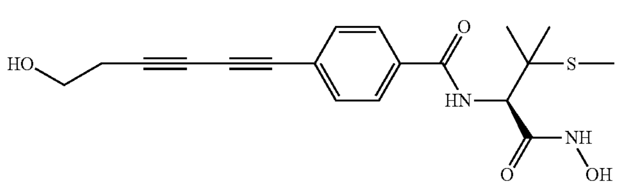 | (R)-N-(1-(hydroxyamino)-3-methyl-3-(methylthio)-1-oxobutan-2-yl)-4-(6-hydroxyhexa-1,3-diynyl)benzamide |
| 187 | 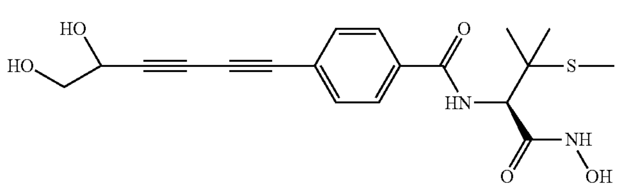 | 4-(5,6-dihydroxyhexa-1,3-diynyl)-N-((R)-1-(hydroxyamino)-3-methyl-3-(methylthio)-1-oxobutan-2-yl)benzamide |

TABLE 1-continued

| # | structure | name |
|---|---|---|
| 188 | 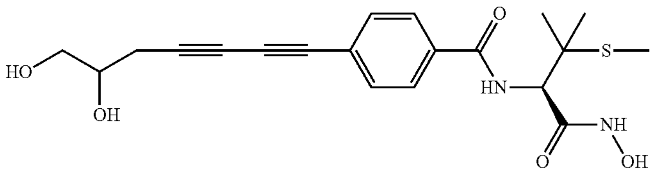 [SMILES: CSC(C)(C)[C@H](NC(=O)c1ccc(C#CC#CCC(O)CO)cc1)C(=O)NO] | 4-(6,7-dihydroxyhepta-1,3-diynyl)-N-((R)-1-(hydroxyamino)-3-methyl-3-(methylthio)-1-oxobutan-2-yl)benzamide |
| 189 | 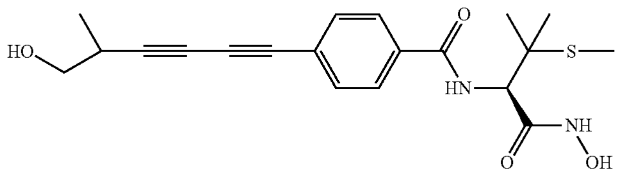 [SMILES: CSC(C)(C)[C@H](NC(=O)c1ccc(C#CC#CC(C)CO)cc1)C(=O)NO] | 4-(6-hydroxy-5-methylhexa-1,3-diynyl)-N-((R)-1-(hydroxyamino)-3-methyl-3-(methylthio)-1-oxobutan-2-yl)benzamide |
| 190 | 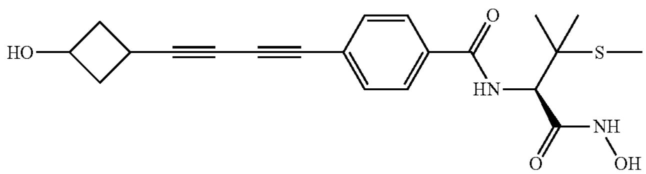 [SMILES: CSC(C)(C)[C@H](NC(=O)c1ccc(C#CC#CC2CC(O)C2)cc1)C(=O)NO] | (R)-N-(1-(hydroxyamino)-3-methyl-3-(methylthio)-1-oxobutan-2-yl)-4-((3-hydroxycyclobutyl)buta-1,3-diynyl)benzamide |
| 191 | 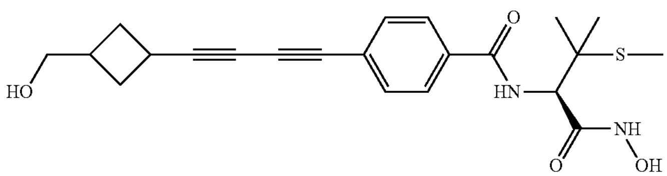 [SMILES: CSC(C)(C)[C@H](NC(=O)c1ccc(C#CC#CC2CC(CO)C2)cc1)C(=O)NO] | (R)-N-(1-(hydroxyamino)-3-methyl-3-(methylthio)-1-oxobutan-2-yl)-4-((3-(hydroxymethyl)cyclobutyl)buta-1,3-diynyl)benzamide |
| 192 | 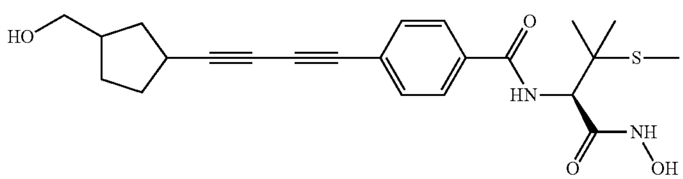 [SMILES: CSC(C)(C)[C@H](NC(=O)c1ccc(C#CC#CC2CCC(CO)C2)cc1)C(=O)NO] | N-((R)-1-(hydroxyamino)-3-methyl-3-(methylthio)-1-oxobutan-2-yl)-4-((3-(hydroxymethyl)cyclopentyl)buta-1,3-diynyl)benzamide |
| 193 | 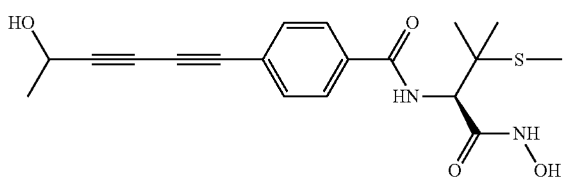 [SMILES: CSC(C)(C)[C@H](NC(=O)c1ccc(C#CC#CC(C)O)cc1)C(=O)NO] | N-((R)-1-(hydroxyamino)-3-methyl-3-(methylthio)-1-oxobutan-2-yl)-4-(5-hydroxyhexa-1,3-diynyl)benzamide |
| 194 | 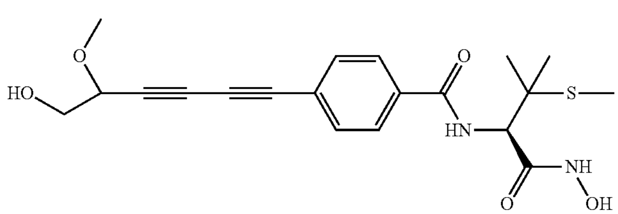 [SMILES: COC(C#CC#Cc1ccc(C(=O)N[C@H](C(=O)NO)C(C)(C)SC)cc1)CO] | 4-(6-hydroxy-5-methoxyhexa-1,3-diynyl)-N-((R)-1-(hydroxyamino)-3-methyl-3-(methylthio)-1-oxobutan-2-yl)benzamide |
| 195 | 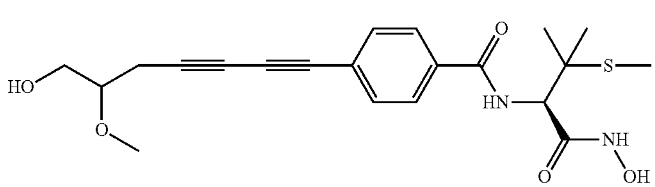 | 4-(7-hydroxy-6-methoxyhepta-1,3-diynyl)-N-((R)-1-(hydroxyamino)-3-methyl-3-(methylthio)-1-oxobutan-2-yl)benzamide |

TABLE 1-continued

| # | structure | name |
|---|---|---|
| 196 | 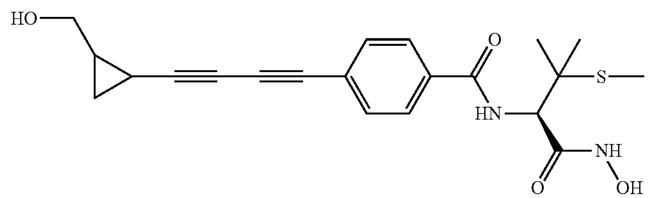 [SMILES: CSC(C)(C)[C@H](NC(=O)c1ccc(C#CC#CC2CC2CO)cc1)C(=O)NO] | N-((R)-1-(hydroxyamino)-3-methyl-3-(methylthio)-1-oxobutan-2-yl)-4-((2-(hydroxymethyl)cyclopropyl)buta-1,3-diynyl)benzamide |
| 197 | 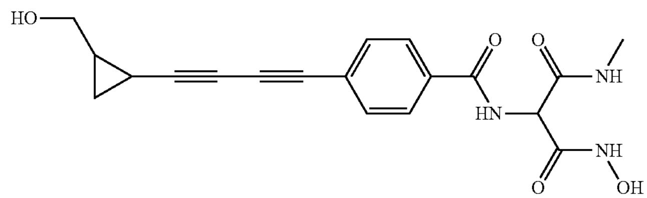 [SMILES: CNC(=O)C(NC(=O)c1ccc(C#CC#CC2CC2CO)cc1)C(=O)NO] | N1-hydroxy-2-(4-((2-(hydroxymethyl)cyclopropyl)buta-1,3-diynyl)benzamido)-N3-methylmalonamide |
| 198 | 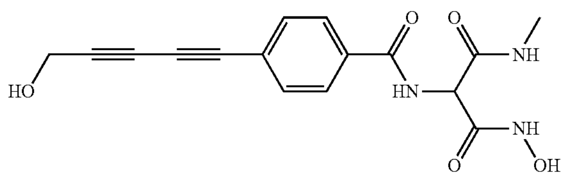 | N1-hydroxy-2-(4-(5-hydroxypenta-1,3-diynyl)benzamido)-N3-methylmalonamide |
| 199 | 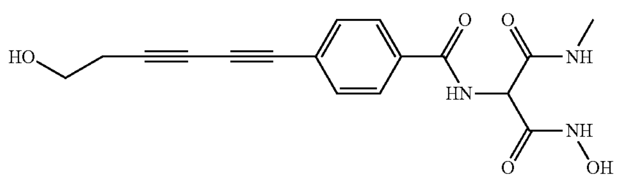 [SMILES: CNC(=O)C(NC(=O)c1ccc(C#CC#CCCO)cc1)C(=O)NO] | N1-hydroxy-2-(4-(6-hydroxyhexa-1,3-diynyl)benzamido)- N3-methylmalonamide |
| 200 | 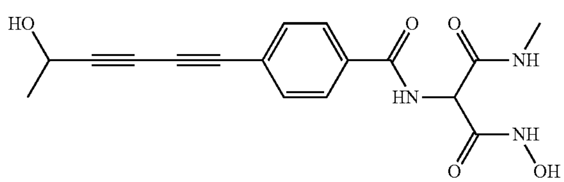 [SMILES: CNC(=O)C(NC(=O)c1ccc(C#CC#CC(C)O)cc1)C(=O)NO] | N1-hydroxy-2-(4-(5-hydroxyhexa-1,3-diynyl)benzamido)-N3-methylmalonamide |
| 201 | 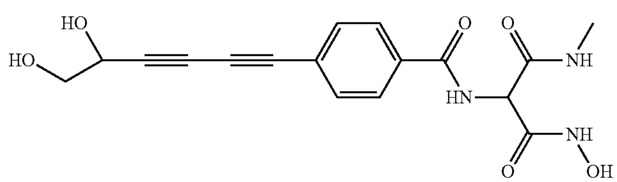 | 2-(4-(5,6-dihydroxyhexa-1,3-diynyl)benzamido)-N1-hydroxy-N3-methylmalonamide |
| 202 | 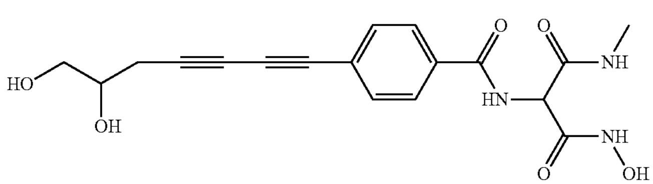 [SMILES: CNC(=O)C(NC(=O)c1ccc(C#CC#CCC(O)CO)cc1)C(=O)NO] | 2-(4-(6,7-dihydroxyhepta-1,3-diynyl)benzamido)- N1-hydroxy-N3-methylmalonamide |
| 203 | 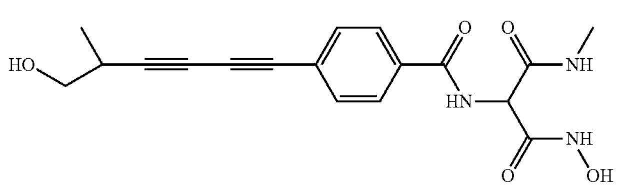 | N1-hydroxy-2-(4-(6-hydroxy-5-methylhexa-1,3-diynyl)benzamido)-N3-methylmalonamide |

TABLE 1-continued

| # | structure | name |
|---|---|---|
| 204 | 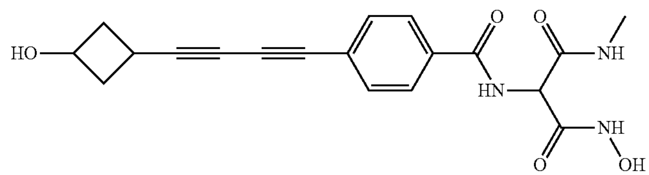 [SMILES: CNC(=O)C(NC(=O)c1ccc(C#CC#CC2CC(O)C2)cc1)C(=O)NO] | N1-hydroxy-2-(4-((3-hydroxycyclobutyl)buta-1,3-diynyl)benzamido)-N3-methylmalonamide |
| 205 | 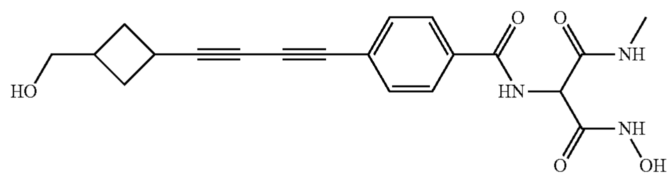 [SMILES: CNC(=O)C(NC(=O)c1ccc(C#CC#CC2CC(CO)C2)cc1)C(=O)NO] | N1-hydroxy-2-(4-((3-(hydroxymethyl)cyclobutyl)buta-1,3-diynyl)benzamido)- N3-methylmalonamide |
| 206 | 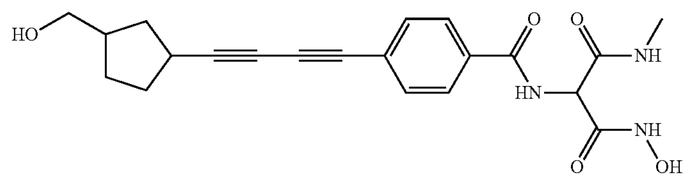 [SMILES: CNC(=O)C(NC(=O)c1ccc(C#CC#CC2CCC(CO)C2)cc1)C(=O)NO] | N1-hydroxy-2-(4-((3-(hydroxymethyl)cyclopentyl)buta-1,3-diynyl)benzamido)-N3-methylmalonamide |
| 207 | 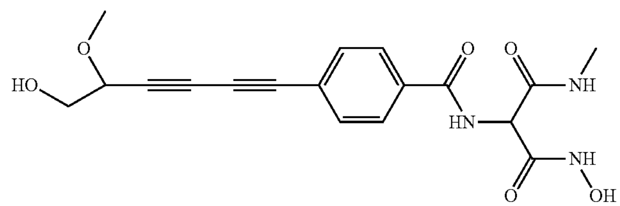 [SMILES: CNC(=O)C(NC(=O)c1ccc(C#CC#CC(CO)OC)cc1)C(=O)NO] | N1-hydroxy-2-(4-(6-hydroxy-5-methoxyhexa-1,3-diynyl)benzamido)-N3-methylmalonamide |
| 208 | 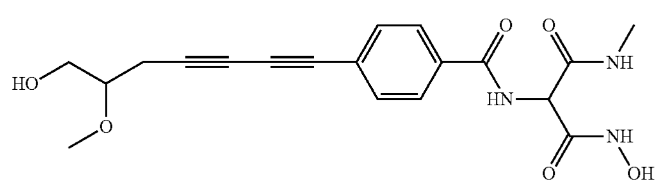 [SMILES: CNC(=O)C(NC(=O)c1ccc(C#CC#CCC(CO)OC)cc1)C(=O)NO] | N1-hydroxy-2-(4-(7-hydroxy-6-methoxyhepta-1,3-diynyl)benzamido)-N3-methylmalonamide |
| 209 | 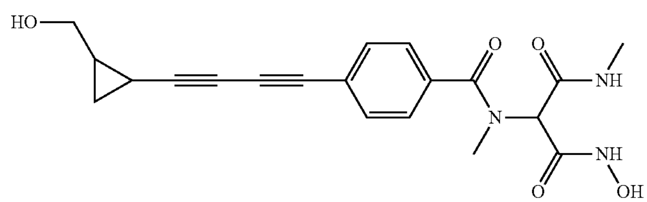 [SMILES: CNC(=O)C(C(=O)NO)N(C)C(=O)c1ccc(C#CC#CC2CC2CO)cc1] | N1-hydroxy-2-(4-((2-(hydroxymethyl)cyclopropyl)buta-1,3-diynyl)-N-methylbenzamido)-N3-methylmalonamide |
| 210 | 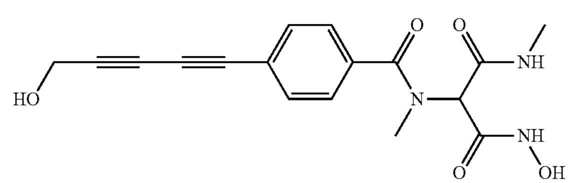 | N1-hydroxy-2-(4-(5-hydroxypenta-1,3-diynyl)-N-methylbenzamido)-N3-methylmalonamide |
| 211 | 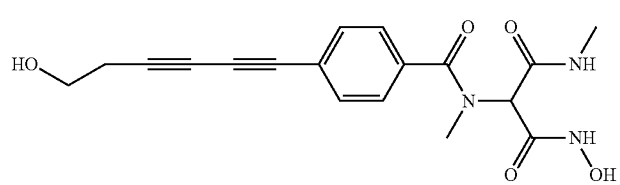 [SMILES: CNC(=O)C(C(=O)NO)N(C)C(=O)c1ccc(C#CC#CCCO)cc1] | N1-hydroxy-2-(4-(6-hydroxyhexa-1,3-diynyl)-N-methylbenzamido)-N3-methylmalonamide |

TABLE 1-continued

| # | structure | name |
|---|---|---|
| 217 | | N1-hydroxy-2-(4-(5-hydroxyhexa-1,3-diynyl)-N-methylbenzamido)-N3-methylmalonamide |
| 213 | 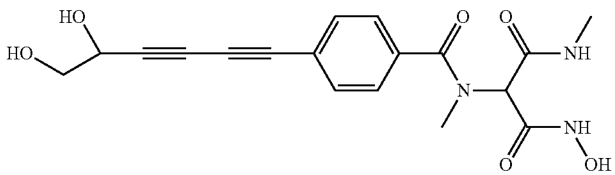 [SMILES: CNC(=O)C(C(=O)NO)N(C)C(=O)c1ccc(C#CC#CC(O)CO)cc1] | 2-(4-(5,6-dihydroxyhexa-1,3-diynyl)-N-methylbenzamido)-N1-hydroxy-N3-methylmalonamide |
| 214 | 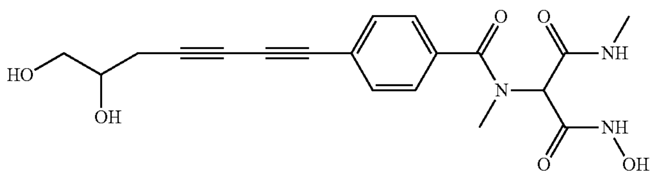 | 2-(4-(6,7-dihydroxyhepta-1,3-diynyl)-N-methylbenzamido)-N1-hydroxy-N3-methylmalonamide |
| 215 | 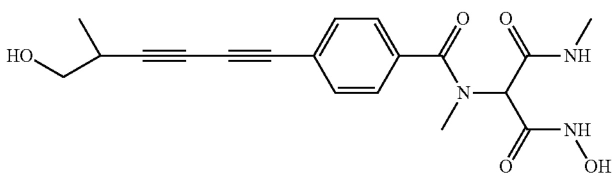 | N1-hydroxy-2-(4-(6-hydroxy-5-methylhexa-1,3-diynyl)-N-methylbenzamido)-N3-methylmalonamide |
| 216 | 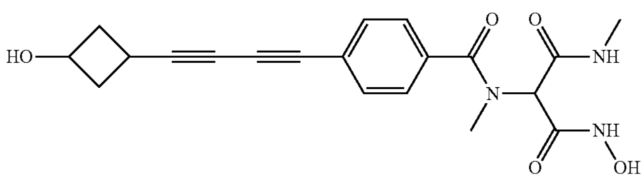 [SMILES: CNC(=O)C(C(=O)NO)N(C)C(=O)c1ccc(C#CC#CC2CC(O)C2)cc1] | N1-hydroxy-2-(4-((3-hydroxycyclobutyl)buta-1,3-diynyl)-N-methylbenzamido)-N3-methylmalonamide |
| 217 | | N1-hydroxy-2-(4-((3-(hydroxymethyl)cyclobutyl)buta-1,3-diynyl)-N-methylbenzamido)-N3-methylmalonamide |
| 218 | 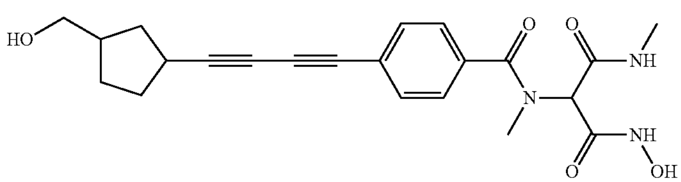 [SMILES: CNC(=O)C(C(=O)NO)N(C)C(=O)c1ccc(C#CC#CC2CCC(CO)C2)cc1] | N1-hydroxy-2-(4-((3-(hydroxymethyl)cyclopentyl)buta-1,3-diynyl)-N-methylbenzamido)-N3-methylmalonamide |
| 219 | 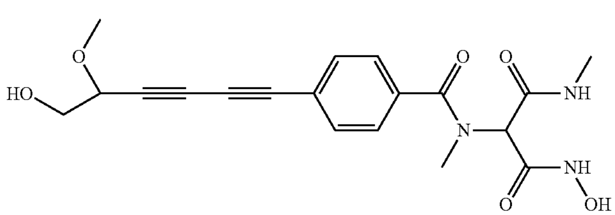 [SMILES: CNC(=O)C(C(=O)NO)N(C)C(=O)c1ccc(C#CC#CC(CO)OC)cc1] | N1-hydroxy-2-(4-(6-hydroxy-5-methoxyhexa-1,3-diynyl)-N-methylbenzamido)-N3-methylmalonamide |

TABLE 1-continued

| # | structure | name |
|---|---|---|
| 220 | 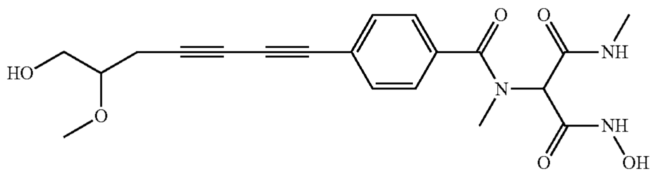 | N1-hydroxy-2-(4-(7-hydroxy-6-methoxyhepta-1,3-diynyl)-N-methylbenzamido)-N3-methylmalonamide |
| 221 | 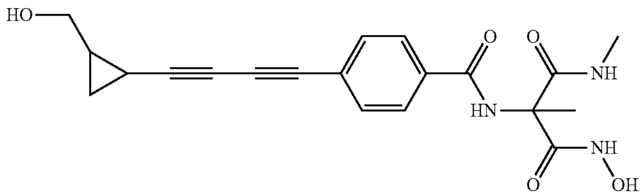 [SMILES: CNC(=O)C(C)(NC(=O)c1ccc(C#CC#CC2CC2CO)cc1)C(=O)NO] | N1-hydroxy-2-(4-((2-(hydroxymethyl)cyclopropyl)buta-1,3-diynyl)benzamido)-N3,2-dimethylmalonamide |
| 222 | 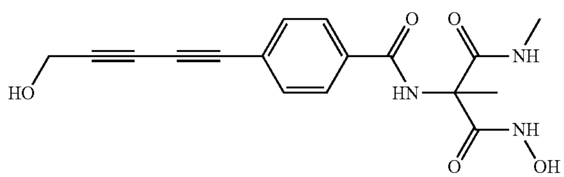 | N1-hydroxy-2-(4-(5-hydroxypenta-1,3-diynyl)benzamido)-N3,2-dimethylmalonamide |
| 223 | 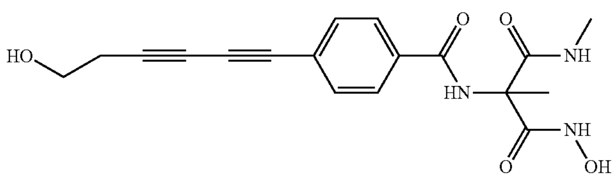 [SMILES: CNC(=O)C(C)(NC(=O)c1ccc(C#CC#CCCO)cc1)C(=O)NO] | N1-hydroxy-2-(4-(6-hydroxyhexa-1,3-diynyl)benzamido)-N3,2-dimethylmalonamide |
| 224 | 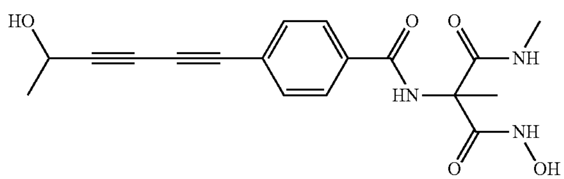 | N1-hydroxy-2-(4-(5-hydroxyhexa-1,3-diynyl)benzamido)-N3,2-dimethylmalonamide |
| 225 | 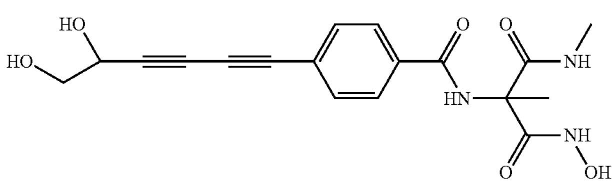 | 2-(4-(5,6-dihydroxyhexa-1,3-diynyl)benzamido)-N1-hydroxy-N3,2-dimethylmalonamide |
| 226 | 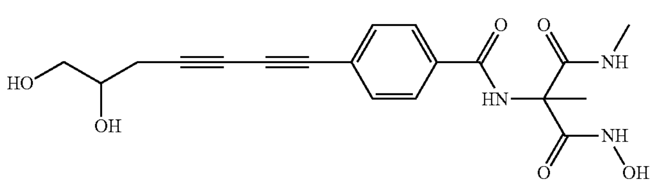 [SMILES: CNC(=O)C(C)(NC(=O)c1ccc(C#CC#CCC(O)CO)cc1)C(=O)NO] | 2-(4-(6,7-dihydroxyhepta-1,3-diynyl)benzamido)-N1-hydroxy-N3,2-dimethylmalonamide |
| 227 | 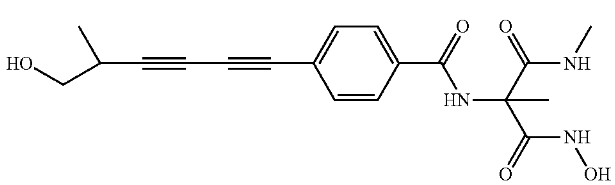 [SMILES: CNC(=O)C(C)(NC(=O)c1ccc(C#CC#CC(C)CO)cc1)C(=O)NO] | N1-hydroxy-2-(4-(6-hydroxy-5-methylhexa-1,3-diynyl)benzamido)-N3,2-dimethylmalonamide |

TABLE 1-continued

| # | structure | name |
|---|---|---|
| 228 | 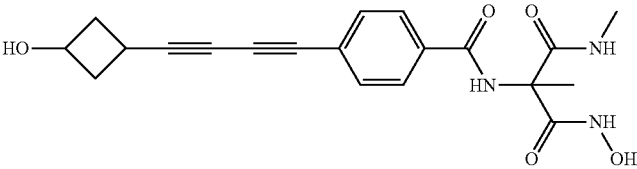 | N1-hydroxy-2-(4-((3-hydroxycyclobutyl)buta-1,3-diynyl)benzamido)-N3,2-dimethylmalonamide |
| 229 | 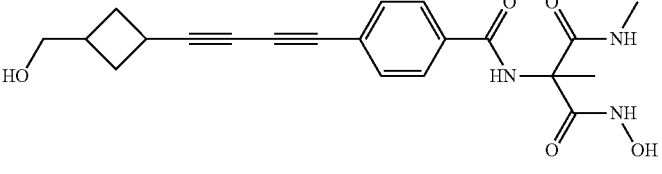 | N1-hydroxy-2-(4-((3-(hydroxymethyl)cyclobutyl)buta-1,3-diynyl)benzamido)- N3,2-dimethylmalonamide |
| 230 | 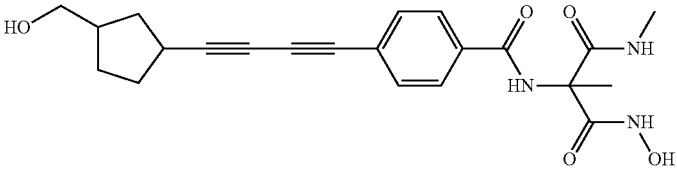 [SMILES: CNC(=O)C(C)(NC(=O)c1ccc(C#CC#CC2CCC(CO)C2)cc1)C(=O)NO] | N1-hydroxy-2-(4-((3-(hydroxymethyl)cyclopentyl)buta-1,3-diynyl)benzamido)-N3,2-dimethylmalonamide |
| 231 | 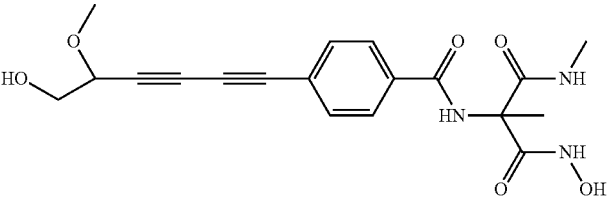 [SMILES: CNC(=O)C(C)(NC(=O)c1ccc(C#CC#CC(CO)OC)cc1)C(=O)NO] | N1-hydroxy-2-(4-(6-hydroxy-5-methoxyhexa-1,3-diynyl)benzamido)-N3,2-dimethylmalonamide |
| 232 | 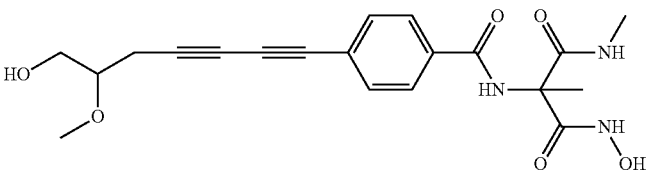 [SMILES: CNC(=O)C(C)(NC(=O)c1ccc(C#CC#CCC(CO)OC)cc1)C(=O)NO] | N1-hydroxy-2-(4-(7-hydroxy-6-methoxyhepta-1,3-diynyl)benzamido)-N3,2-dimethylmalonamide |
| 233 | 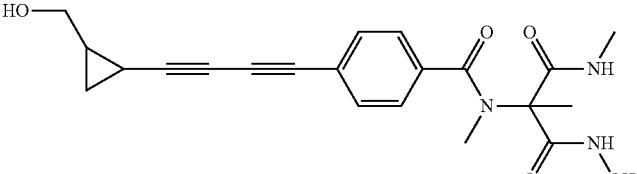 | N1-hydroxy-2-(4-((2-(hydroxymethyl)cyclopropyl)buta-1,3-diynyl)-N-methylbenzamido)-N3,2-dimethylmalonamide |
| 234 | 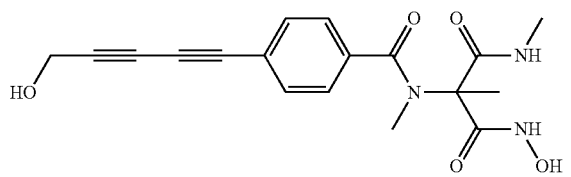 [SMILES: CNC(=O)C(C)(C(=O)NO)N(C)C(=O)c1ccc(C#CC#CCO)cc1] | N1-hydroxy-2-(4-(5-hydroxypenta-1,3-diynyl)-N-methylbenzamido)-N3,2-dimethylmalonamide |
| 235 | 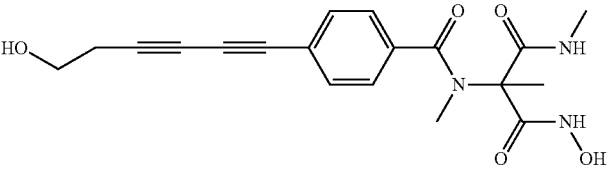 | N1-hydroxy-2-(4-(6-hydroxyhexa-1,3-diynyl)-N-methylbenzamido)-N3,2-dimethylmalonamide |

TABLE 1-continued

| # | structure | name |
|---|---|---|
| 236 | 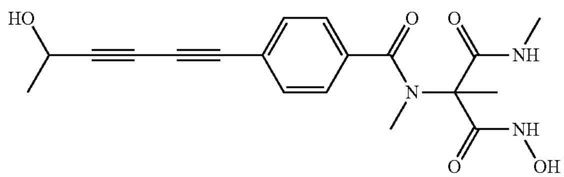 [SMILES: CNC(=O)C(C)(C(=O)NO)N(C)C(=O)c1ccc(C#CC#CC(C)O)cc1] | N1-hydroxy-2-(4-(5-hydroxyhexa-1,3-diynyl)-N-methylbenzamido)-N3,2-dimethylmalonamide |
| 237 | 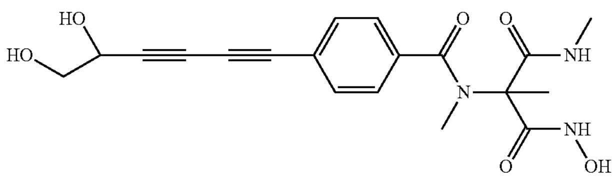 [SMILES: CNC(=O)C(C)(C(=O)NO)N(C)C(=O)c1ccc(C#CC#CC(C)CO)cc1] | 2-(4-(5,6-dihydroxyhexa-1,3-diynyl)-N-methylbenzamido)-N1-hydroxy-N3,2-dimethylmalonamide |
| 238 | 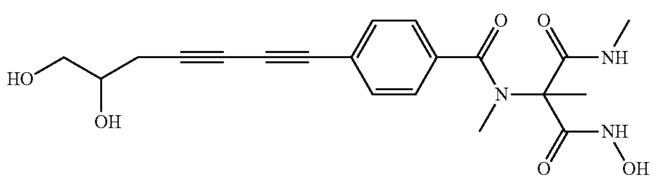 | 2-(4-(6,7-dihydroxyhepta-1,3-diynyl)-N-methylbenzamido)-N1-hydroxy-N3,2-dimethylmalonamide |
| 239 | 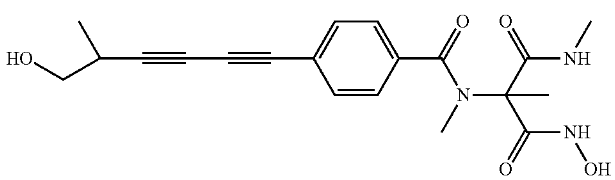 | N1-hydroxy-2-(4-(6-hydroxy-5-methylhexa-1,3-diynyl)-N-methylbenzamido)-N3,2-dimethylmalonamide |
| 240 | 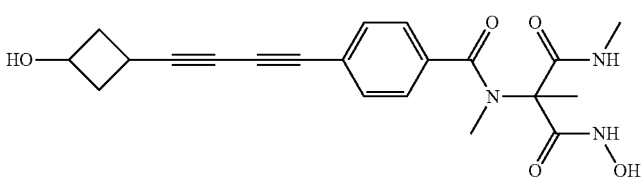 | N1-hydroxy-2-(4-((3-hydroxycyclobutyl)buta-1,3-diynyl)-N-methylbenzamido)-N3,2-dimethylmalonamide |
| 241 | 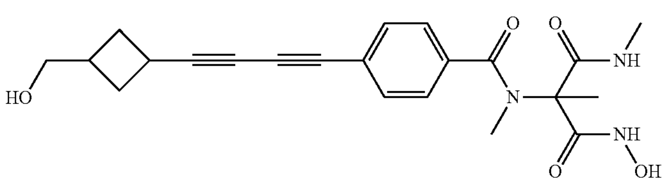 | N1-hydroxy-2-(4-((3-(hydroxymethyl)cyclobutyl)buta-1,3-diynyl)-N-methylbenzamido)-N3,2-dimethylmalonamide |
| 242 | 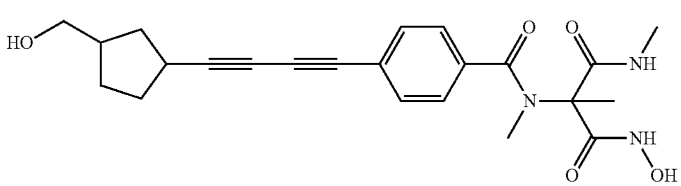 [SMILES: CNC(=O)C(C)(C(=O)NO)N(C)C(=O)c1ccc(C#CC#CC2CCC(CO)C2)cc1] | N1-hydroxy-2-(4-((3-(hydroxymethyl)cyclopentyl)buta-1,3-diynyl)-N-methylbenzamido)-N3,2-dimethylmalonamide |
| 243 | 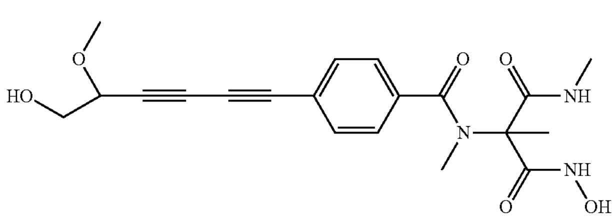 [SMILES: CNC(=O)C(C)(C(=O)NO)N(C)C(=O)c1ccc(C#CC#CC(CO)OC)cc1] | N1-hydroxy-2-(4-(6-hydroxy-5-methoxyhexa-1,3-diynyl)-N-methylbenzamido)-N3,2-dimethylmalonamide |

TABLE 1-continued

| # | structure | name |
|---|---|---|
| 244 | 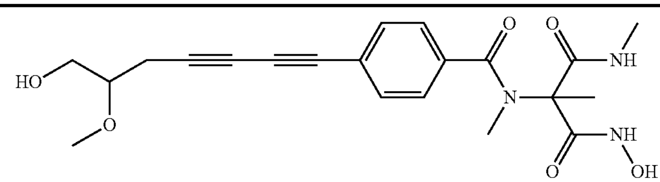 | N1-hydroxy-2-(4-(7-hydroxy-6-methoxyhepta-1,3-diynyl)-N-methylbenzamido)-N3,2-dimethylmalonamide |

Compounds of the present invention can be readily synthesized using the methods described herein, or other methods, that are well known in the art. For example, the synthesis of hxdroxamic acids or similar scaffolds having a wide variety of substituents are comprehensively reviewed in Kline, T., et al., "Potent, novel in vitro inhibitors of the *Pseudomonas aeruginosa* deacetylase LpxC" *J. Med Chem.* 2002, 45(14), 3112-29; U.S. Pat. No. 5,925,659; Pirrung, M. C., et al., "A Convenient Procedure for the Preparation of Amino Acid Hydroxamates from Esters" *J. Org. Chem.* 1995, 60, 8084-8085; Nhu, K., et al., "A New and Efficient Solid Phase Synthesis of Hydroxamic Acids" *J. Org. Chem.* 1997, 62, 7088-7089; Internationa PCT Publication No. WO98/18754; Mellor, S. L., et al., "N-Fmoc-aminoxy-2-chlortrityl Polystyrene Resin: A Facile Solid-phase Methodology for the Synthesis of Hydroxamic Acids" *Tetrahedron Lett.* 1997, 38, 3311-3314; Khan, S. I., et al., "A Facile and Convenient Solid-phase Procedure for Synthesizing Nucleoside Hydroxamic Acids" *Terahedron. Lett.* 1998, 39, 8031-8034; Zhang, Y., et al., "Design, Combinatorial Chemical Synthesis, and in vitro Characterization of Novel Urea Based Gelatinase Inhibitors" *Bioorg. Med. Chem. Lett.* 1999, 9, 2823-2826; Ito, Y., et al., "Synthetic Reactions by Complex Catalysts. XXXI, A Novel and Versatile Method of Heterocycle Synthesis" *J. Am Chem. Soc.* 1973, 95, 4447-4448; Ito, Y., et al., "Synthetic Reactions by Complex Catalysts XXXV" Syn. Commun. 1974, 4, 97-103; Witte, H., et al., "Cyclische Imidsaurester aus Nitrilen and Aminoalkoholen" *Liebigs Ann. Chem.* 1974, 996-1009; Pattenden, G., et al., "Naturally Occurring Linear Fused Thiazoline-Thiazole Containing Metabolites: Total Synthesis of (–)-Didehydromirabazole A, a Cytotoxic Alkaloid from Blue-Green Algae" *J. Chem. Soc. Perkin Trans* 1993, 1, 1629-1636; Boyce, R. J., et al., "Total Synthesis of Thiangazole, A Novel Naturally Occurring HIV-1 Inhibitor from Polyangium sp." *Tetrahedron* 1995, 51, 7321-7330; Galeotti, N., et al., "Synthesis of Peptidyl Aldehydes from Thiazolines" *Tetrahedron. Lett.* 1997, 38, 2459-2462; Charette, A. B., et al., "Mild Method for the Synthesis of Thiazolines from Secondary and Tertiary Amides" *J. Org. Chem.* 1998, 63, 908-909; Bergeron, R. J., et al., "Effects of C-4 Stereochemistry and C-4' Hydroxylation on the Iron Clearing Efficiency and Toxicity of Desferrithiocin Analogues" *J. Med. Chem.* 1999, 42, 2432-2440; Raman, P., et al., "Titanium (IV)-mediated Tandem Deprotection-cyclodehydration of Protected Cysteine N-Amides: Biomimetic Synthesis of Thiazoline- and Thiazole-containing Heterocycles" *Org. Lett.* 2000, 2, 3289-3292; Fernandez, X., et al., "Novel Synthesis of 2-Thioazolines" *Tetrahedron Lett.* 2000, 41, 3381-3384; and Wipf, P., et al., "C. Thiolysis of Oxazolinenes: A New, Selective Method for the Direct Conversion of Peptide Oxazolines into Thiazolines" *Tetrahedron Lett.* 1995, 36, 6395-6398, which are incorporated herein by reference.

In another aspect, the present invention provides a pharmaceutical composition comprising a compound of Formula I, or a stereoisomer or pharmaceutically acceptable salt thereof, and a pharmaceutically acceptable carrier or diluent.

In another aspect, the invention provides a method of inhibiting a deacetylase enzyme in a gram-negative bacteria, thereby affecting bacterial growth, comprising administering to a subject in need of such inhibition a compound of Formula I or a stereoisomer or pharmaceutically acceptable salt thereof.

In another aspect, the invention provides a method of inhibiting LpxC, thereby modulating the virulence of a bacterial infection, comprising administering to a subject in need of such inhibition a compound of Formula I or a stereoisomer or pharmaceutically acceptable salt thereof. In certain embodiments of the method of inhibiting LpxC using a compound of the present invention, the $IC_{50}$ value of the compound is less than or equal to 10 μM with respect to LpxC. In other embodiments, the $IC_{50}$ value is less than or equal to 1 μM, is less than or equal to 0.1 μM, is less than or equal to 0.050 μM, is less than or equal to 0.030 μM, is less than or equal to 0.025 μM, or is less than or equal to 0.010 μM.

In another aspect, the invention provides a method for treating a subject having a gram-negative bacterial infection comprising administering to the subject in need thereof an antibacterially effective amount of a compound of Formula I or a stereoisomer or pharmaceutically acceptable salt thereof.

In another aspect, the invention provides a method of administering a therapeutically effective amount of a compound of Formula I or a stereoisomer or pharmaceutically acceptable salt thereof to a subject infected with a fermentative or non-fermentative gram-negative bacteria. Examples of fermentative or non-fermentative gram-negative bacteria include *Pseudomonas aeruginosa*, *Stenotrophomonas maltophila*, *Burkholderia cepacia*, *Alcaligenes xylosoxidans*, *Enterobacteriaceae*, *Haemophilus*, *Franciscellaceae* (e.g., *Franciscella tularensis*) and *Neisseria* species.

In another aspect, the invention provides a method of administering an inhibitory amount of a compound described herein to gram-negative bacteria, such as *Enterobacteriaceae* which is selected from the group consisting of organisms such as *Serratia*, *Proteus*, *Klebsiella*, *Enterobacter*, *Citrobacter*, *Salmonella*, *Providencia*, *Yersinia* (e.g., *Yersinia pestis*), *Morganella*, *Cedecea*, *Edwardsiella* species and *Escherichia coli*.

In certain embodiments, the subject may be a mammal, and in some embodiments, a human.

Bacterial infections susceptible to treatment according to the present invention include primary infections and co-infections caused by a species of bacteria and one or more additional infectious agents such as, for example, bacteria, virus, parasite and fungus.

Compounds of the invention can be used for treating conditions caused by the bacterial production of endotoxin and, in particular, by gram-negative bacteria and bacteria that use LpxC in the biosynthesis of lipopolysaccharide (LPS) or endotoxin.

Compounds of the invention also are useful in treating conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, treatment includes the administration of a compound of the invention, or a combination of compounds of the invention, optionally with a second agent wherein the second agent is a second antibacterial agent or a non-antibacterial agent.

For sepsis, septic shock, systemic inflammation, localized inflammation, chronic obstructive pulmonary disease (COPD) and acute exacerbations of chronic bronchitis (AECB), representative non-antibacterial agents include antiendotoxins including endotoxin receptor-binding antibodies, endotoxin-binding antibodies, anti-CD14-binding protein antibodies, antilipopolysaccharide-binding protein antibodies and tyrosine kinase inhibitors.

In treatment of serious or chronic respiratory tract infections, compounds of the present invention may also be used with non-antibacterial agents administered via inhalation. Representative non-antibacterial agents used in this treatment include anti-inflammatory steroids, non-steroidal anti-inflammatory agents, bronchiodilators, mucolytics, anti-asthma therapeutics and lung fluid surfactants. In particular, the non-antibacterial agent may be albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, salmeterol, formoterol, indacaterol, bronchiodilators, mucolytics, calfactant, beractant, poractant alfa, surfaxin or pulmozyme (also called domase alfa).

Compounds of the invention can be used alone or in combination with a second antibacterial agent for the treatment of a serious or chronic respiratory tract infection including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Alcaligenes xylosoxidans, Flavobacterium meningosepticum, Providencia stuartii* and *Citrobacter freundi*, community lung infections such as those caused by *Haemophilus Influenzae, Legionella* species, *Moraxella catarrhalis, Branhamella catarrhalis, Enterobacter* species, *Klebsiella* species, and *Proteus* species, infections caused by other bacterial species such as *Neisseria* species, *Shigella* species, *Salmonella* species, *Helicobacter pylori, Vibrionaceae* and *Bordetella* species, as well as infections caused by a *Brucella* species, *Francisella tularensis* and/or *Yersinia Pestis*.

When used for treating subjects infected with gram-negative bacterial infections, compounds of the present invention can be used to sensitize gram-negative bacteria to the effects of a second agent.

The present invention provides novel combinations of compounds including a compound of Formula I, or a stereoisomer or pharmaceutically acceptable salt thereof, as well as methods for treating subjects infected with gram-negative bacteria. The novel combinations provided herein can be formulated into pharmaceutical formulations and medicaments that are useful in the methods of the invention. The invention also provides for the use of the novel combinations in preparing medicaments and pharmaceutical formulations, for use of the combinations in treating bacterial infections in a subject.

In one embodiment, a second antibacterial agent is used in combination with a compound of Formula I, or stereoisomer or pharmaceutically acceptable salt thereof. Examples of suitable second antibactieral agents include, but are not limited to, vancomycin, linezolid, azithromycin, imipenem, teicoplanin, daptomycin, clindamycin, rifampin, cefotaxime, gentamicin, novobiocin or telavancin. In one such embodiment, the antibacterial agent is vancomycin, teicoplanin, rifampin, azithromycin, telavancin or novobiocin. In certain embodiments the second antibacterial agent is vancomycin or rifampin. In some embodiments of the invention, the second antibacterial agent and/or the compound of Formula I, or stereoisomer or pharmaceutically acceptable salt thereof, is administered at a sub-therapeutic dose, wherein a subtherapeutic dose is a dose that would be insufficient to treat bacterial infections, if administered alone.

Pharmaceutical compositions of the present invention comprise a therapeutically effective amount of a compound of Formula I, or a stereoisomer or pharmaceutically acceptable salt thereof, formulated together with one or more pharmaceutically acceptable carriers or diluents. As used herein, the term "pharmaceutically acceptable carrier" means a non-toxic, inert solid, semi-solid or liquid filler, diluent, encapsulating material or formulation auxiliary of any type. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally (as by intravenous, intramuscular or subcutaneous injection), intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, 1% lidocaine, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions that are compatible with body tissues.

Compositions for rectal or vaginal administration are preferably suppositories that can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The antibacterial compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like arealso contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in subjects with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 μm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 μm. Predominantly in this application means that at least 70% but preferably more than 90% of all generated aerosol particles are 1 to 5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb and AeroDose vibrating porous plate nebulizers (AeroGen, Inc., Sunnyvale, Calif.), Sidestream7 nebulizers (Medic-Aid Ltd., West Sussex, England), Pari LC7 and Pari LC Star7 jet nebulizers (Pari Respiratory Equipment, Inc., Richmond, Va.), and Aerosonic (DeVilbiss Medizinische Produkte (Deutschland) GmbH, Heiden, Germany) and UltraAire7 (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a subject such as a human or lower mammal by administering to the subject a therapeutically effective amount of a compound of Formula I, or a stereoisomer or pharmaceutically acceptable salt thereof, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 200 mg/kg body weight or more usually from 0.1 to 50 mg/kg body weight. In certain embodiments, the total daily dose administered to a human or other mammal is from 1.0 to 100 mg/kg body weight or from 5.0 to 25 mg/kg body weight. Single dose compositions may contain such amounts or submultiples thereof to make up the daily dose. In general, treatment regimens according to the present invention comprise administration to a subject in need of such treatment from about 10 mg to about 15 g of the compound(s) of this invention per day in single or multiple doses, more usually, from 100 mg to 5 g, and even more usually from 250 mg to 1 g per day in single or multiple doses.

Methods of formulation are well known in the art and are disclosed, for example, in Remington: The Science and Practice of Pharmacy, Mack Publishing Company, Easton, Pa., 19th Edition (1995). Pharmaceutical compositions for use in thepresent invention can be in the form of sterile, non-pyrogenic liquid solutions or suspensions, coated capsules, suppositories, lyophilized powders, transdermal patches or other forms known in the art.

A "kit" as used in the instant application includes a container for containing the pharmaceutical compositions and may also include divided containers such as a divided bottle or a divided foil packet. The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil that is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or other health care provider, or subject, e.g., in the form of numbers next to the tablets or capsules whereby the numbers correspond with the days of the regimen that the tablets or capsules so specified should be ingested or a card that contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter, that indicates the number of daily doses that has been dispensed. Another example of such a memory-aid is a battery-powered microchip memory coupled with a liquid crystal readout, or audible reminder signal that, for example, reads out the date that the last daily dose has been taken and/or reminds one when the next dose is to be taken.

The kits of the present invention may also include, in addition to a compound of the present invention, one or more additional pharmaceutically active compounds. For example, the additional compound second antibacterial. The additional compounds may be administered in the same dosage form as the compound of the present invention or in a different dosage form. Likewise, the additional compounds can be administered at the same time as the compound of the present invention or at different times.

Compositions of the present compounds may also be used in combination with other known antibacterial agents of similar spectrum to (1) enhance treatment of severe gram-negative infections covered by the spectrum of this compound or (2) add coverage in severe infections in which multiple organisms are suspected in which another agent of a different spectrum may be required in addition to this compound. Potential agents include members of the aminoglycosides, penicillins, cephalosporins, fluoroquinolones, macrolides, glycopeptides, lipopeptides and oxazolidinones. The treatment can involve administering a composition having both a compound of the present invention and a second antibacterial compound or administration of a compound of the present inventive compounds followed by or preceded by administration of a second antibacterial agent.

The foregoing may be better understood by reference to the following examples, that are presented for illustration and not to limit the scope of the inventive concepts.

V. EXAMPLES

HPLC: Angilent 1200; Mobile Phase: A: water (0.01% TFA) B:ACN (0.01% TFA); Column: ZORBAX SB-C18, 5 um, 4.6*150 mm; Oven Temperature: 50° C.

LCMS: Angilent 1200; Mobile Phase: A: water (0.01% TFA) B:ACN (0.01% TFA), Column: SunFire C18 3.5 um, 4.6*50 mm; Oven Temperature: 50° C.

GCMS: Agilent instrument (7890A Series gas chromatograph with a Mass Selective Detector 5975C; injector volume: 1 mL; initial column temperature: 40° C.; final column temperature: 250 C; ramp time: 8.4 min; gas flow rate: 1.2 mL/min; column: 5% phenyl methyl silox, Model:Agilent 19091s-433:325C, dimensions: 30.0 m'250u m'0.25 um)

NMR: Bruker AVANCE III 400 MHz, UltraShield-Plus™ Digital NMR

A. Compound Synthesis

Referring to the examples that follow, compounds of the present invention were characterized by high performance liquid chromatography (HPLC) using a Waters Millenium chromatography system with a 2690 Separation Module (Milford, Mass.) or an Agilent 1200; Mobile Phase: A: water (0.01% TFA) B:ACN (0.01% TFA); Column: ZORBAX SB-C18, 5 um, 4.6*150 mm; Oven Temperature: 50° C. or an Agilent 1100 series chromatography system (Santa Clara, Ca). The analytical columns were Phenomenex Luna C18(2) reversed phase, 10 µm, 100 Å, axia packed, 2.0×50 mm and the preparative columns were Phenomenex Luna C18(2) reversed phase, 10 µm, 100 Å, axia packed, 21.2×250 or 50×250 mm. A gradient elution was used, typically starting with 100% water and progressing to 100% acetonitrile over a varying lengths of time All solvents contained 0.1% acetic acid (AcOH). Compounds were detected by ultraviolet light (UV) absorption at either 220 or 254 nm. In some instances, purity was assessed by thin layer chromatography (TLC) using glass or plastic backed silica gel plates, such as, for example, Baker-Flex Silica Gel 1 B2-F flexible sheets. TLC results were readily detected visually under ultraviolet light, or by employing well known iodine vapor and other various staining techniques Mass spectrometric analysis was performed on one of three LCMS instruments: a Waters System. (Alliance HT HPLC and a Micromass ZQ mass spectrometer; Column: Eclipse XDB-C-18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). or an Agilent System (Series 1100 HPLC; Column: Waters Sunfire C18 reversed phase, 2.5 µm, 100 Å, 2.1×50 mm; solvent system: 1-95% acetonitrile in water with 0.1% TFA; flow rate 0.5 mL/min; molecular weight range 150-1500; cone Voltage 70 V; column temperature 35° C.), or an Agilent 1200; Mobile Phase: A:water (0.01% TFA) B:ACN (0.01% TFA), Column: SunFire C18 3.5 um, 4.6*50 mm; Oven Temperature: 50° C. All masses are reported as those of the protonated parent ions.

GCMS analysis was performed on a Hewlet Packard instrument (HP6890 Series gas chromatograph with a Mass Selective Detector 5973; injector volume: 1 µL; initial column temperature: 50° C.; final column temperature: 250 C; ramp time: 20 min; gas flow rate: 1 mL/min; column: 5% phenyl methyl siloxane, Model #HP 190915-443, dimensions: 30.0 m×25 m×0.25 m); or Agilent instrument (7890A Series gas chromatograph with a Mass Selective Detector 5975C; injector volume: 1 mL; initial column temperature: 40° C.; final column temperature: 250 C; ramp time: 8.4 min; gas flow rate: 1.2 mL/min; column: 5% phenyl methyl silox, Model:Agilent 19091s-433:325C, dimensions: 30.0 m'250u m'0.25 um).

Nuclear magnetic resonance (NMR) analysis was performed with a Varian 300 MHz NMR (Palo Alto, Calif.). and a Varian Unity Enova 400 MHz NMR spectrometer (Palo Alto, Calif.), or Bruker AVANCE III 400 MHz, UltraShield-Plus™ Digital NMR. The spectral reference was either TMS or the known chemical shift of the solvent. Some compound samples were run at elevated temperatures (e.g. 75° C.) to promote increased sample solubility.

Procedure 1 (C—C coupling reaction using CuCl-Cadiot): Hydroxylamine hydrochloride (0.23 mmol, 0.06 eq) and CuCl (0.08, 0.02 eq) were dissolved in 23% aqueous n-butylamine (1 mL) and the resulting solution was cooled to 0° C. A solution of the alkyne (4.3 mmol, 1.1 eq) in 23% aqueous n-butylamine (2 mL) was then added. The bromoalkyne (3.92 mmol) and hydroxylamine hydrochloride (0.23 mmol, 0.06 eq) were dissolved in 23% aqueous n-butylamine (2 mL) and THF (3 mL), and they were slowly added to the reaction mixture. The reaction was stirred for 1 hr, followed by quenching with EtOAc and water. The organic layer was separated and washed with brine, dried over $Na_2SO_4$, filtered and concentrated under reduced pressure to yield the desired coupled product.

Procedure 2 (Boc deprotection using TFA): To the Boc-protected compound (3.39 mmol) at 0° C. was added a TFA:DCM solution (9 mL, 2:1) and the reaction was stirred for 1 hr. The reaction was concentrated under reduced pressure to yield a crude residue, which was azeotroped with IPA twice to yield the desired deprotected product.

Procedure 3 (Hydroxamate formation): To a stirring solution of the ester (3.38 mmol) in IPA (4 mL) at 0° C. was slowly added 50% aqueous hydroxylamine (40 eq), and the reaction was stirred overnight. The reaction was quenched with AcOH (0.12 mol, 20 eq) or until the pH was 6. The volatiles were removed under reduced pressure, and the resulting solution was purified by RP HPLC.

Procedure 4A (formation of imine in reductive amination to NHMe): To a stirring solution of the amine (2.37 g, 7.20 mmol) in DMF (14.39 mL) was added DIPEA (1.88 mL, 10.79 mmol) followed by formaldehyde (37% in water) (1.07 mL, 14.39 mmol) and the reaction was stirred for 2 hr. The excess aldehyde was quenched with n-butylamine (30% in water) (2.63 g, 10.79 mmol) and stirred for 1 hr. The reaction mixture was diluted with water, and lyophilized to yield the desired imine.

Procedure 4B (reduction to amine in reductive amination to NHMe): To a stirring solution of the imine (3.96 g, 11.60 mmol) in THF (23.17 mL) and MeOH (2.439 mL) was added acetic acid (1.33 mL, 23.20 mmol) followed by sodium cyanoborohydride (10.94 g, 174 mmol) and the reaction was stirred for 1 hr. The reaction mixture was diluted with water (7 mL) and concentrated under reduced pressure to yield the amine.

4-(bromoethynyl) benzoic acid (INT-1)

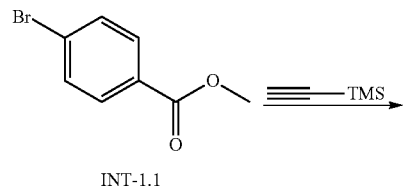

INT-1.1

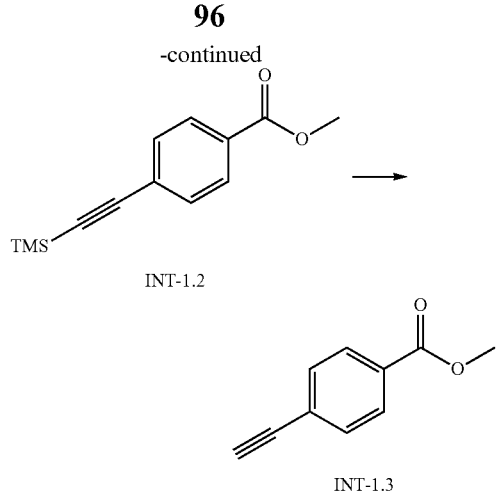

INT-1.2

INT-1.3

Ethynyltrimethylsilane (82.4 g, 0.84 mol) was added dropwise over 10 min under a nitrogen atmosphere to a solution of methyl 4-bromobenzoate (150 g, 0.7 mol), $PdCl_2(PPh_3)_2$ (15 g, 0.021 mol) and CuI (13 g, 0.07 mol) in TEA (1.5 L) and the reaction was stirred at 90° C. for 30 minutes. Solids were collected by filtration and washed with EtOAc (5×500 mL). The filtrate was concentrated under reduced pressure to give a residue, which was distilled under reduced pressure to yield methyl 4-((trimethylsilyl) ethynyl) benzoate (INT-1.2) as an off-white solid (156 g, 96%).

To a solution of methyl 4-((trimethylsilyl) ethynyl)benzoate (156 g, 0.67 mol) in methanol (800 mL) was added dropwise KOH/methanol (18 g/250 mL) keeping the temperature below 10° C. The reaction mixture was allowed to warm to room temperature for 5 min and was then neutralized with 2M HCl. Methyl 4-ethynylbenzoate (INT-1.3) was collected by filtration as a white solid (97 g, 90%). MS: m/z calcd for $C_{10}H_8O_2$ 160.0. found $[M+H]^+$ 161.

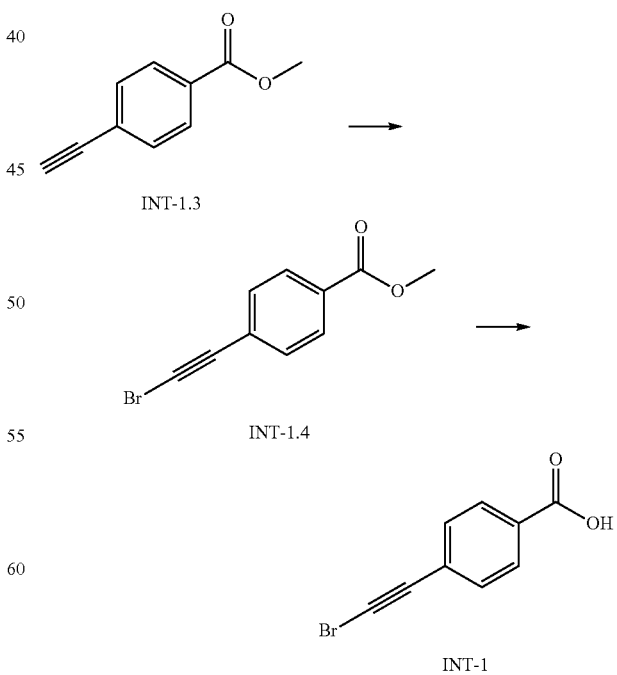

INT-1.3

INT-1.4

INT-1

To a solution of methyl 4-ethynylbenzoate (50 g, 0.31 mol) in acetone (750 mL) was added $AgNO_3$ (5 g, 29.7 mmol) and the reaction mixture was stirred for 1 hr. NBS (61.2 g, 0.34 mol) was added and the reaction mixture was stirred at room temperature for 20 hr, filtered and concentrated under reduced pressure. The residue was diluted in EA, and washed with iced 20% H$_2$SO$_4$. The organic layer was washed with water and brine, dried (Na$_2$SO$_4$), filtered, concentrated under reduced pressure to give a residue, which was recrystallized from MeOH (1 mL/4 g) to yield methyl 4-(bromoethynyl) benzoate (INT-1.4) as an off-yellow solid (67 g, 90%). $^1$H NMR (400 MHz, CDCl$_3$) δ 7.98 (d, J=8.8 Hz, 2H), 7.51 (d, J=8.8 Hz, 2H), 3.92 (s, 3H).

To a solution of methyl 4-(bromoethynyl) benzoate (67 g, 280 mmol) in CH$_3$OH/THF/H$_2$O=5/5/1 (1100 mL) was added NaOH (44.84 g) and the reaction mixture was stirred at 25° C. for 3 hr. The volatiles were removed under reduced pressure and the resulting solution was neutralized with 1N HCl to pH 3-5. Solids were collected by filtration, washed with water and dried at 50° C. for 5 hr to yield 4-(bromoethynyl) benzoic acid (INT-1) (61 g, 96%).

1. N-hydroxy-2-(4-(((trans)-2-(hydroxymethyl)cyclopropyl)buta-1,3-diynyl)phenyl)-1,6-naphthyridine-4-carboxamide (1)

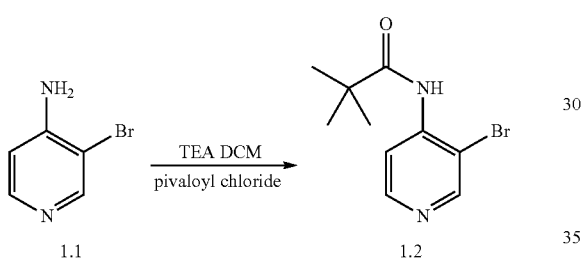

To a stirring solution of 4-amino-3-bromopyridine (1.1, 173 mg, 1 mmol) and Et$_3$N (132 mg, 1.3 mmol) in DCM (5 mL) was added dropwise pivaloyl chloride (133 mg, 1.1 mmol), and the reaction was stirred at room temperature for 3 hr. The mixture was washed with water (2×), NaHCO$_3$, brine, dried and concentrated under reduced pressure to give the product 1.2 as a solid. MS: m/z calcd for C$_{10}$H$_{13}$BrN$_2$O, 256.02/258.02. found [M+H]$^+$ 257/259.

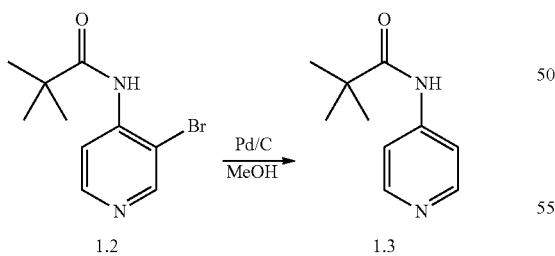

A mixture of compound 1.2 (5 g, 19.4 mmol) and 10% Pd/C (500 mg) in MeOH (70 mL) was stirred under H$_2$ (1 atm) at room temperature overnight. The Pd/C was removed by filtration and the solvent was concentrated under reduced pressure to yield a crude, which was dissolved in EtOAc. The organic layer was washed with NaHCO$_3$, brine, dried and concentrated under reduced pressure to give the product 1.3 as a solid. MS: m/z calcd for C$_{10}$H$_{14}$N$_2$O, 178.11. found [M+H]$^+$ 179.

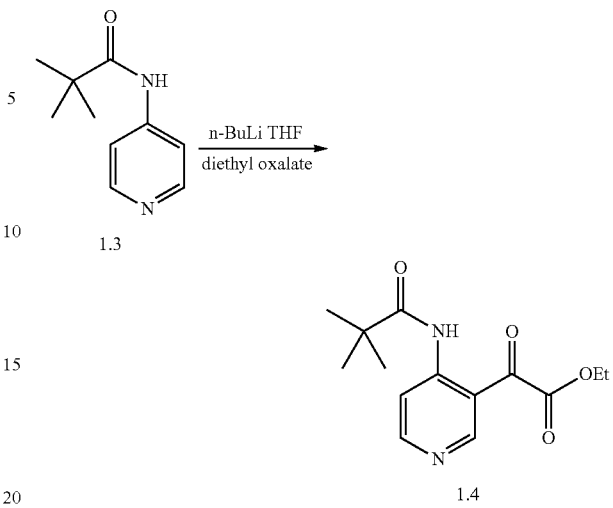

To a solution of compound 1.3 (5.34 g, 30 mmol) in THF (200 mL) at −78° C. was added dropwise n-BuLi (47 mL, 75 mmol) and the reaction was stirred for 3 hr at −10° C. The reaction was cooled to −78° C. and a solution of diethyl oxalate (22 g, 150 mmol) in THF (20 mL) was added dropwise and the mixture was stirred overnight at room temperature. NH$_4$Cl was added, and the reaction was extracted with EtOAc, washed with brine, dried, concentrated under reduced pressure and purified by flash chromatography (silica gel/EtOAc/PE 1:10-1:8) to give the product 1.4 as a solid. MS: m/z calcd for C$_{14}$H$_{18}$N$_2$O$_4$, 278.13. found [M+H]$^+$ 279.

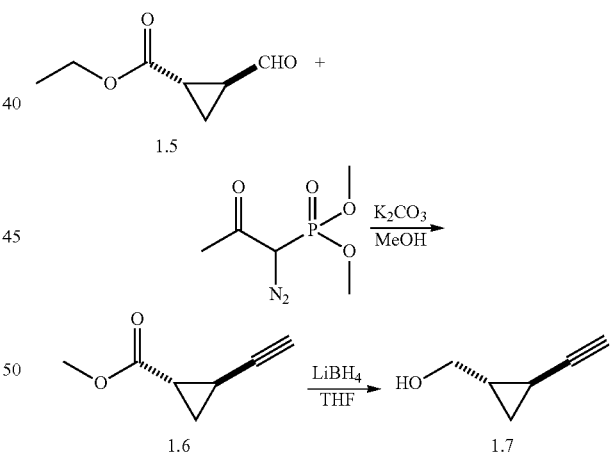

Compound 1.7 was synthesized according to the procedure described in International PCT Patent Application Publication No. WO2012/154204.

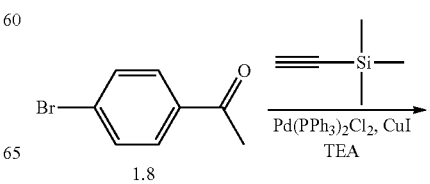

¹H NMR (400 MHz, DMSO-d₆) δ 7.95 (d, J=8, 2H), 7.62 (d, J=8, 2H), 4.49 (s, 1H), 2.59 (s, 3H).

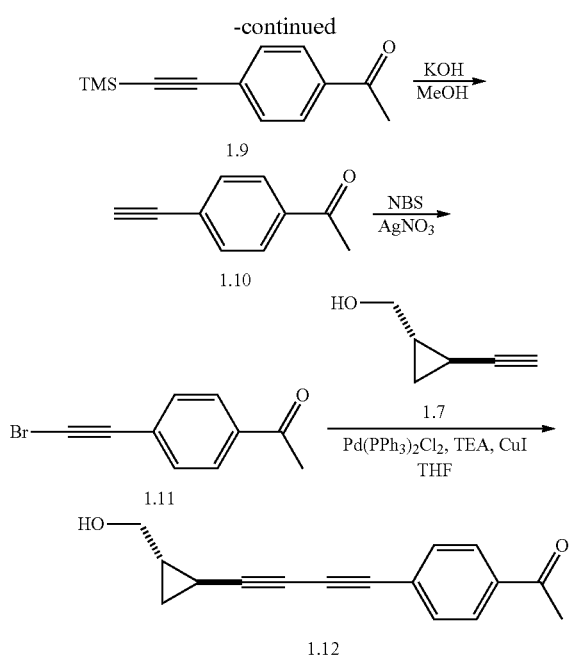

| 1-(4-(bromoethynyl)phenyl)ethanone (1.11) | | | | |
|---|---|---|---|---|
| Reagent | MW | Eq. | Mmol | g, mL |
| Compound 1.11 | 144 | 1.0 | 83.3 | 12 g |
| NBS | 177 | 1.2 | 99.96 | 17.7 g |
| AgNO₃ | 169 | 0.095 | 7.9 | 1.34 g |
| Acetone | | | | 200 mL |

To a stirring solution of compound 1.10 (12 g, 83.3 mmol) in acetone (200 mL) was added AgNO₃ (1.34 g, 7.9 mmol) and the the reaction was stirred for 30 min. NBS (17.7 g, 99.96 mmol) was then added and the reaction mixture was stirred at 20° C. for 14 hr. Solids were removed by filtration and the filtrate was concentrated under reduced pressure to give a crude, which was purified by flash chromatography (silica gel/ethyl acetate in petroleum ether 5%-10% v/v) to give compound 1.11 as a white solid (14 g, 76%). ¹H NMR (400 MHz, DMSO-d₆) δ 7.95 (d, J=8, 2H), 7.62 (d, J=8, 2H), 2.58 (s, 3H).

| 1-(4-(((trimethylsilyl)ethynyl)phenyl)ethanone (1.9) | | | | |
|---|---|---|---|---|
| Reagent | MW | Eq. | mmol | g, mL |
| Compound 1.8 | 198 | 1.0 | 101 | 20 g |
| ethynyl(trimethyl)silane | 98 | 1.4 | 141 | 13.8 g |
| Pd(PPh₃)₂Cl₂ | 701 | 0.05 | 5.1 | 3.6 g |
| CuI | 190 | 0.1 | 10 | 1.9 |
| TEA | | | | 300 mL |

To a stirring solution of compound 1.8 (20 g, 101 mmol), Pd(PPh₃)₂Cl₂ (3.6 g, 141 mmol), CuI (1.9 g, 10 mmol) in TEA (300 mL) under argon was added ethynyl(trimethyl)silane (13.8 g, 141 mmol) at 90° C. and the reaction mixture was stirred at 90° C. for 4 hr. The solids were removed by filtration, and rinsed with ethyl acetate (3×80 mL). The filtrate was concentrated under reduced pressure to give a crude, which was purified by flash chromatography (silica gel/ethyl acetate in petroleum ether 5%-10% v/v) to give compound 1.9 as a yellow oil (19 g, 90%). ¹H NMR (400 MHz, DMSO-d₆) δ 7.92 (d, J=8, 2H), 7.56 (d, J=8, 2H), 2.56 (s, 3H), 0.23 (s, 9H).

| 1-(4-ethynylphenyl)ethanone (1.10) | | | | |
|---|---|---|---|---|
| Reagent | MW | Eq. | mmol | g, mL |
| Compound 1.9 | 216 | 1.0 | 88 | 19 g |
| KOH | 56 | 0.5 | 44 | 2.46 g |
| MeOH | | | | 200 mL |

To a stirring solution of compound 1.9 (19 g, 88 mmol) in MeOH (200 mL) was added a solution of KOH (2.46 g, 44 mmol) in MeOH (20 mL) at 10° C. and the mixture was stirred at room temperature for 1 hr. AcOH was added until the pH was 7, and the reaction mixture was concentrated under reduced pressure. The residue was dissolved in ethyl acetate (200 mL), washed with 5% aqueous NaHCO₃ (100 mL), brine (100 mL), dried, and concentrated under reduced pressure to give compound 1.10 as a white solid (12 g, 95%).

| 1-(4-(((trans)-2-(hydroxymethyl)cyclopropyl)buta-1,3-diyn-1-yl)phenyl)ethanone (1.12) | | | | |
|---|---|---|---|---|
| Reagent | MW | Eq. | mmol | g, mL |
| Compound 1.11 | 198 | 1.0 | 4.5 | 1.0 g |
| Compound 1.7 | 96 | 1.5 | 6.75 | 648 mg |
| Pd(PPh₃)₂Cl₂ | 701 | 0.05 | 0.225 | 158 mg |
| CuI | 190 | 0.1 | 0.45 | 90 mg |
| TEA | 101 | 2 | 9 | 1.16 g |
| THF | | | | 30 mL |

To a stirring solution of compound 1.11 (1.0 g, 4.5 mmol), compound 1.7 (648 mg, 6.75 mmol), Pd(PPh₃)₂Cl₂ (158 mg, 0.22 mmol), and CuI (90 mg, 0.45 mmol) in THF (30 mL) under argon was added TEA (1.16 g, 9 mmol) and the mixture was stirred at 20° C. for 14 hr. Solids were removed by filtration and rinsed with ethyl acetate (3×80 mL), the filtrate was concentrated under reduced pressure to yield a crude, which was purified by flash chromatography (silica gel/ethyl acetate in petroleum ether 15%-50% v/v) to give compound 1.12 as a yellow solid (450 mg, 42%). MS: m/z calcd for C₁₆H₁₄O₂, 238.1. found [M+H]⁺ 239. ¹H NMR (400 MHz, CDCl₃) δ 7.89 (d, J=8.4, 2H), 7.53 (d, J=8.4, 2H), 3.61 (dd, J=6, 11.6, 1H), 3.51 (dd, J=6.8, 11.6, 1H), 2.59 (s, 3H), 1.57-1.62 (m, 1H), 1.49 (brs, 1H), 1.37-1.41 (m, 1H), 1.06-1.10 (m, 1H), 0.88-0.93 (m, 1H).

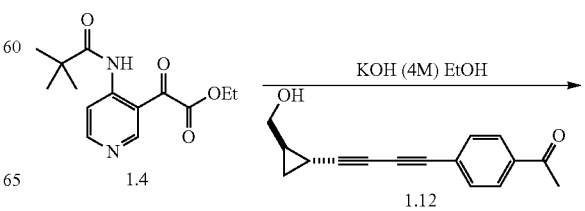

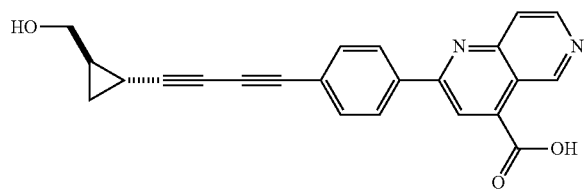

1.13

To a stirring solution of compound 1.4 (139 mg, 0.5 mmol) in EtOH (10 mL) was added KOH (112 mg, 2.0 mmol, 4M), and the reaction was heated at 100° C. for 3 hr. Racemic compound 1.12 (178.5 mg, 0.75 mmol) was added and the mixture was stirred overnight at 100° C. The solvent was concentrated under reduced pressure. Water was added, and the reaction was washed with Et$_2$O. The reaction mixture was adjusted to pH 1-2 with acetic acid, and the resulting solids were collected by filtration and dried to yield the desired product 1.13. MS: m/z calcd for $C_{23}H_{16}N_2O_3$, 68.12. found $[M+H]^+$ 369.

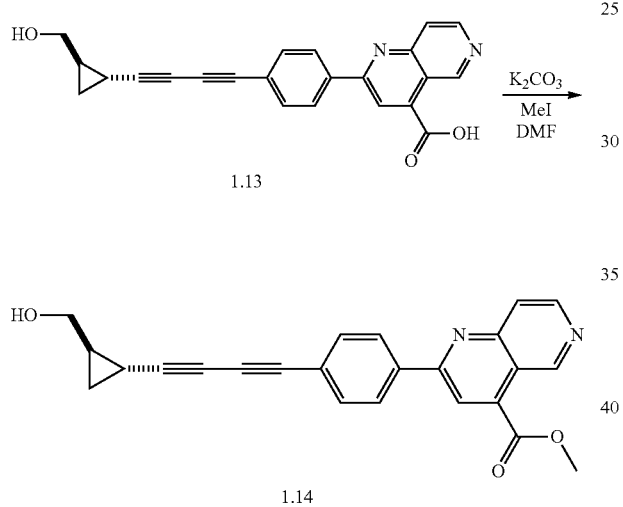

To a stirring solution of compound 1.13 (184 mg, 0.5 mmol) in DMF (10 mL) was added K$_2$CO$_3$ (138 mg, 1.0 mmol), followed by iodomethane (74.55 mg, 0.52 mmol) and the reaction was stirred overnight at room temperature. The reaction was quenched with water, extracted with EtOAc, washed with brine, dried, concentrated under reduced pressure to give a crude, which was purified by flash chromatography (silica gel/PE:EtOAc 1.5:1-1:1.5) to yield a solid, which was recrystallized from EA/PE (1:5) to give the desired product 1.14. MS: m/z calcd for $C_{24}H_{18}N_2O_3$, 382.13. found $[M+H]^+$ 383.

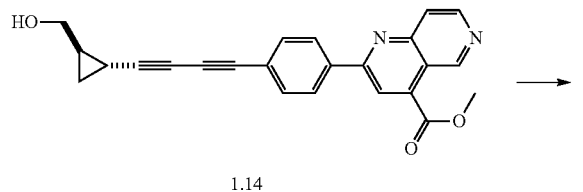

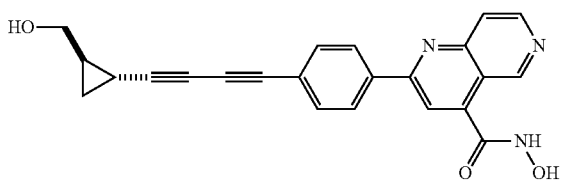

compound 1

Compound 1.14 (500 mg) was converted to N-hydroxy-2-(4-(((trans)-2-(hydroxymethyl)cyclopropyl)buta-1,3-diyn-1-yl)phenyl)-1,6-naphthyridine-4-carboxamide (1, 339 mg, 68%) using Procedure 3: MS: m/z calcd for $C_{23}H_{17}N_3O_3$, 383.13. found $[M+H]^+$ 384.

2. N-hydroxy-4-(4-(((trans)-2-(hydroxymethyl)cyclopropyl)buta-1,3-diynyl)phenyl)picolinamide (2)

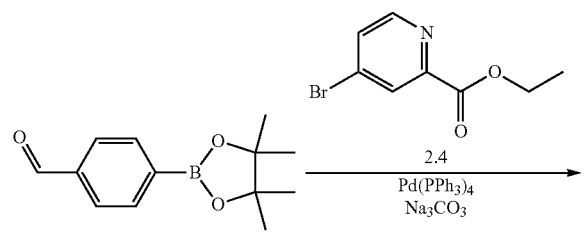

To a stirring solution of compound 2.1 (27.8 g, 0.15 mol), compound 2.2 (45.7 g, 0.18 mol) and PdCl$_2$(PPh$_3$)$_2$ (5.26 g, 7.5 mmol) in 1,4-dioxane (500 mL), was added KOAc (22.0 g, 0.225 mol) under an argon atmosphere and the mixture was stirred at 80° C. for 15 hr. The solvent was removed under reduced pressure, and the residue was diluted with PE (500 mL). Solids were removed by filtration, and the filtrate was concentrated under reduced pressure to give a crude, which was purified by flash chromatography (silica gel/PE: EA 10:1) to give 4-(4,4,5,5-tetramethyl-1,3,2-dioxaborolan-2-yl)benzaldehyde (2.3, 32.5 g, 95%) as a white solid.

-continued

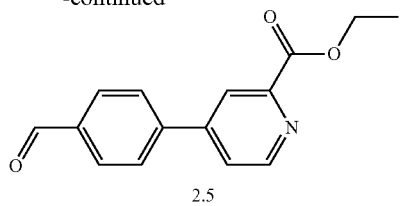

2.5

To a stirring solution of compound 2.3 (32.4 g, 0.14 mol), compound 2.4 (32.2 g, 0.17 mol) and Pd(PPh₃)₄ (8.08 g, 7 mmol) in 1,4-dioxane/methanol (800 mL, 1:1) was added Na₂CO₃ (22.3 g, 0.21 mol) under an argon atmosphere and the mixture was stirred at 80° C. for 15 hr. The solvent was removed under reduced pressure and the resulting residue was diluted with water (500 mL) and extracted with EtOAc (3×500 mL). The combined organic layers were dried and concentrated under reduced pressure to give a crude, which was purified by flash chromatography (silica gel/PE:EA 2:1) to give ethyl 4-(4-formylphenyl)picolinate (2.5, 14.2 g, 40%) as a yellow solid.

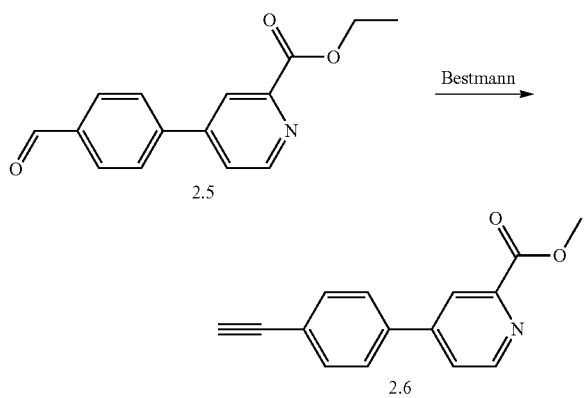

To a stirring solution of compound 2.5 (12.7 g, 50 mmol) in CH₃OH (300 mL) was added the Bestmann reagent (14.4 g, 75 mmol) followed by K₂CO₃ (20.8 g, 150 mmol) and the reaction was stirred for 5 hr. The reaction mixture was diluted with water (500 mL) and extracted with Et₂O (3×300 mL). The combined organic layers were dried and concentrated under reduced pressure to give a crude, which was purified by flash chromatography (silica gel/PE:Et₂O 10:1-5:1) to give methyl 4-(4-ethynylphenyl)picolinate (2.6, 4.0 g, 33.9%) as a white solid.

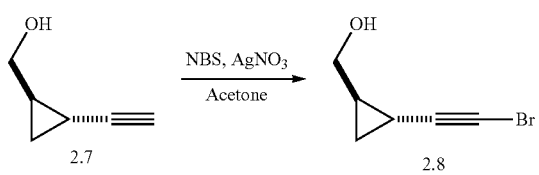

To a stirring solution of racemic compound 2.7 (4.8 g, 50 mmol) and AgNO₃ (0.85 g, 5 mmol) in acetone (200 mL) was added NBS (10.7 g, 60 mmol) under an argon atmosphere and the mixture was stirred at room temperature for 15 hr. The mixture was filtered and the residue was taken up with acetone, the combined organic layers were concentrated under reduced pressure to give a crude, which was purified by flash chromatography (silica gel/PE:EA 5:1) to give (2-trans-(bromoethynyl)cyclopropyl)methanol (2.8, 5.2 g, 60%) as a colorless oil.

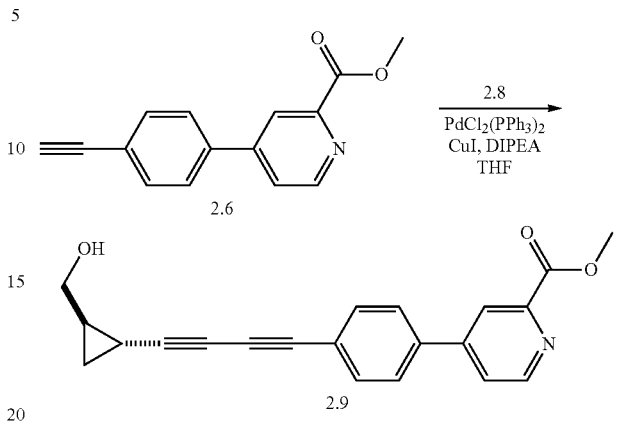

To a stirring solution of compound 2.6 (1.77 g, 7.5 mmol), Pd(PPh₃)₂Cl₂ (262 mg, 0.37 mmol), CuI (143 mg, 0.75 mmol), and DIPEA (2.9 g, 22.5 mmol) in THF (50 mL) was added compound 2.8 (1.84 g, 10.5 mmol) under an argon atmosphere, and the mixture was stirred at room temperature for 5 hr. The solvent was removed under reduced pressure, and the resulting residue was diluted with water (100 mL) and extracted with EtOAc (3×150 mL). The combined organic layers were dried and concentrated under reduced pressure to give a red oil, which was purified by flash chromatography (silica gel/PE:EA 5:1~3:1) to yield methyl 4-(4-(((trans)-2-(hydroxymethyl)cyclopropyl)buta-1,3-diyn-1-yl)phenyl)picolinate (2.9, 570 mg, 23%): MS: m/z calcd for $C_{21}H_{17}NO_3$, 331.12. found [M+H]⁺ 332; ¹H-NMR (DMSO-d₆, 400 MHz) δ 8.77 (d, J=5.6 Hz, 1H), 8.30 (s, 1H), 7.99 (d, J=5.6 Hz, 1H), 7.90 (d, J=8.4 Hz, 2H), 7.67 (d, J=8.4 Hz, 2H), 4.72 (t, J=5.6 Hz, 1H), 3.91 (s, 3H), 3.44 (m, 1H), 3.24 (m, 1H), 1.45 (m, 2H), 0.88 (m, 2H).

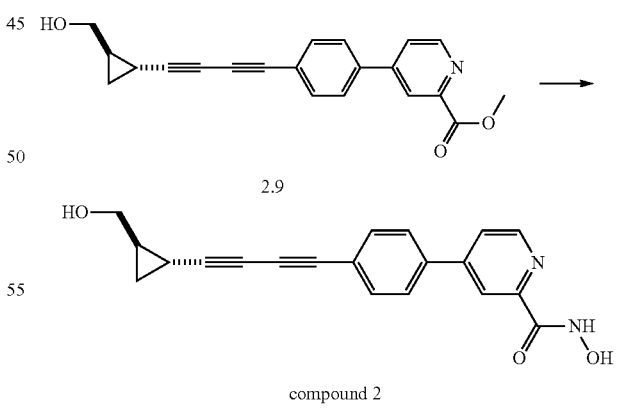

Methyl 4-(4-(((trans)-2-(hydroxymethyl)cyclopropyl)buta-1,3-diyn-1-yl)phenyl)picolinate (2.9, 500 mg) was treated according to Procedure 3 to give N-hydroxy-4-(4-(((trans)-2-(hydroxymethyl)cyclopropyl)buta-1,3-diyn-1-yl)phenyl)picolinamide (2, 157 mg, 31%). MS: m/z calcd for $C_{20}H_{16}N_2O_3$, 332.12. found [M+H]⁺ 333.1.

3. N—((R)-1-(hydroxyamino)-3-methyl-3-(methylthio)-1-oxobutan-2-yl)-4-(((trans)-2-(hydroxymethyl)cyclopropyl)buta-1,3-diynyl)benzamide (3)

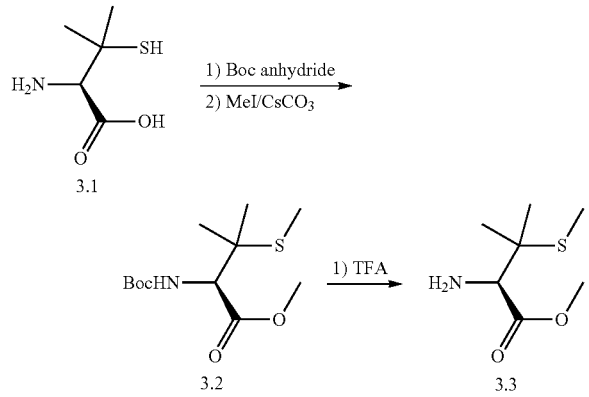

To a stirring suspension of (R)-2-amino-3-mercapto-3-methylbutanoic acid (3.1, 9 g, 60.3 mmol) in DMF (20 mL) was added BOC-anhydride (14.0 mL, 60.3 mmol) followed by TEA (8.41 mL, 63.3 mmol) and the reaction mixture was stirred for 18 hr. Excess solvent was removed under reduced pressure. The crude product was treated with methyl iodide (18.83 g, 133 mmol) in DMF (20 mL) and Cs$_2$CO$_3$ (43.2 g, 133 mmol) at room temperature for 18 hr. Water (100 mL) was added and the product was extracted with ethyl acetate (2×200 mL), dried (Na$_2$SO$_4$) and concentrated under reduced pressure to give compound 3.2 (12.62 g) as a white solid. Subsequent BOC deprotection was achieved by treatment with TFA (20 mL) in CH$_2$Cl$_2$ (20 mL) for 5 hr. The solvent was removed under reduced pressure to give the desired product 3.3 (8.2 g).

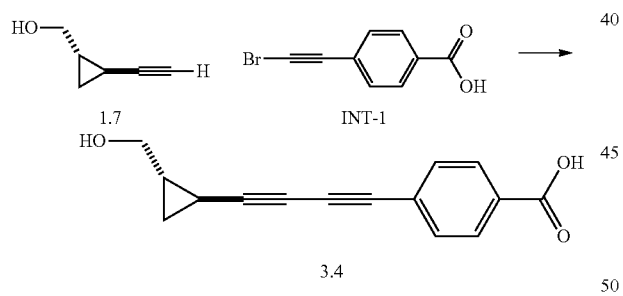

A stirring solution of racemic ((trans)-2-ethynylcyclopropyl)methanol (1.7, 11 g, 106 mmol), copper(I) chloride (0.20 g, 2.03 mmol), and hydroxylamine hydrochloride (0.42 g, 6.08 mmol) in 30% aqueous butylamine (156 mL) was poured into a 1 L jacketed reactor and cooled to 0° C. A solution of 4-(bromoethynyl)benzoic acid (INT-1, 22.81 g, 101 mmol) and hydroxylamine hydrochloride (0.42 g, 6.08 mmol) in 30% aqueous butylamine (111 mL) was then added dropwise and the reaction was stirred for 2 hr. The reaction mixture was washed with MTBE (2×230 mL) and the aqueous layer was diluted with methyl THF (460 mL). The solution was cooled to 0° C. and acidified by dropwise addition of 6M HCl (100 mL) to pH 1. The reaction mixture was filtered through Celite, and washed with methyl-THF (230 ml). The two layers were partitioned and the aqueous layer was back-extracted with methyl-THF (230 mL). The organic layers were washed with 2M HCl (2×230 mL), water (230 ml), and brine (230 ml), dried over Na$_2$SO$_4$ and filtered. The organic layer was concentrated under reduced pressure until the solution turned cloudy, then heptane (230 mL) was added. The resulting solution was concentrated under reduced pressure to 5 volumes and then additional heptane (230 mL) was added. The resulting solution was concentrated to 5 volumes to give a slurry. The solids were collected by filtration, washed with heptane (50 mL), and dried under reduced pressure to yield 4-(((trans)-2-(hydroxymethyl)cyclopropyl)buta-1,3-diyn-1-yl)benzoic acid (3.4, 3.96 g). MS: m/z calcd for C$_{16}$H$_{12}$O$_3$, 240.08. found [M−H]$^+$239.1. $^1$H NMR (DMSO-d$_6$, 400 MHz) δ 13.18 (s, 1H), 7.85 (d, 2H), 7.61 (d, 2H), 4.72 (t, 1H), 3.39-3.52 (m, 1H), 3.21-3.32 (m, 1H), 1.41-1.51 (m, 2H), 0.81-0.99 (m, 2H).

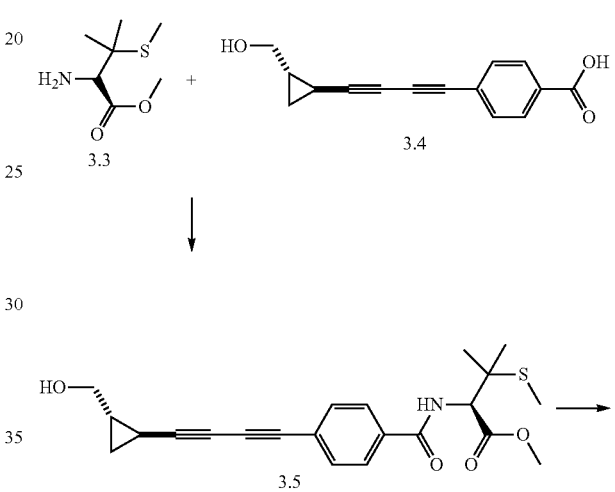

compound 3

To a stirring solution of triethylamine (1.06 g, 10.52 mmol), and (R)-methyl 2-amino-3-methyl-3-(methylthio)butanoate (3.3, 1.86 g, 10.52 mmol) was added a solution of racemic 4-(((trans)-2-(hydroxymethyl)cyclopropyl)buta-1,3-diyn-1-yl)benzoic acid (3.4, 2.5 g, 10.52 mmol) in DMF (40 mL), followed by 2-(3H-[1,2,3]triazolo[4,5-b]pyridin-3-yl)-1,1,3,3-tetramethylisouronium hexafluorophosphate (V) (4 g, 10.52 mmol) and the reaction was stirred for 2 hr. Water (100 mL) was added and the mixture was extracted with ethyl acetate (2×100 mL), dried (Na$_2$SO$_4$) and concentrated under reduced pressure to yield a crude, which was purified by flash chromatography (silica gel/ethyl acetate 10-40% in hexanes) to yield the corresponding ester 3.5 (2.6 g), which was converted to N—((R)-1-(hydroxyamino)-3-methyl-3-(methylthio)-1-oxobutan-2-yl)-4-(((trans)-2-(hydroxymethyl)cyclopropyl)buta-1,3-diyn-1-yl)benzamide (3) using Procedure 3. MS: m/z calcd for C$_{21}$H$_{24}$N$_2$O$_4$S, 400.15. found [M+H]$^+$ 401.

4. N-((2R)-1-(hydroxyamino)-3-methyl-3-(methyl-sulfinyl)-1-oxobutan-2-yl)-4-(((trans)-2-(hydroxymethyl)cyclopropyl)buta-1,3-diynyl)benzamide (4)

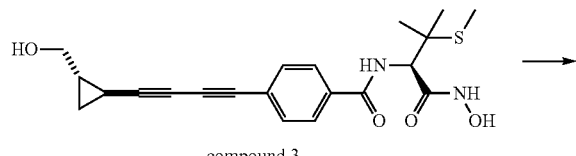
compound 3

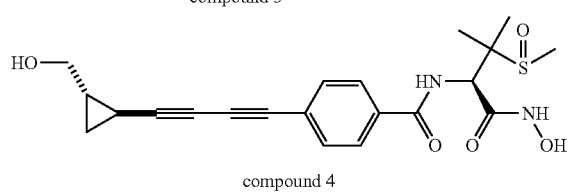
compound 4

To a stirring solution of N—((R)-1-(hydroxyamino)-3-methyl-3-(methylthio)-1-oxobutan-2-yl)-4-(((trans)-2-(hydroxymethyl)cyclopropyl)buta-1,3-diyn-1-yl)benzamide (3, 0.2 g, 0.50 mmol) in acetonitrile/water (20 mL) was added 30% aqueous hydrogen peroxide (0.015 mL, 0.50 mmol) and the reaction mixture was stirred at room temperature for 18 hr. The reaction mixture was lyophylized to afford N-((2R)-1-(hydroxyamino)-3-methyl-3-(methylsulfinyl)-1-oxobutan-2-yl)-4-(((trans)-2-(hydroxymethyl)cyclopropyl)buta-1,3-diyn-1-yl)benzamide (4, 200 mg, 449 mmol, 90%). MS: m/z calcd for $C_{21}H_{24}N_2O_5S$, 416.14. found $[M+H]^+$ 417.

5. N—((R)-1-(hydroxyamino)-3-methyl-3-(methyl-sulfonyl)-1-oxobutan-2-yl)-4-(((trans)-2-(hydroxym-ethyl)cyclopropyl)buta-1,3-diynyl)benzamide (5)

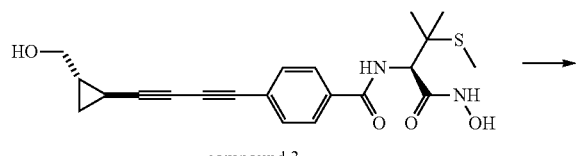
compound 3

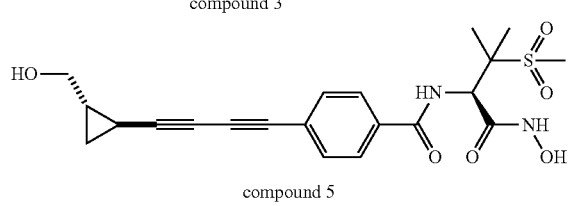
compound 5

N—((R)-1-(hydroxyamino)-3-methyl-3-(methylthio)-1-oxobutan-2-yl)-4-(((trans)-2-(hydroxymethyl)cyclopropyl)buta-1,3-diyn-1-yl)benzamide (3, 120 mg, 0.3 mmol) in 22% acetonitrile-water (100 mL) was treated with 30% peracetic acid (1 mL) overnight at room temperature. The reaction was lyophilized to afford N—((R)-1-(hydroxyamino)-3-methyl-3-(methylsulfonyl)-1-oxobutan-2-yl)-4-(((trans)-2-(hydroxymethyl)cyclopropyl)buta-1,3-diyn-1-yl)benzamide (5, 130 mg). MS: m/z calcd for $C_{21}H_{24}N_2O_6S$, 432.14. found $[M+H]^+$ 433.

6. N—((S)-3-amino-1-(hydroxyamino)-3-methyl-1-oxobutan-2-yl)-6-(((trans)-2-(hydroxymethyl)cyclo-propyl)ethynyl)-2-naphthamide (6)

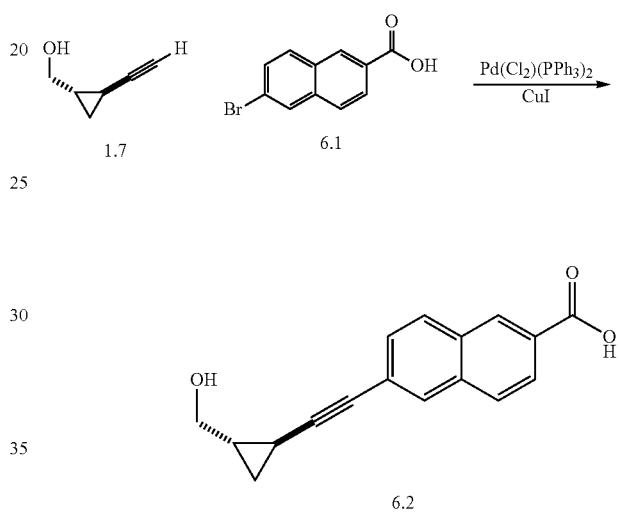

To a stirring solution of 6-bromo-2-naphthoic acid (6.1, 1.0 g, 4.0 mmol), racemic ((trans)-2-ethynylcyclopropyl) methanol (1.7, 0.5 g, 5.2 mmol), copper(I) iodide (30 mg, 0.16 mmol) and palladium(II) bis(triphenylphosphine) dichloride (56 mg, 0.08 mmol) in tetrahydrofuran (7.5 mL) under a nitrogen atmosphere was added triethylamine (2.5 mL) and the reaction was stirred for 1 week. The reaction was partitioned between 2N aqueous sodium hydroxide and ethyl acetate. The aqueous layer was acidified with conc HCl and extracted with ethyl acetate. The organic layer was washed with water, saturated sodium chloride and dried over magnesium sulfate, filtered and concentrated under reduced pressure to give 6-(((trans)-2-(hydroxymethyl)cyclopropyl)ethynyl)-2-naphthoic acid (6.2, 1.0 g, 94%).

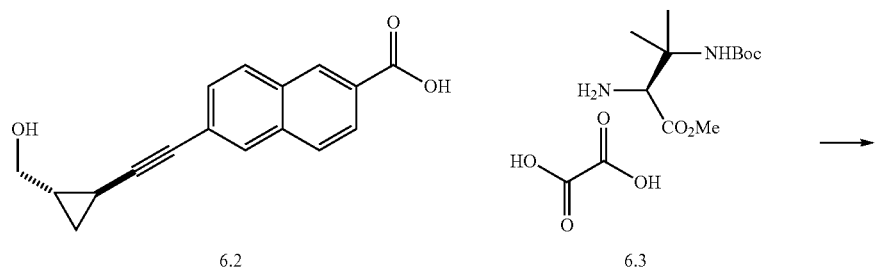

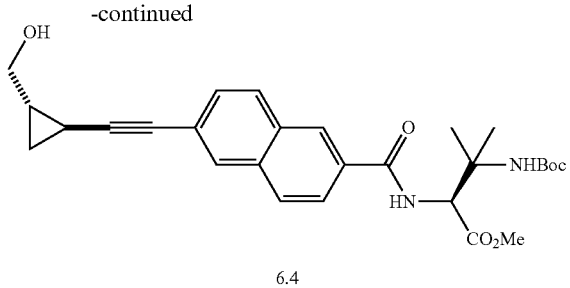

6.4

To a stirring suspension of (S)-methyl-2-amino-3-((tert-butoxycarbonyl)amino)-3-methylbutanoate oxalate (6.3, 1.6 g, 4.9 mmol) and 6-(((trans)-2-(hydroxymethyl)cyclopropyl)ethynyl)-2-naphthoic acid (6.2, 1.0 g, 3.8 mmol) in ACN (10 mL) at 0° C. was added triethylamine (2.1 mL, 15 mmol), followed by the portionwise addition of a solution of HATU (3.0 g, 7.9 mmol) in ACN (10 mL) and the reaction mixture was stirred at 0° C. for 75 min. The reaction was concentrated under reduced pressure to yield a residue, which was partitioned between MTBE and water. The organic layer was washed with 1M citric acid, water, saturated sodium bicarbonate (2×), saturated sodium chloride, dried over magnesium sulfate, filtered and concentrated under reduced pressure to give (S)-methyl 3-((tert-butoxycarbonyl)amino)-2-(6-(((trans)-2-(hydroxymethyl)cyclopropyl)ethynyl)-2-naphthamido)-3-methylbutanoate (6.4), which was carried through to the next step without further purification.

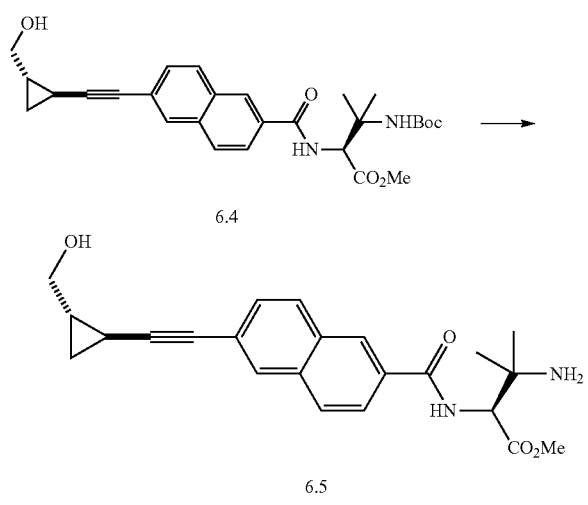

6.4

6.5

To a stirring solution of (S)-methyl 3-((tert-butoxycarbonyl)amino)-2-(6-(((trans)-2-(hydroxymethyl)cyclopropyl)ethynyl)-2-naphthamido)-3-methylbutanoate (6.4) in methanol (10 mL) was added 4N HCl in dioxane (10 mL) and the reaction mixture was stirred at rt for 2 hr, then at 4° C. overnight. The mixture was concentrated under reduced pressure to give a residue, which was partitioned between water and MTBE. The aqueous layer was basified with saturated sodium bicarbonate and extracted with ethyl acetate. The organic layer was washed with saturated sodium chloride, dried over magnesium sulfate, filtered and concentrated under reduced pressure to give (S)-methyl 3-amino-2-(6-(((trans)-2-(hydroxymethyl)cyclopropyl)ethynyl)-2-naphthamido)-3-methylbutanoate (6.5, 1.2 g, 3.0 mmol, 79%).

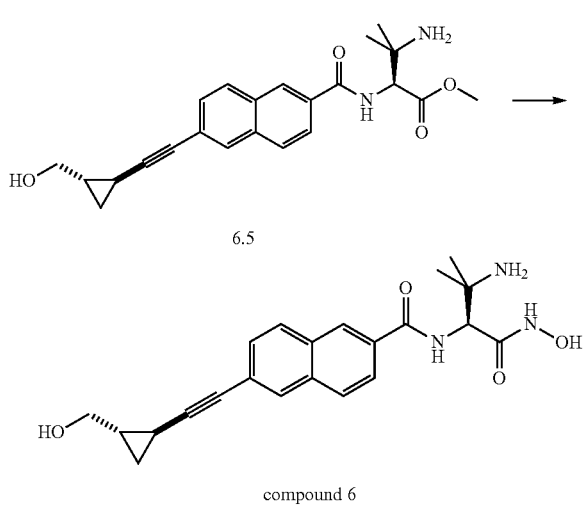

6.5 compound 6

Compound 6.5 (1.2 g) was treated according to Procedure 3 to yield the desired compound N—((S)-3-amino-1-(hydroxyamino)-3-methyl-1-oxobutan-2-yl)-6-(((trans)-2-(hydroxymethyl)cyclopropyl)ethynyl)-2-naphthamide (6, 400 mg, 1.01 mmol, 33.3% yield). MS: m/z calcd for $C_{22}H_{25}N_3O_4$, 395.18. found $[M+H]^+$ 396.2.

7. N—((S)-3-amino-1-(hydroxyamino)-3-methyl-1-oxobutan-2-yl)-6-(((trans)-2-(hydroxymethyl)cyclopropyl)ethynyl)benzo[b]thiophene-2-carboxamide (7)

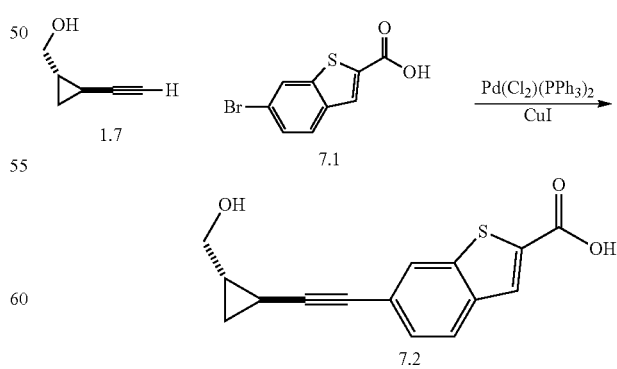

1.7

7.1

7.2

To a stirring solution of 6-bromobenzo[b]thiophene-2-carboxylic acid (7.1, 1.0 g, 3.9 mmol) in DMF (7.5 mL) under a nitrogen atmosphere were added racemic ((trans)-

2-ethynylcyclopropyl)methanol (1.7, 935 mg, 9.7 mmol), copper(I) iodide (30 mg, 0.16 mmol) and palladium(II) bis(triphenylphosphine) dichloride (56 mg, 0.08 mmol), followed by triethylamine (2.5 mL) and the reaction was stirred at room temperature for 1 hr, and then at 40° C. for 20 hr. The reaction mixture was partitioned between 2N aqueous sodium hydroxide and ethyl acetate. The aqueous layer was acidified with conc HCl and extracted with ethyl acetate. The resulting organic layer was washed with water, saturated sodium chloride, dried over magnesium sulfate, filtered and concentrated under reduced pressure to give 6-(((trans)-2-(hydroxymethyl)cyclopropyl)ethynyl)benzo[b]thiophene-2-carboxylic acid (7.2, 900 mg, 3.3 mmol, 85%).

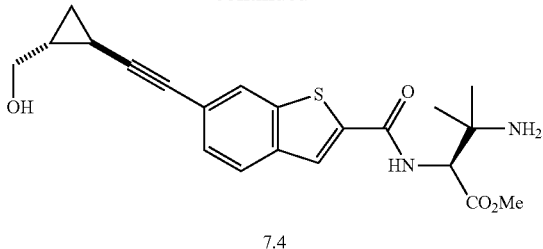

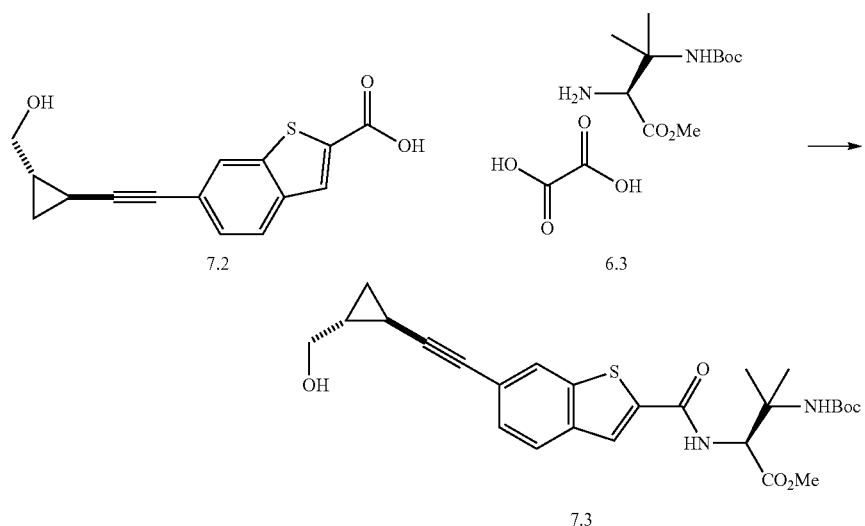

To a stirring solution of (S)-methyl 2-amino-3-((tert-butoxycarbonyl)amino)-3-methylbutanoate oxalate 6.3 (1.4 g, 4.3 mmol), 6-(((trans)-2-(hydroxymethyl)cyclopropyl)ethynyl)benzo[b]thiophene-2-carboxylic acid (7.2, 900 mg, 3.3 mmol) in ACN (10 mL) at 0° C. was added triethylamine (1.8 mL, 13 mmol), followed by the portionwise addition of a suspension of HATU (2.6 g, 6.9 mmol) in ACN (10 mL), and the reaction mixture was stirred at 0° C. for 105 min. The reaction mixture was concentrated under reduced pressure, and the residue was partitioned between MTBE and water. The organic layer was washed with 1M citric acid, water, saturated sodium bicarbonate (2×), saturated sodium chloride, dried over magnesium sulfate, filtered and concentrated under reduced pressure to give (S)-methyl 3-((tert-butoxycarbonyl)amino)-2-(6-(((trans)-2-(hydroxymethyl)cyclopropyl)ethynyl)benzo[b]thiophene-2-carboxamido)-3-methylbutanoate (7.3), which was carried through to the next step without further purification.

To a stirring solution of (S)-methyl 3-((tert-butoxycarbonyl)amino)-2-(6-(((trans)-2-(hydroxymethyl)cyclopropyl)ethynyl)benzo[b]thiophene-2-carboxamido)-3-methylbutanoate (7.3) in methanol (10 mL) was added 4N HCl in dioxane (10 mL) and the reaction was stirred at room temperature for 2 hr, then at 4° C. overnight. The reaction mixture was concentrated under reduced pressure to yield a residue, which was partitioned between water and MTBE. The aqueous layer was basified with saturated sodium bicarbonate and extracted with ethyl acetate. The organic layer was washed with saturated sodium chloride, dried over magnesium sulfate, filtered and concentrated under reduced pressure to give (S)-methyl 3-amino-2-(6-(((trans)-2-(hydroxymethyl)cyclopropyl)ethynyl)benzo[b]thiophene-2-carboxamido)-3-methylbutanoate (7.4, 880 mg, 2.2 mmol, 67%).

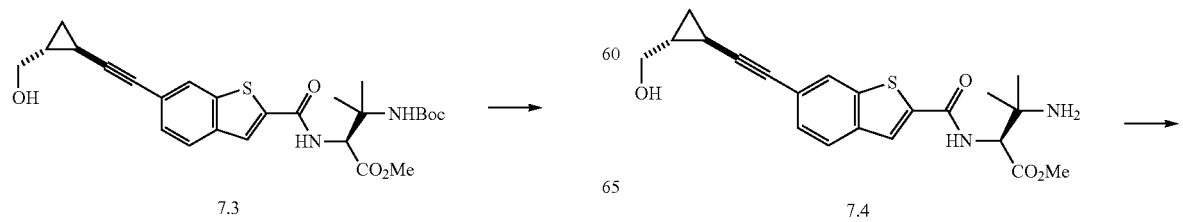

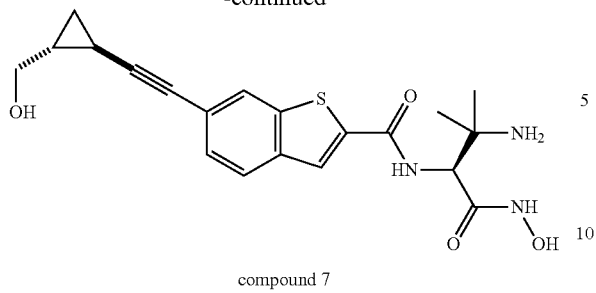

compound 7

Compound 7.4 (0.88 g) was treated according to Procedure 3 to yield the desired compound N—((S)-3-amino-1-(hydroxyamino)-3-methyl-1-oxobutan-2-yl)-6-(((trans)-2-(hydroxymethyl)cyclopropyl)ethynyl)benzo[b]thiophene-2-carboxamide (7, 16.3 mg, 0.041 mmol, 1.85% yield). MS: m/z calcd for $C_{20}H_{23}N_3O_4S$, 401.14. found $[M+H]^+$ 402.2.

8. N1-hydroxy-2-(4-(((1R,2R)-2-(hydroxymethyl)cyclopropyl)buta-1,3-diynyl)benzamido)-N3-methylmalonamide (8)

To a stirring solution of diethyl 2-((tert-butoxycarbonyl)amino)malonate (8.1, 0.93 mL, 3.63 mmol) in methanol (10 mL) was added 40% methanamine in water (0.32 mL, 3.63 mmol) and the reaction was stirred at room temperature for 27 days. The reaction was concentrated under reduced pressure to give an oil, which was purified by flash chromatography (silica gel/10% MeOH/DCM) to provide compound 8.2 (592 mg, 66.2% yield). MS: m/z calcd for $C_{10}H_{18}N_2O_5$, 246.12. found $[M+Na]^+$ 269.1.

Compound 8.2 (0.59 g, 2.40 mmol) was dissolved in DCM (3 mL) and TFA (3 mL) and the reaction was stirred for 30 min. The reaction mixture was concentrated under reduced pressure to give compound 8.3 (0.88 g), which was carried through to the next step without further purification. MS: m/z calcd for $C_5H_{10}N_2O_3$, 146.07. found $[M+H]^+$ 147.1.

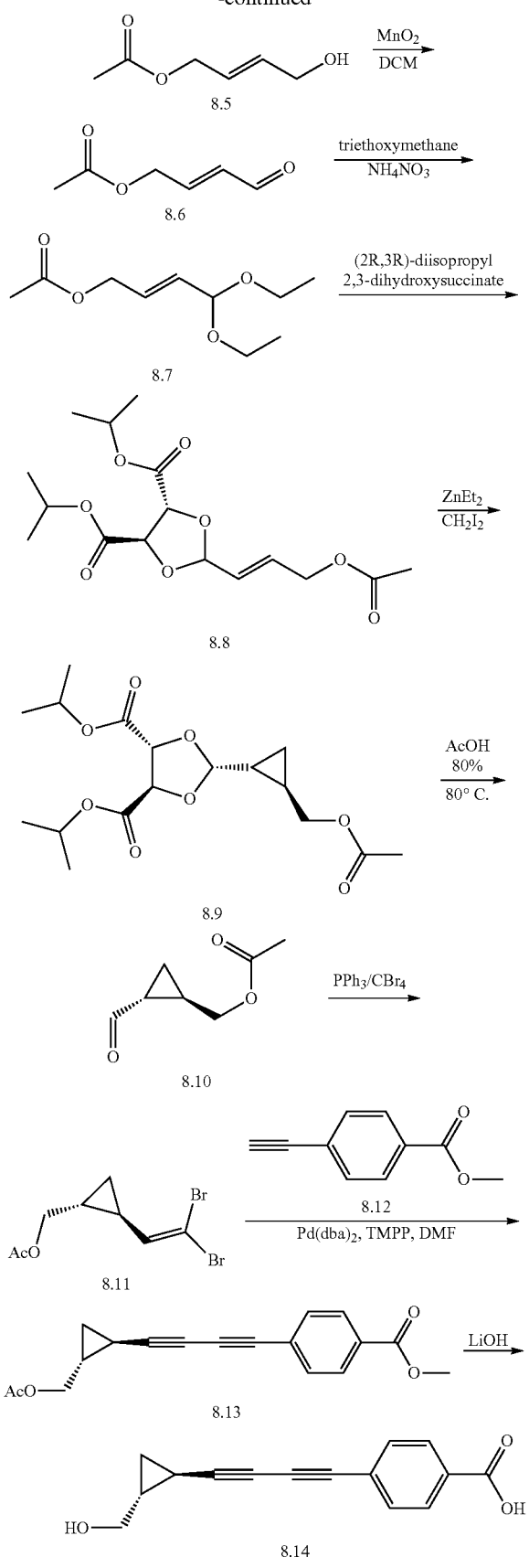

The synthesis of compound 8.14 was carried out as described in International PCT Patent Application Publication No. WO2012/154204.

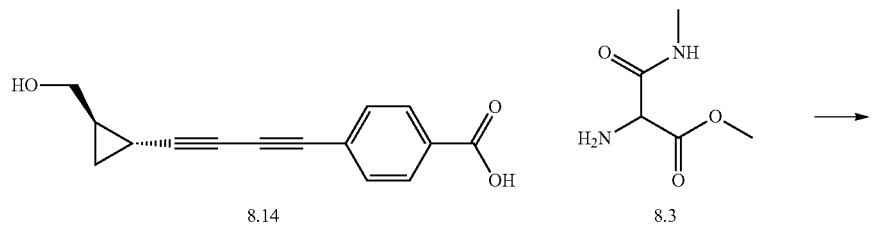

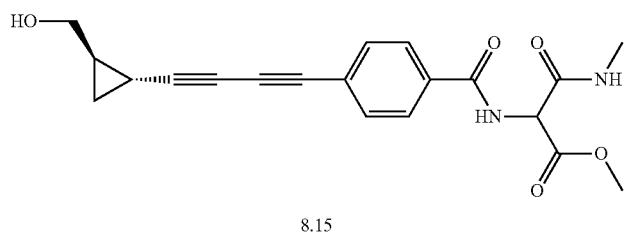

To a stirring solution of compound 8.3 (375 mg, 1.44 mmol) in ACN (3 mL) was added compound 8.14 (315 mg, 1.31 mmol), followed by DIPEA (1.01 mL, 5.77 mmol) and the reaction mixture was cooled to 0° C. HATU (548 mg, 1.44 mmol) was added and the reaction was allowed to warm to room temperature. After 1 hr solids were collected by filtration, and washed with ACN to yield compound 8.15 (200 mg, 41.4% yield). MS: m/z calcd for $C_{20}H_{20}N_2O_5$, 368.14. found [M+H]$^+$ 369.1.

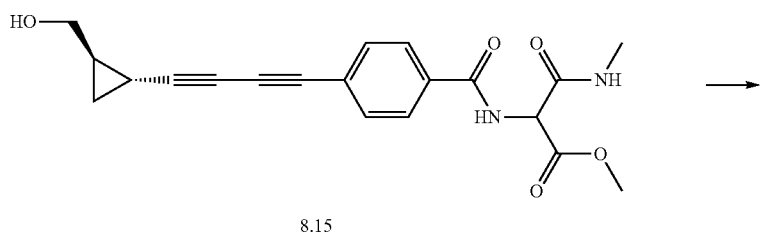

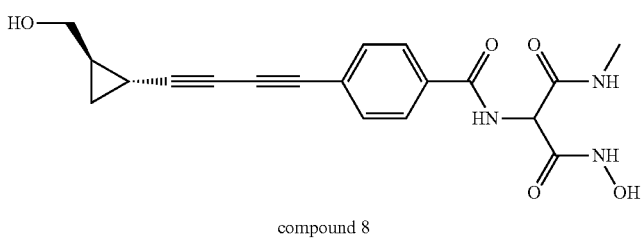

compound 8

To a stirring solution of compound 8.15 (200 mg, 0.54 mmol) in THF (1.0 mL) and methanol (1 mL) was added dropwise over 1 min a solution of 50% hydroxamic acid in water (1 mL) and the reaction was stirred at room temperature for 3 hr. The reaction mixture was concentrated under reduced pressure to give a crude, which was purified by RP HPLC (0.1% AcOH in water and ACN) to give N1-hydroxy-2-(4-(((1R,2R)-2-(hydroxymethyl)cyclopropyl)buta-1,3-diynyl)benzamido)-N3-methylmalonamide (8, 47.7 mg, 23.8% yield). MS: m/z calcd for $C_{19}H_{19}N_3O_6$ 369.13. found [M+H]$^+$ 370.1. $^1$H NMR (DMSO-d$_6$, 400 MHz) δ 10.84 (br, 1H), 9.06 (s, 1H), 8.57 (d, 1H), 8.02 (d, 1H), 7.89 (d, 2H), 7.60 (d, 2H), 4.99 (d, 1H), 4.70 (t, 1H), 3.43-3.37 (m, 1H), 3.29-3.22 (m, 1H), 2.60 (d, 3H), 1.46-1.41 (m, 2H), 0.94-0.86 (m, 2H).

9. N-hydroxy-4-(4-(((trans)-2-(hydroxymethyl)cyclopropyl)buta-1,3-diynyl)phenyl)-2-methyl-2-(methylsulfonyl)butanamide (9)

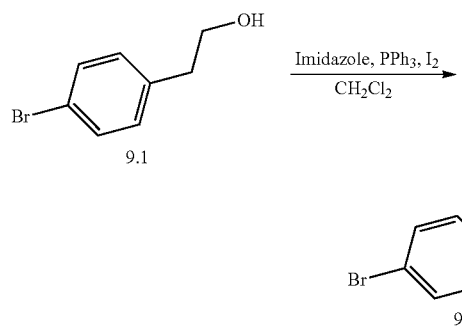

A solution of 2-(4-bromophenyl)ethanol (20.0 g, 100 mol) in CH$_2$Cl$_2$ (10 mL) was added dropwise to a solution of imidazole (22.4 mg, 0.33 mmol), PPh$_3$ (33.3 g, 127 mmol), and I$_2$ (32.5 g, 130 mmol) in CH$_2$Cl$_2$ (50 mL) at 0° C., and the reaction was warmed to room temperature and stirred overnight. The reaction mixture was washed with saturated aqueous sodium thiosulfate (2×50 mL), brine, dried over Na$_2$SO4, filtered and concentrated under reduced pressure to give a crude, which was purified by flash chromatography (silica gel/PE) to yield 1-bromo-4-(2-iodoethyl)benzene (9.2, 22.7 g, 73%) as a white solid. $^1$H NMR (400 MHz, CDCl$_3$) δ 3.13 (t, J=7.6 Hz, 2H), 3.32 (t, J=7.6 Hz, 2H), 7.07 (d, J=8.0 Hz, 2H), 7.44 (d, J=8.2 Hz, 2H).

Methyl 4-(4-bromophenyl)-2-methyl-2-(methylsulfonyl)butanoate

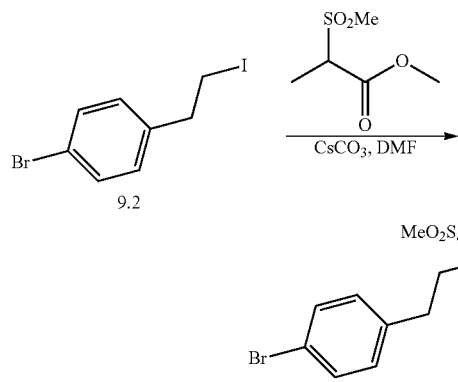

Compound 9.3 was synthesized according to the procedure described in WO 2011045703.

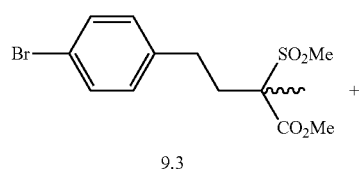

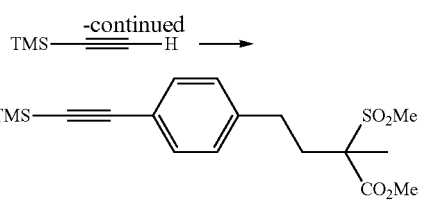

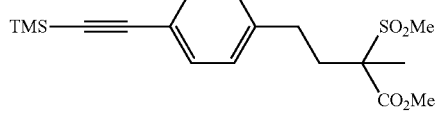

To a stirring suspension of methyl 4-(4-bromophenyl)-2-methyl-2-(methylsulfonyl)butanoate (9.3, 6.36 g, 18.23 mmol), bis(triphenylphosphine)palladium(II) chloride (1.28 mg, 1.82 mmol) and copper(I) iodide (347 mg, 1.82 mmol) in triethylamine (30 mL) was added ethynyltrimethylsilane (0.92 mL, 6.49 mmol) and the reaction mixture was heated to 80° C. briefly, and then allowed to stir at room temperature for 18 hr. Volatiles were removed under reduced pressure and the resulting residue was purified by flash chromatography (silica gel/15-50% EtOAc/hexanes) to yield methyl 2-methyl-2-(methylsulfonyl)-4-(4-((trimethylsilyl)ethynyl)phenyl)butanoate (9.4, 4.0 g, 59.9% yield). MS: m/z calcd for C$_{18}$H$_{26}$O$_4$SSi, 366.13. found [M+H]$^+$ 367.2.

To a stirring solution of methyl 2-methyl-2-(methylsulfonyl)-4-(4-((trimethylsilyl)ethynyl)phenyl)butanoate (9.4, 4.4 g, 12.0 mmol) in methanol (80 mL) was added K$_2$CO$_3$ (100 mg, 0.720 mmol) and the reaction was stirred at room temperature for 3 hr. The reaction mixture was filtered through celite, concentrated under reduced pressure to give a residue, which was dissolved in DCM, filtered and concentrated under reduced pressure to yield methyl 4-(4-ethynylphenyl)-2-methyl-2-(methylsulfonyl)butanoate (9.5, 2.49 g, 70.5%). MS: m/z calcd for C$_{15}$H$_{18}$O$_4$S, 294.09. found [M+H]$^+$ 295.2.

To a stirring solution of methyl 4-(4-ethynylphenyl)-2-methyl-2-(methylsulfonyl)butanoate (9.5, 2.49 g, 8.46 mmol) and silver nitrate (144 mg, 0.85 mmol) in acetone (24 mL) was added NBS (2.5 g, 14.33 mmol) and the reaction was stirred at room temperature for 1.5 hr. Solvent was removed under reduced pressure to give a residue, which was purified by flash chromatography (silica gel/30-50% EtOAc/hexanes) to yield methyl 4-(4-(bromoethynyl)phenyl)-2-methyl-2-(methylsulfonyl)butanoate (9.6, 150 mg, 0.40 mmol, 4.75%). MS: m/z calcd for $C_{15}H_{17}BrO_4S$, 372.0/374.0. found [M+H]⁺ 373.0/375.0.

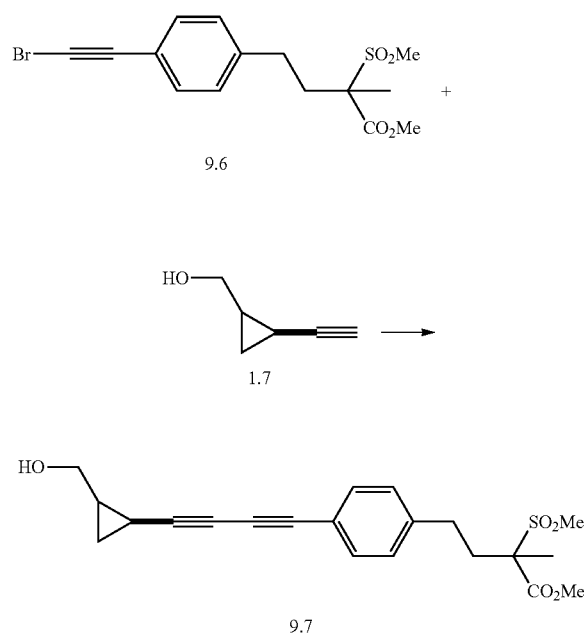

To a stirring solution of racemic ((trans)-2-ethynylcyclopropyl)methanol (1.7) in n-butylamine (750 µL, 30% in 1:1 water/THF) at −10° C. was added a solution of copper chloride (4 mg) in n-butylamine (300 µL, 30% in 1:1 water/THF) and $NH_2OH$ (12 µL of 50% in water) and the reaction was stirred for 10 min. A solution of methyl 4-(4-(bromoethynyl)phenyl)-2-methyl-2-(methylsulfonyl) butanoate (9.6) in n-butylamine (750 µL, 30% in 1:1 water/THF) and $NH_2OH$ (12 µL of 50% in water, 0.201 mmol) at −10° C. was then added dropwise over 10 min and the reaction was stirred at −10° C. for 10 min. The reaction mixture was diluted with EtOAc (10 mL) and washed with 1M citric acid (5 mL). The organic layer was washed with water (2×5 mL), sodium bicarbonate (5 mL), brine (5 mL), dried over $Na_2SO_4$ and concentrated under reduced pressure to give a thick oil (9.7), which was carried through to the next step without further purification. MS: m/z calcd for $C_{21}H_{24}O_5S$, 388.13. found [M+H]⁺ 389.2.

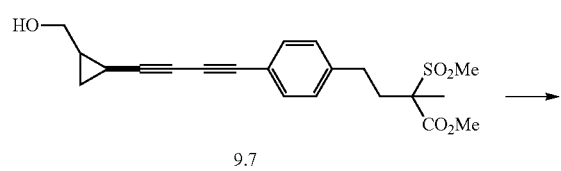

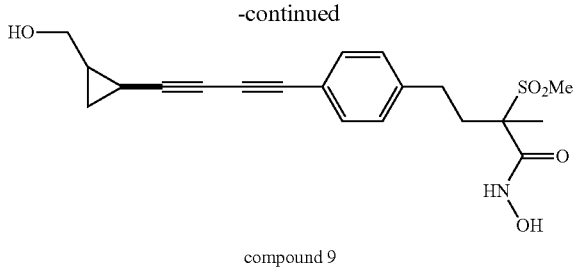

compound 9

To a stirring solution of methyl 4-(4-(((trans)-2-(hydroxymethyl)cyclopropyl)buta-1,3-diyn-1-yl)phenyl)-2-methyl-2-(methylsulfonyl) butanoate (9.7) in isopropanol (1.3 mL) at 0° C. was added hydroxylamine (946 µL, 15.44 mmol, 50% in water) and the reaction was stirred at room temperature overnight. The reaction mixture was neutralized with AcOH (884 µL, 15.44 mmol) and concentrated under reduced pressure to give a crude, which was purified by RP-HPLC (0-30% ACN in water) to yield N-hydroxy-4-(4-(((trans)-2-(hydroxymethyl)cyclopropyl) buta-1,3-diynyl) phenyl)-2-methyl-2-(methylsulfonyl)butanamide (9, 22.6 mg, 22.6% yield). MS: m/z calcd for $C_{20}H_{23}NO_5S$, 389.13. found [M+H]⁺ 390.2.

B. Antimicrobial Activity

1. Bacterial Screens and Cultures

Bacterial isolates were cultivated from −70° C. frozen stocks by overnight passages at 35° C. in ambient air on Mueller-Hinton agar (Beckton Dickinson, Franklin Lakes, N.J.). Clinical isolates tested were obtained from various geographically diverse hospitals in the US and abroad (Focus Diagnostics, Herndon, Va. and JMI, North Liberty, Iowa). Quality control strains were from the American Type Culture Collection (ATCC; Rockville, Md.).

2. Susceptibility Testing

Minimum Inhibitory Concentrations (MICs) were determined by the broth microdilution method in accordance with the Clinical and Laboratory Standards Institute (CLSI) guidelines. In brief, organism suspensions were adjusted to a 0.5 McFarland standard to yield a final inoculum between $3 \times 10^5$ and $7 \times 10^5$ colony-forming units (CFU)/mL. Drug dilutions and inocula were made in sterile, cation adjusted Mueller-Hinton Broth (Beckton Dickinson). An inoculum volume of 100 µL was added to wells containing 100 µL of broth with 2-fold serial dilutions of drug. All inoculated microdilution trays were incubated in ambient air at 35° C. for 18-24 hr. Following incubation, the lowest concentration of the drug that prevented visible growth (OD600 nm<0.05) was recorded as the MIC. Performance of the assay was monitored by the use of laboratory quality-control strains and levofloxacin, a compound with a defined MIC spectrum, in accordance with CLSI guidelines. Typically, compounds of the present invention have MIC values of 0.03-32 µg/mL. To this end, data for certain representative compounds is shown in Table II below.

TABLE II

| Minimum Inhibitory Concentrations (MICs) | | | |
| --- | --- | --- | --- |
| cmpd. | AECO | AKPN | APAE |
| 1 | A | A | C |
| 2 | A | C | C |
| 3 | A | A | A |
| 4 | A | C | A |
| 5 | A | A | A |

TABLE II-continued

Minimum Inhibitory Concentrations (MICs)

| cmpd. | AECO | AKPN | APAE |
|---|---|---|---|
| 6 | B | C | A |
| 7 | B | C | B |
| 8 | A | A | A |
| 9 | A | B | A |

MIC Key: A = MIC's of 1.0 µg/mL or less B = MIC's of greater than 1.0 µg/mL to 8.0 µg/mL C = MIC's of greater than 8.0 µg/mL to 16.0 µg/mL D = MIC's of greater than 16.0 µg/mL
* AECO is *Escherichia coli* ATCC25922. AKPN is *Klebsiella pneumonia* ATCC43816. APAE is *Pseudomonas aeruginosa* ATCC27853.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

Furthermore, while particular embodiments of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

What is claimed is:

1. A pharmaceutical composition comprising a pharmaceutically acceptable carrier, diluent or excipient and a compound of formula I:

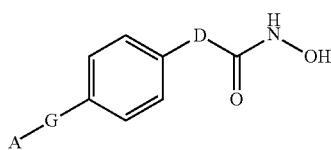

I or a stereoisomer or pharmaceutically acceptable salt thereof, wherein

A is selected from the group consisting of:
  (a) substituted $C_1$-$C_6$ alkyl, wherein at least one substituent is hydroxy; and
  (b) substituted $C_3$-$C_6$ cycloalkyl, wherein at least one substituent is selected from hydroxy and hydroxyalkyl;

G is selected from the group consisting of:

(a) —C≡C—;
(b) —CH=CH—C≡C—;
(c) —C≡C—CH=CH—;
(d) —C≡C—C≡C—;

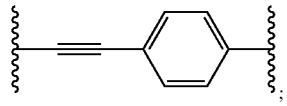
(e)

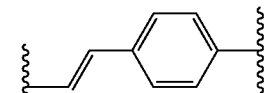
(f)

and
  (g) phenyl; and

D is selected from the group consisting of:

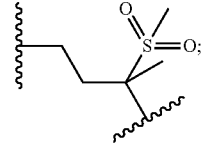
(a)

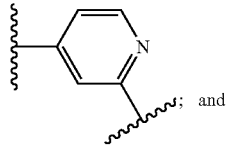
(b)

and

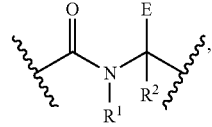
(c)

wherein
  $R^1$ and $R^2$ are each independently selected from hydrogen and methyl; and
  E is —C(CH$_3$)$_2$SCH$_3$, —C(CH$_3$)$_2$S(O)CH$_3$, —C(CH$_3$)$_2$S(O)$_2$CH$_3$, or —C(O)NHCH$_3$.

2. The pharmaceutical composition according to claim 1, wherein A is substituted $C_1$-$C_6$ alkyl, wherein at least one substituent is hydroxy.

3. The pharmaceutical composition according to claim 2, wherein A is substituted $C_1$-$C_6$ alkyl, wherein at least two substituents are hydroxy.

4. The pharmaceutical composition according to claim 2, wherein A is hydroxymethyl, hydroxyethyl, hydroxypropyl or dihydroxypropyl.

5. The pharmaceutical composition according to claim 1, wherein A is substituted $C_3$-$C_6$ cycloalkyl, wherein at least one substituent is selected from hydroxy and hydroxyalkyl.

6. The pharmaceutical composition according to claim 5, wherein A is substituted $C_3$-$C_6$ cycloalkyl, wherein at least one substituent is hydroxymethyl.

7. The pharmaceutical composition according to claim 6, wherein A is hydroxymethylcyclopropyl.

8. The pharmaceutical composition according to claim 5, wherein A is substituted $C_3$-$C_6$ cycloalkyl, wherein at least one substituent is hydroxy.

9. The pharmaceutical composition according to claim 1, wherein G is —C≡C—C≡C—.

10. The pharmaceutical composition according to claim 1, wherein D is

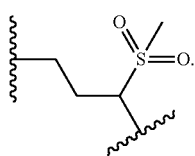

11. The pharmaceutical composition according to claim 1, wherein D is

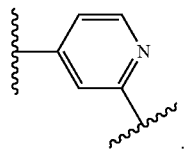 [SMILES: *c1ccnc(*)c1]

12. The pharmaceutical composition according to claim 1, wherein D is

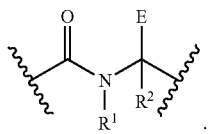

13. The pharmaceutical composition according to claim 12, wherein $R^1$ is hydrogen.
14. The pharmaceutical composition according to claim 13, wherein $R^2$ is hydrogen.
15. The pharmaceutical composition according to claim 14, wherein E is —C(CH$_3$)$_2$SCH$_3$.
16. The pharmaceutical composition according to claim 14, wherein E is —C(CH$_3$)$_2$S(O)$_2$CH$_3$.
17. The pharmaceutical composition according to claim 14, wherein E is —C(CH$_3$)$_2$S(O)CH$_3$.
18. The pharmaceutical composition according to claim 14, wherein E is —C(O)NHCH$_3$.
19. The pharmaceutical composition of claim 1 comprising a compound selected from the group consisting of:

N-hydroxy-4-(4-(((trans)-2-(hydroxymethyl)cyclopropyl)buta-1,3-diynyl)phenyl)picolinamide (Compound 2);

N—((R)-1-(hydroxyamino)-3-methyl-3-(methylthio)-1-oxobutan-2-yl)-4-(((trans)-2-(hydroxymethyl)cyclopropyl)buta-1,3-diynyl)benzamide (Compound 3);

N-((2R)-1-(hydroxyamino)-3-methyl-3-(methylsulfinyl)-1-oxobutan-2-yl)-4-(((trans)-2-(hydroxymethyl)cyclopropyl)buta-1,3-diynyl)benzamide (Compound 4);

N—((R)-1-(hydroxyamino)-3-methyl-3-(methylsulfonyl)-1-oxobutan-2-yl)-4-(((trans)-2-(hydroxymethyl) cyclopropyl)buta-1,3-diynyl)benzamide (Compound 5);

N—((S)-3-amino-1-(hydroxyamino)-3-methyl-1-oxobutan-2-yl)-6-(((trans)-2-(hydroxymethyl)cyclopropyl) ethynyl)-2-naphthamide (Compound 6);

N—((S)-3-amino-1-(hydroxyamino)-3-methyl-1-oxobutan-2-yl)-6-(((trans)-2-(hydroxymethyl)cyclopropyl) ethynyl)benzo[b]thiophene-2-carboxamide (Compound 7);

N1-hydroxy-2-(4-(((1R,2R)-2-(hydroxymethyl)cyclopropyl)buta-1,3-diynyl)benzamido)-N3-methylmalonamide (Compound 8);

N-hydroxy-4-(4-(((trans)-2-(hydroxymethyl)cyclopropyl)buta-1,3-diynyl)phenyl)-2-methyl-2-(methylsulfonyl)butanamide (Compound 9);

N-hydroxy-4-(4-(((1S,2S)-2-(hydroxymethyl)cyclopropyl)buta-1,3-diynyl)-2-oxopyridin-1(2H)-yl)-2-methyl-2-(methylsulfonyl)butanamide (Compound 35);

N-hydroxy-4-(4-(((1R,2R)-2-(hydroxymethyl)cyclopropyl)buta-1,3-diynyl)-2-oxopyridin-1(2H)-yl)-2-methyl-2-(methylsulfonyl)butanamide (Compound 36);

N-hydroxy-4-(4-(((1R,2S)-2-(hydroxymethyl)cyclopropyl)buta-1,3-diynyl)-2-oxopyridin-1(2H)-yl)-2-methyl-2-(methylsulfonyl)butanamide (Compound 37);

N-hydroxy-4-(4-(((1S,2R)-2-(hydroxymethyl)cyclopropyl)buta-1,3-diynyl)-2-oxopyridin-1(2H)-yl)-2-methyl-2-(methylsulfonyl)butanamide (Compound 38);

N-hydroxy-4-(4-(5-hydroxypenta-1,3-diynyl)-2-oxopyridin-1(2H)-yl)-2-methyl-2-(methylsulfonyl)butanamide (Compound 39);

N-hydroxy-4-(4-(6-hydroxyhexa-1,3-diynyl)-2-oxopyridin-1(2H)-yl)-2-methyl-2-(methylsulfonyl)butanamide (Compound 40);

N-hydroxy-4-(4-(5-hydroxyhexa-1,3-diynyl)-2-oxopyridin-1(2H)-yl)-2-methyl-2-(methylsulfonyl)butanamide (Compound 41);

N-hydroxy-4-(4-(6-hydroxy-5-methylhexa-1,3-diynyl)-2-oxopyridin-1(2H)-yl)-2-methyl-2-(methylsulfonyl) butanamide (Compound 42);

4-(4-(5,6-dihydroxyhexa-1,3-diynyl)-2-oxopyridin-1 (2H)-yl)-N-hydroxy-2-methyl-2-(methylsulfonyl)butanamide (Compound 43);

4-(4-(6,7-dihydroxyhepta-1,3-diynyl)-2-oxopyridin-1 (2H)-yl)-N-hydroxy-2-methyl-2-(methylsulfonyl)butanamide (Compound 44);

N-hydroxy-4-(4-((3-hydroxycyclobutyl)buta-1,3-diynyl)-2-oxopyridin-1(2H)-yl)-2-methyl-2-(methylsulfonyl) butanamide (Compound 45);

N-hydroxy-4-(4-((3-(hydroxymethyl)cyclobutyl)buta-1, 3-diynyl)-2-oxopyridin-1(2H)-yl)-2-methyl-2-(methylsulfonyl)butanamide (Compound 46);

N-hydroxy-4-(4-((3-(hydroxymethyl)cyclopentyl)buta-1, 3-diynyl)-2-oxopyridin-1(2H)-yl)-2-methyl-2-(methylsulfonyl)butanamide (Compound 47);

N-hydroxy-4-(4-(6-hydroxy-5-methoxyhexa-1,3-diynyl)-2-oxopyridin-1(2H)-yl)-2-methyl-2-(methylsulfonyl) butanamide (Compound 48);

N-hydroxy-4-(4-(7-hydroxy-6-methoxyhepta-1,3-diynyl)-2-oxopyridin-1(2H)-yl)-2-methyl-2-(methylsulfonyl)butanamide (Compound 49);

N-hydroxy-4-(4-(6-hydroxyhexa-1,3-diynyl)-2-oxopyridin-1(2H)-yl)-2-methyl-2-(methylsulfonyl)butanamide (Compound 50);

N-hydroxy-4-(4-(4-(((1S,2S)-2-(hydroxymethyl)cyclopropyl)ethynyl)phenyl)-2-oxopyridin-1(2H)-yl)-2-methyl-2-(methylsulfonyl)butanamide (Compound 51);

N-hydroxy-4-(4-(4-(((1R,2R)-2-(hydroxymethyl)cyclopropyl)ethynyl)phenyl)-2-oxopyridin-1(2H)-yl)-2-methyl-2-(methylsulfonyl)butanamide (Compound 52);

N-hydroxy-4-(4-(4-(((1R,2S)-2-(hydroxymethyl)cyclopropyl)ethynyl)phenyl)-2-oxopyridin-1(2H)-yl)-2-methyl-2-(methylsulfonyl)butanamide (Compound 53);

N-hydroxy-4-(4-(4-(((1S,2R)-2-(hydroxymethyl)cyclopropyl)ethynyl)phenyl)-2-oxopyridin-1(2H)-yl)-2-methyl-2-(methylsulfonyl)butanamide (Compound 54);

N-hydroxy-4-(4-(4-(3-hydroxyprop-1-ynyl)phenyl)-2-oxopyridin-1(2H)-yl)-2-methyl-2-(methylsulfonyl)butanamide (Compound 55);

N-hydroxy-4-(4-(4-(4-hydroxybut-1-ynyl)phenyl)-2-oxopyridin-1(2H)-yl)-2-methyl-2-(methylsulfonyl)butanamide (Compound 56);

N-hydroxy-4-(4-(4-(3-hydroxybut-1-ynyl)phenyl)-2-oxopyridin-1(2H)-yl)-2-methyl-2-(methylsulfonyl)butanamide (Compound 57);

N-hydroxy-4-(4-(4-(4-hydroxy-3-methylbut-1-ynyl)phenyl)-2-oxopyridin-1(2H)-yl)-2-methyl-2-(methylsulfonyl)butanamide (Compound 58);

4-(4-(4-(3,4-dihydroxybut-1-ynyl)phenyl)-2-oxopyridin-1(2H)-yl)-N-hydroxy-2-methyl-2-(methylsulfonyl)butanamide (Compound 59);

4-(4-(4-(4,5-dihydroxypent-1-ynyl)phenyl)-2-oxopyridin-1(2H)-yl)-N-hydroxy-2-methyl-2-(methylsulfonyl)butanamide (Compound 60);

N-hydroxy-4-(4-(4-((3-hydroxycyclobutyl)ethynyl)phenyl)-2-oxopyridin-1(2H)-yl)-2-methyl-2-(methylsulfonyl)butanamide (Compound 61);

N-hydroxy-4-(4-(4-((3-(hydroxymethyl)cyclobutyl)ethynyl)phenyl)-2-oxopyridin-1(2H)-yl)-2-methyl-2-(methylsulfonyl)butanamide (Compound 62);

N-hydroxy-4-(4-(4-((3-(hydroxymethyl)cyclopentyl)ethynyl)phenyl)-2-oxopyridin-1(2H)-yl)-2-methyl-2-(methylsulfonyl)butanamide (Compound 63);

N-hydroxy-4-(4-(4-(4-hydroxy-3-methoxybut-1-ynyl)phenyl)-2-oxopyridin-1(2H)-yl)-2-methyl-2-(methylsulfonyl)butanamide (Compound 64);

N-hydroxy-4-(4-(4-(5-hydroxy-4-methoxypent-1-ynyl)phenyl)-2-oxopyridin-1(2H)-yl)-2-methyl-2-(methylsulfonyl)butanamide (Compound 65);

N-hydroxy-4-(4-(4-(6-hydroxyhexa-1,3-diynyl)-2-oxopyridin-1(2H)-yl)-2-methyl-2-(methylsulfonyl)butanamide (Compound 66);

N-hydroxy-4-(4-(4-((2S)-2-(hydroxymethyl)cyclopropyl)phenyl)-2-oxopyridin-1(2H)-yl)-2-methyl-2-(methylsulfonyl)butanamide (Compound 67);

N-hydroxy-4-(4-(4-((2R)-2-(hydroxymethyl)cyclopropyl)phenyl)-2-oxopyridin-1(2H)-yl)-2-methyl-2-(methylsulfonyl)butanamide (Compound 68);

N-hydroxy-4-(4-(4-((2S)-2-(hydroxymethyl)cyclopropyl)phenyl)-2-oxopyridin-1(2H)-yl)-2-methyl-2-(methylsulfonyl)butanamide (Compound 69);

N-hydroxy-4-(4-(4-((2R)-2-(hydroxymethyl)cyclopropyl)phenyl)-2-oxopyridin-1(2H)-yl)-2-methyl-2-(methylsulfonyl)butanamide (Compound 70);

N-hydroxy-4-(4-(4-(hydroxymethyl)phenyl)-2-oxopyridin-1(2H)-yl)-2-methyl-2-(methylsulfonyl)butanamide (Compound 71);

N-hydroxy-4-(4-(4-(2-hydroxyethyl)phenyl)-2-oxopyridin-1(2H)-yl)-2-methyl-2-(methylsulfonyl)butanamide (Compound 72);

N-hydroxy-4-(4-(4-(1-hydroxyethyl)phenyl)-2-oxopyridin-1(2H)-yl)-2-methyl-2-(methylsulfonyl)butanamide (Compound 73);

N-hydroxy-4-(4-(4-(1-hydroxypropan-2-yl)phenyl)-2-oxopyridin-1(2H)-yl)-2-methyl-2-(methylsulfonyl)butanamide (Compound 74);

4-(4-(4-(1,2-dihydroxyethyl)phenyl)-2-oxopyridin-1(2H)-yl)-N-hydroxy-2-methyl-2-(methylsulfonyl)butanamide (Compound 75);

4-(4-(4-(2,3-dihydroxypropyl)phenyl)-2-oxopyridin-1(2H)-yl)-N-hydroxy-2-methyl-2-(methylsulfonyl)butanamide (Compound 76);

N-hydroxy-4-(4-(4-(3-hydroxycyclobutyl)phenyl)-2-oxopyridin-1(2H)-yl)-2-methyl-2-(methylsulfonyl)butanamide (Compound 77);

N-hydroxy-4-(4-(4-(3-(hydroxymethyl)cyclobutyl)phenyl)-2-oxopyridin-1(2H)-yl)-2-methyl-2-(methylsulfonyl)butanamide (Compound 78);

N-hydroxy-4-(4-(4-(3-(hydroxymethyl)cyclopentyl)phenyl)-2-oxopyridin-1(2H)-yl)-2-methyl-2-(methylsulfonyl)butanamide (Compound 79);

N-hydroxy-4-(4-(4-(2-hydroxy-1-methoxyethyl)phenyl)-2-oxopyridin-1(2H)-yl)-2-methyl-2-(methylsulfonyl)butanamide (Compound 80);

N-hydroxy-4-(4-(4-(3-hydroxy-2-methoxypropyl)phenyl)-2-oxopyridin-1(2H)-yl)-2-methyl-2-(methylsulfonyl)butanamide (Compound 81);

N-hydroxy-4-(4-(6-hydroxyhexa-1,3-diynyl)-2-oxopyridin-1(2H)-yl)-2-methyl-2-(methylsulfonyl)butanamide (Compound 82);

N-hydroxy-4-(4-(4-((E)-2-((1R,2S)-2-(hydroxymethyl)cyclopropyl)vinyl)phenyl)-2-oxopyridin-1(2H)-yl)-2-methyl-2-(methylsulfonyl)butanamide (Compound 83);

N-hydroxy-4-(4-(4-((E)-2-((1S,2R)-2-(hydroxymethyl)cyclopropyl)vinyl)phenyl)-2-oxopyridin-1(2H)-yl)-2-methyl-2-(methylsulfonyl)butanamide (Compound 84);

N-hydroxy-4-(4-(4-((E)-2-((1S,2S)-2-(hydroxymethyl)cyclopropyl)vinyl)phenyl)-2-oxopyridin-1(2H)-yl)-2-methyl-2-(methylsulfonyl)butanamide (Compound 85);

N-hydroxy-4-(4-(4-((E)-2-((1R,2R)-2-(hydroxymethyl)cyclopropyl)vinyl)phenyl)-2-oxopyridin-1(2H)-yl)-2-methyl-2-(methylsulfonyl)butanamide (Compound 86);

(E)-N-hydroxy-4-(4-(4-(3-hydroxyprop-1-enyl)phenyl)-2-oxopyridin-1(2H)-yl)-2-methyl-2-(methylsulfonyl)butanamide (Compound 87);

(E)-N-hydroxy-4-(4-(4-(4-hydroxybut-1-enyl)phenyl)-2-oxopyridin-1(2H)-yl)-2-methyl-2-(methylsulfonyl)butanamide (Compound 88);

(E)-N-hydroxy-4-(4-(4-(3-hydroxybut-1-enyl)phenyl)-2-oxopyridin-1(2H)-yl)-2-methyl-2-(methylsulfonyl)butanamide (Compound 89);

(E)-N-hydroxy-4-(4-(4-(4-hydroxy-3-methylbut-1-enyl)phenyl)-2-oxopyridin-1(2H)-yl)-2-methyl-2-(methylsulfonyl)butanamide (Compound 90);

(E)-4-(4-(4-(3,4-dihydroxybut-1-enyl)phenyl)-2-oxopyridin-1(2H)-yl)-N-hydroxy-2-methyl-2-(methylsulfonyl)butanamide (Compound 91);

(E)-4-(4-(4-(4, 5-dihydroxypent-1-enyl)phenyl)-2-oxopyridin-1(2H)-yl)-N-hydroxy-2-methyl-2-(methylsulfonyl)butanamide (Compound 92);

(E)-N-hydroxy-4-(4-(4-(2-(3-hydroxycyclobutyl)vinyl)phenyl)-2-oxopyridin-1(2H)-yl)-2-methyl-2-(methylsulfonyl)butanamide (Compound 93);

(E)-N-hydroxy-4-(4-(4-(2-(3-(hydroxymethyl)cyclobutyl)vinyl)phenyl)-2-oxopyridin-1(2H)-yl)-2-methyl-2-(methylsulfonyl)butanamide (Compound 94);

(E)-N-hydroxy-4-(4-(4-(2-(3-(hydroxymethyl)cyclopentyl)vinyl)phenyl)-2-oxopyridin-1(2H)-yl)-2-methyl-2-(methylsulfonyl)butanamide (Compound 95);

(E)-N-hydroxy-4-(4-(4-(4-hydroxy-3-methoxybut-1-enyl)phenyl)-2-oxopyridin-1(2H)-yl)-2-methyl-2-(methylsulfonyl)butanamide (Compound 96);

(E)-N-hydroxy-4-(4-(4-(5-hydroxy-4-methoxypent-1-enyl)phenyl)-2-oxopyridin-1(2H)-yl)-2-methyl-2-(methylsulfonyl)butanamide (Compound 97);

N-hydroxy-4-(4-(6-hydroxyhexa-1,3-diynyl)-2-oxopyridin-1(2H)-yl)-2-methyl-2-(methylsulfonyl)butanamide (Compound 98);

N-hydroxy-4-(4-(((1S,2S)-2-(hydroxymethyl)cyclopropyl)buta-1,3-diynyl)phenyl)-2-methyl-2-(methylsulfonyl)butanamide (Compound 99);

N-hydroxy-4-(4-(((1R,2R)-2-(hydroxymethyl)cyclopropyl)buta-1,3-diynyl)phenyl)-2-methyl-2-(methylsulfonyl)butanamide (Compound 100);

N-hydroxy-4-(4-(((1R,2S)-2-(hydroxymethyl)cyclopropyl)buta-1,3-diynyl)phenyl)-2-methyl-2-(methylsulfonyl)butanamide (Compound 101);

N-hydroxy-4-(4-(((1S,2R)-2-(hydroxymethyl)cyclopropyl)buta-1,3-diynyl)phenyl)-2-methyl-2-(methylsulfonyl)butanamide (Compound 102);

N-hydroxy-4-(4-(5-hydroxypenta-1,3-diynyl)phenyl)-2-methyl-2-(methylsulfonyl)butanamide (Compound 103);

N-hydroxy-4-(4-(6-hydroxyhexa-1,3-diynyl)phenyl)-2-methyl-2-(methylsulfonyl)butanamide (Compound 104);

N-hydroxy-4-(4-(5-hydroxyhexa-1,3-diynyl)phenyl)-2-methyl-2-(methylsulfonyl)butanamide (Compound 105);

N-hydroxy-4-(4-(6-hydroxy-5-methylhexa-1,3-diynyl)phenyl)-2-methyl-2-(methylsulfonyl)butanamide (Compound 106);

4-(4-(5,6-dihydroxyhexa-1,3-diynyl)phenyl)-N-hydroxy-2-methyl-2-(methylsulfonyl)butanamide (Compound 107);

4-(4-(6,7-dihydroxyhepta-1,3-diynyl)phenyl)-N-hydroxy-2-methyl-2-(methylsulfonyl)butanamide (Compound 108);

N-hydroxy-4-(4-((3-hydroxycyclobutyl)buta-1,3-diynyl)phenyl)-2-methyl-2-(methylsulfonyl)butanamide (Compound 109);

N-hydroxy-4-(4-((3-(hydroxymethyl)cyclobutyl)buta-1,3-diynyl)phenyl)-2-methyl-2-(methylsulfonyl)butanamide (Compound 110);

N-hydroxy-4-(4-((3-(hydroxymethyl)cyclopentyl)buta-1,3-diynyl)phenyl)-2-methyl-2-(methylsulfonyl)butanamide (Compound 111);

N-hydroxy-4-(4-(6-hydroxy-5-methoxyhexa-1,3-diynyl)phenyl)-2-methyl-2-(methylsulfonyl)butanamide (Compound 112);

N-hydroxy-4-(4-(7-hydroxy-6-methoxyhepta-1,3-diynyl)phenyl)-2-methyl-2-(methylsulfonyl)butanamide (Compound 113);

N-hydroxy-4-(4-(6-hydroxyhexa-1,3-diynyl)phenyl)-2-methyl-2-(methylsulfonyl)butanamide (Compound 114);

N-hydroxy-4-(4'-(((1S,2S)-2-(hydroxymethyl)cyclopropyl)ethynyl)biphenyl-4-yl)-2-methyl-2-(methylsulfonyl)butanamide (Compound 115);

N-hydroxy-4-(4'-(((1R,2R)-2-(hydroxymethyl)cyclopropyl)ethynyl)biphenyl-4-yl)-2-methyl-2-(methylsulfonyl)butanamide (Compound 116);

N-hydroxy-4-(4'-(((1R,2S)-2-(hydroxymethyl)cyclopropyl)ethynyl)biphenyl-4-yl)-2-methyl-2-(methylsulfonyl)butanamide (Compound 117);

N-hydroxy-4-(4'-(((1S,2R)-2-(hydroxymethyl)cyclopropyl)ethynyl)biphenyl-4-yl)-2-methyl-2-(methylsulfonyl)butanamide (Compound 118);

N-hydroxy-4-(4'-(3-hydroxyprop-1-ynyl)biphenyl-4-yl)-2-methyl-2-(methylsulfonyl)butanamide (Compound 119);

N-hydroxy-4-(4'-(4-hydroxybut-1-ynyl)biphenyl-4-yl)-2-methyl-2-(methylsulfonyl)butanamide (Compound 120);

N-hydroxy-4-(4'-(3-hydroxybut-1-ynyl)biphenyl-4-yl)-2-methyl-2-(methylsulfonyl)butanamide (Compound 121);

N-hydroxy-4-(4'-(4-hydroxy-3-methylbut-1-ynyl)biphenyl-4-yl)-2-methyl-2-(methylsulfonyl)butanamide (Compound 122);

4-(4'-(3,4-dihydroxybut-1-ynyl)biphenyl-4-yl)-N-hydroxy-2-methyl-2-(methylsulfonyl)butanamide (Compound 123);

4-(4'-(4, 5-dihydroxypent-1-ynyl)biphenyl-4-yl)-N-hydroxy-2-methyl-2-(methylsulfonyl)butanamide (Compound 124);

N-hydroxy-4-(4'-((3-hydroxycyclobutyl)ethynyl)biphenyl-4-yl)-2-methyl-2-(methylsulfonyl)butanamide (Compound 125);

N-hydroxy-4-(4'-((3-(hydroxymethyl)cyclobutyl)ethynyl)biphenyl-4-yl)-2-methyl-2-(methylsulfonyl)butanamide (Compound 126);

N-hydroxy-4-(4'-((3-(hydroxymethyl)cyclopentyl)ethynyl)biphenyl-4-yl)-2-methyl-2-(methylsulfonyl)butanamide (Compound 127);

N-hydroxy-4-(4'-(4-hydroxy-3-methoxybut-1-ynyl)biphenyl-4-yl)-2-methyl-2-(methylsulfonyl)butanamide (Compound 128);

N-hydroxy-4-(4'-(5-hydroxy-4-methoxypent-1-ynyl)biphenyl-4-yl)-2-methyl-2-(methylsulfonyl)butanamide (Compound 129);

N-hydroxy-4-(4-(6-hydroxyhexa-1,3-diynyl)phenyl)-2-methyl-2-(methylsulfonyl)butanamide (Compound 130);

N-hydroxy-4-(4'-((2S)-2-(hydroxymethyl)cyclopropyl)biphenyl-4-yl)-2-methyl-2-(methylsulfonyl)butanamide (Compound 131);

N-hydroxy-4-(4'-((2R)-2-(hydroxymethyl)cyclopropyl)biphenyl-4-yl)-2-methyl-2-(methylsulfonyl)butanamide (Compound 132);

N-hydroxy-4-(4'-((2S)-2-(hydroxymethyl)cyclopropyl)biphenyl-4-yl)-2-methyl-2-(methylsulfonyl)butanamide (Compound 133);

N-hydroxy-4-(4'-((2R)-2-(hydroxymethyl)cyclopropyl)biphenyl-4-yl)-2-methyl-2-(methylsulfonyl)butanamide (Compound 134);

N-hydroxy-4-(4'-(hydroxymethyl)biphenyl-4-yl)-2-methyl-2-(methylsulfonyl)butanamide (Compound 135);

N-hydroxy-4-(4'-(2-hydroxyethyl)biphenyl-4-yl)-2-methyl-2-(methylsulfonyl)butanamide (Compound 136);

N-hydroxy-4-(4'-(1-hydroxyethyl)biphenyl-4-yl)-2-methyl-2-(methylsulfonyl)butanamide (Compound 137);

N-hydroxy-4-(4'-(1-hydroxypropan-2-yl)biphenyl-4-yl)-2-methyl-2-(methylsulfonyl)butanamide (Compound 138);

4-(4'-(1,2-dihydroxyethyl)biphenyl-4-yl)-N-hydroxy-2-methyl-2-(methylsulfonyl)butanamide (Compound 139);

4-(4'-(2,3-dihydroxypropyl)biphenyl-4-yl)-N-hydroxy-2-methyl-2-(methylsulfonyl)butanamide (Compound 140);

N-hydroxy-4-(4'-(3-hydroxycyclobutyl)biphenyl-4-yl)-2-methyl-2-(methylsulfonyl)butanamide (Compound 141);

N-hydroxy-4-(4'-(3-(hydroxymethyl)cyclobutyl)biphenyl-4-yl)-2-methyl-2-(methylsulfonyl)butanamide (Compound 142);

N-hydroxy-4-(4'-(3-(hydroxymethyl)cyclopentyl)biphenyl-4-yl)-2-methyl-2-(methylsulfonyl)butanamide (Compound 143);

N-hydroxy-4-(4'-(2-hydroxy-1-methoxyethyl)biphenyl-4-yl)-2-methyl-2-(methylsulfonyl)butanamide (Compound 144);

N-hydroxy-4-(4'-(3-hydroxy-2-methoxypropyl)biphenyl-4-yl)-2-methyl-2-(methylsulfonyl)butanamide (Compound 145);

N-hydroxy-4-(4'-((E)-2-((1R,2S)-2-(hydroxymethyl)cyclopropyl)vinyl)biphenyl-4-yl)-2-methyl-2-(methylsulfonyl)butanamide (Compound 146);

N-hydroxy-4-(4'-((E)-2-((1S,2R)-2-(hydroxymethyl)cyclopropyl)vinyl)biphenyl-4-yl)-2-methyl-2-(methylsulfonyl)butanamide (Compound 147);

N-hydroxy-4-(4'-((E)-2-((1S,2S)-2-(hydroxymethyl)cyclopropyl)vinyl)biphenyl-4-yl)-2-methyl-2-(methylsulfonyl)butanamide (Compound 148);

N-hydroxy-4-(4'-((E)-2-((1R,2R)-2-(hydroxymethyl)cyclopropyl)vinyl)biphenyl-4-yl)-2-methyl-2-(methylsulfonyl)butanamide (Compound 149);

(E)-N-hydroxy-4-(4'-(3-hydroxyprop-1-enyl)biphenyl-4-yl)-2-methyl-2-(methylsulfonyl)butanamide (Compound 150);

(E)-N-hydroxy-4-(4'-(4-hydroxybut-1-enyl)biphenyl-4-yl)-2-methyl-2-(methylsulfonyl)butanamide (Compound 151);

(E)-N-hydroxy-4-(4'-(3-hydroxybut-1-enyl)biphenyl-4-yl)-2-methyl-2-(methylsulfonyl)butanamide (Compound 152);

(E)-N-hydroxy-4-(4'-(4-hydroxy-3-methylbut-1-enyl)biphenyl-4-yl)-2-methyl-2-(methylsulfonyl)butanamide (Compound 153);

(E)-4-(4'-(3,4-dihydroxybut-1-enyl)biphenyl-4-yl)-N-hydroxy-2-methyl-2-(methylsulfonyl)butanamide (Compound 154);

(E)-4-(4'-(4,5-dihydroxypent-1-enyl)biphenyl-4-yl)-N-hydroxy-2-methyl-2-(methylsulfonyl)butanamide (Compound 155);

(E)-N-hydroxy-4-(4'-(2-(3-hydroxycyclobutyl)vinyl)biphenyl-4-yl)-2-methyl-2-(methylsulfonyl)butanamide (Compound 156);

(E)-N-hydroxy-4-(4'-(2-(3-(hydroxymethyl)cyclobutyl)vinyl)biphenyl-4-yl)-2-methyl-2-(methylsulfonyl)butanamide (Compound 157);

(E)-N-hydroxy-4-(4'-(2-(3-(hydroxymethyl)cyclopentyl)vinyl)biphenyl-4-yl)-2-methyl-2-(methylsulfonyl)butanamide (Compound 158);

(E)-N-hydroxy-4-(4-(4-(4-hydroxy-3-methoxybut-1-enyl)phenyl)-2-oxopyridin-1(2H)-yl)-2-methyl-2-(methylsulfonyl)butanamide (Compound 159);

(R)—N-(1-(hydroxyamino)-3-methyl-3-(methylsulfonyl)-1-oxobutan-2-yl)-4-(5-hydroxypenta-1,3-diynyl)benzamide (Compound 160);

(R)—N-(1-(hydroxyamino)-3-methyl-3-(methylsulfonyl)-1-oxobutan-2-yl)-4-(6-hydroxyhexa-1,3-diynyl)benzamide (Compound 161);

4-(5,6-dihydroxyhexa-1,3-diynyl)-N—((R)-1-(hydroxyamino)-3-methyl-3-(methylsulfonyl)-1-oxobutan-2-yl)benzamide (Compound 162);

4-(6,7-dihydroxyhepta-1,3-diynyl)-N—((R)-1-(hydroxyamino)-3-methyl-3-(methylsulfonyl)-1-oxobutan-2-yl)benzamide (Compound 163);

4-(6-hydroxy-5-methylhexa-1,3-diynyl)-N—((R)-1-(hydroxyamino)-3-methyl-3-(methylsulfonyl)-1-oxobutan-2-yl)benzamide (Compound 164);

(R)—N-(1-(hydroxyamino)-3-methyl-3-(methylsulfonyl)-1-oxobutan-2-yl)-4-((3-hydroxycyclobutyl)buta-1,3-diynyl)benzamide (Compound 165);

(R)—N-(1-(hydroxyamino)-3-methyl-3-(methylsulfonyl)-1-oxobutan-2-yl)-4-((3-(hydroxymethyl)cyclobutyl)buta-1,3-diynyl)benzamide (Compound 166);

N—((R)-1-(hydroxyamino)-3-methyl-3-(methylsulfonyl)-1-oxobutan-2-yl)-4-((3-(hydroxymethyl)cyclopentyl)buta-1,3-diynyl)benzamide (Compound 167);

N—((R)-1-(hydroxyamino)-3-methyl-3-(methylsulfonyl)-1-oxobutan-2-yl)-4-(5-hydroxyhexa-1,3-diynyl)benzamide (Compound 168);

4-(6-hydroxy-5-methoxyhexa-1,3-diynyl)-N—((R)-1-(hydroxyamino)-3-methyl-3-(methylsulfonyl)-1-oxobutan-2-yl)benzamide (Compound 169);

4-(7-hydroxy-6-methoxyhepta-1,3-diynyl)-N—((R)-1-(hydroxyamino)-3-methyl-3-(methylsulfonyl)-1-oxobutan-2-yl)benzamide (Compound 170);

N—((R)-1-(hydroxyamino)-3-methyl-3-(methylsulfonyl)-1-oxobutan-2-yl)-4-((2-(hydroxymethyl)cyclopropyl)buta-1,3-diynyl)benzamide (Compound 171);

N-((2R)-1-(hydroxyamino)-3-methyl-3-(methylsulfinyl)-1-oxobutan-2-yl)-4-(5-hydroxypenta-1,3-diynyl)benzamide (Compound 172);

N-((2R)-1-(hydroxyamino)-3-methyl-3-(methylsulfinyl)-1-oxobutan-2-yl)-4-(6-hydroxyhexa-1,3-diynyl)benzamide (Compound 173);

4-(5,6-dihydroxyhexa-1,3-diynyl)-N-((2R)-1-(hydroxyamino)-3-methyl-3-(methylsulfinyl)-1-oxobutan-2-yl)benzamide (Compound 174);

4-(6, 7-dihydroxyhepta-1,3-diynyl)-N-((2R)-1-(hydroxyamino)-3-methyl-3-(methylsulfinyl)-1-oxobutan-2-yl)benzamide (Compound 175);

4-(6-hydroxy-5-methylhexa-1,3-diynyl)-N—((R)-1-(hydroxyamino)-3-methyl-3-(methylsulfonyl)-1-oxobutan-2-yl)benzamide (Compound 176);

N-((2R)-1-(hydroxyamino)-3-methyl-3-(methylsulfinyl)-1-oxobutan-2-yl)-4-((3-hydroxycyclobutyl)buta-1,3-diynyl)benzamide (Compound 177);

N-((2R)-1-(hydroxyamino)-3-methyl-3-(methylsulfinyl)-1-oxobutan-2-yl)-4-((3-(hydroxymethyl)cyclobutyl)buta-1,3-diynyl)benzamide (Compound 178);

N-((2R)-1-(hydroxyamino)-3-methyl-3-(methylsulfinyl)-1-oxobutan-2-yl)-4-((3-(hydroxymethyl)cyclopentyl)buta-1,3-diynyl)benzamide (Compound 179);

N-((2R)-1-(hydroxyamino)-3-methyl-3-(methylsulfinyl)-1-oxobutan-2-yl)-4-(5-hydroxyhexa-1,3-diynyl)benzamide (Compound 180);

4-(6-hydroxy-5-methoxyhexa-1,3-diynyl)-N-((2R)-1-(hydroxyamino)-3-methyl-3-(methylsulfinyl)-1-oxobutan-2-yl)benzamide (Compound 181);

4-(7-hydroxy-6-methoxyhepta-1,3-diynyl)-N-((2R)-1-(hydroxyamino)-3-methyl-3-(methylsulfinyl)-1-oxobutan-2-yl)benzamide (Compound 182);

N-((2R)-1-(hydroxyamino)-3-methyl-3-(methylsulfinyl)-1-oxobutan-2-yl)-4-((2-(hydroxymethyl)cyclopropyl)buta-1,3-diynyl)benzamide (Compound 183);

N—((R)-1-(hydroxyamino)-3-methyl-3-(methylthio)-1-oxobutan-2-yl)-4-((2-(hydroxymethyl)cyclopropyl)buta-1,3-diynyl)benzamide (Compound 184);

(R)—N-(1-(hydroxyamino)-3-methyl-3-(methylthio)-1-oxobutan-2-yl)-4-(5-hydroxypenta-1,3-diynyl)benzamide (Compound 185);

(R)—N-(1-(hydroxyamino)-3-methyl-3-(methylthio)-1-oxobutan-2-yl)-4-(6-hydroxyhexa-1,3-diynyl)benzamide (Compound 186);

4-(5,6-dihydroxyhexa-1,3-diynyl)-N—((R)-1-(hydroxyamino)-3-methyl-3-(methylthio)-1-oxobutan-2-yl)benzamide (Compound 187);

4-(6,7-dihydroxyhepta-1,3-diynyl)-N—((R)-1-(hydroxyamino)-3-methyl-3-(methylthio)-1-oxobutan-2-yl)benzamide (Compound 188);

4-(6-hydroxy-5-methylhexa-1,3-diynyl)-N—((R)-1-(hydroxyamino)-3-methyl-3-(methylthio)-1-oxobutan-2-yl)benzamide (Compound 189);

(R)—N-(1-(hydroxyamino)-3-methyl-3-(methylthio)-1-oxobutan-2-yl)-4-((3-hydroxycyclobutyl)buta-1,3-diynyl)benzamide (Compound 190);

(R)—N-(1-(hydroxyamino)-3-methyl-3-(methylthio)-1-oxobutan-2-yl)-4-((3-(hydroxymethyl)cyclobutyl)buta-1,3-diynyl)benzamide (Compound 191);

N—((R)-1-(hydroxyamino)-3-methyl-3-(methylthio)-1-oxobutan-2-yl)-4-((3-(hydroxymethyl)cyclopentyl)buta-1,3-diynyl)benzamide (Compound 192);

N—((R)-1-(hydroxyamino)-3-methyl-3-(methylthio)-1-oxobutan-2-yl)-4-(5-hydroxyhexa-1,3-diynyl)benzamide (Compound 193);

4-(6-hydroxy-5-methoxyhexa-1,3-diynyl)-N—((R)-1-(hydroxyamino)-3-methyl-3-(methylthio)-1-oxobutan-2-yl)benzamide (Compound 194);

4-(7-hydroxy-6-methoxyhepta-1,3-diynyl)-N—((R)-1-(hydroxyamino)-3-methyl-3-(methylthio)-1-oxobutan-2-yl)benzamide (Compound 195);

N—((R)-1-(hydroxyamino)-3-methyl-3-(methylthio)-1-oxobutan-2-yl)-4-((2-(hydroxymethyl)cyclopropyl)buta-1,3-diynyl)benzamide (Compound 196);

N1-hydroxy-2-(4-((2-(hydroxymethyl)cyclopropyl)buta-1,3-diynyl)benzamido)-N3-methylmalonamide (Compound 197);

N1-hydroxy-2-(4-(5-hydroxypenta-1,3-diynyl)benzamido)-N3-methylmalonamide (Compound 198);

N1-hydroxy-2-(4-(6-hydroxyhexa-1,3-diynyl)benzamido)-N3-methylmalonamide (Compound 199);

N1-hydroxy-2-(4-(5-hydroxyhexa-1,3-diynyl)benzamido)-N3-methylmalonamide (Compound 200);

2-(4-(5,6-dihydroxyhexa-1,3-diynyl)benzamido)-N1-hydroxy-N3-methylmalonamide (Compound 201);

2-(4-(6,7-dihydroxyhepta-1,3-diynyl)benzamido)-N1-hydroxy-N3-methylmalonamide (Compound 202);

N1-hydroxy-2-(4-(6-hydroxy-5-methylhexa-1,3-diynyl)benzamido)-N3-methylmalonamide (Compound 203);

N1-hydroxy-2-(4-((3-hydroxycyclobutyl)buta-1,3-diynyl)benzamido)-N3-methylmalonamide (Compound 204);

N1-hydroxy-2-(4-((3-(hydroxymethyl)cyclobutyl)buta-1,3-diynyl)benzamido)-N3-methylmalonamide (Compound 205);

N1-hydroxy-2-(4-((3-(hydroxymethyl)cyclopentyl)buta-1,3-diynyl)benzamido)-N3-methylmalonamide (Compound 206);

N1-hydroxy-2-(4-(6-hydroxy-5-methoxyhexa-1,3-diynyl)benzamido)-N3-methylmalonamide (Compound 207);

N1-hydroxy-2-(4-(7-hydroxy-6-methoxyhepta-1,3-diynyl)benzamido)-N3-methylmalonamide (Compound 208);

N1-hydroxy-2-(4-((2-(hydroxymethyl)cyclopropyl)buta-1,3-diynyl)-N-methylbenzamido)-N3-methylmalonamide (Compound 209);

N1-hydroxy-2-(4-(5-hydroxypenta-1,3-diynyl)-N-methylbenzamido)-N3-methylmalonamide (Compound 210);

N1-hydroxy-2-(4-(6-hydroxyhexa-1,3-diynyl)-N-methylbenzamido)-N3-methylmalonamide (Compound 211);

N1-hydroxy-2-(4-(5-hydroxyhexa-1,3-diynyl)-N-methylbenzamido)-N3-methylmalonamide (Compound 212);

2-(4-(5,6-dihydroxyhexa-1,3-diynyl)-N-methylbenzamido)-N1-hydroxy-N3-methylmalonamide (Compound 213);

2-(4-(6,7-dihydroxyhepta-1,3-diynyl)-N-methylbenzamido)-N1-hydroxy-N3-methylmalonamide (Compound 214);

N1-hydroxy-2-(4-(6-hydroxy-5-methylhexa-1,3-diynyl)-N-methylbenzamido)-N3-methylmalonamide (Compound 215);

N1-hydroxy-2-(4-((3-hydroxycyclobutyl)buta-1,3-diynyl)-N-methylbenzamido)-N3-methylmalonamide (Compound 216);

N1-hydroxy-2-(4-((3-(hydroxymethyl)cyclobutyl)buta-1,3-diynyl)-N-methylbenzamido)-N3-methylmalonamide (Compound 217);

N1-hydroxy-2-(4-((3-(hydroxymethyl)cyclopentyl)buta-1,3-diynyl)-N-methylbenzamido)-N3-methylmalonamide (Compound 218);

N1-hydroxy-2-(4-(6-hydroxy-5-methoxyhexa-1,3-diynyl)-N-methylbenzamido)-N3-methylmalonamide (Compound 219);

N1-hydroxy-2-(4-(7-hydroxy-6-methoxyhepta-1,3-diynyl)-N-methylbenzamido)-N3-methylmalonamide (Compound 220);

N1-hydroxy-2-(4-((2-(hydroxymethyl)cyclopropyl)buta-1,3-diynyl)benzamido)-N3,2-dimethylmalonamide (Compound 221);

N1-hydroxy-2-(4-(5-hydroxypenta-1,3-diynyl)benzamido)-N3,2-dimethylmalonamide (Compound 222);

N1-hydroxy-2-(4-(6-hydroxyhexa-1,3-diynyl)benzamido)-N3,2-dimethylmalonamide (Compound 223);

N1-hydroxy-2-(4-(5-hydroxyhexa-1,3-diynyl)benzamido)-N3,2-dimethylmalonamide (Compound 224);

2-(4-(5,6-dihydroxyhexa-1,3-diynyl)benzamido)-N1-hydroxy-N3,2-dimethylmalonamide (Compound 225);

2-(4-(6,7-dihydroxyhepta-1,3-diynyl)benzamido)-N1-hydroxy-N3,2-dimethylmalonamide (Compound 226);

N1-hydroxy-2-(4-(6-hydroxy-5-methylhexa-1,3-diynyl)benzamido)-N3,2-dimethylmalonamide (Compound 227);

N1-hydroxy-2-(4-((3-hydroxycyclobutyl)buta-1,3-diynyl)benzamido)-N3,2-dimethylmalonamide (Compound 228);

N1-hydroxy-2-(4-((3-(hydroxymethyl)cyclobutyl)buta-1,3-diynyl)benzamido)-N3,2-dimethylmalonamide (Compound 229);

N1-hydroxy-2-(4-((3-(hydroxymethyl)cyclopentyl)buta-1,3-diynyl)benzamido)-N3,2-dimethylmalonamide (Compound 230);

N1-hydroxy-2-(4-(6-hydroxy-5-methoxyhexa-1,3-diynyl)benzamido)-N3,2-dimethylmalonamide (Compound 231);

N1-hydroxy-2-(4-(7-hydroxy-6-methoxyhepta-1,3-diynyl)benzamido)-N3,2-dimethylmalonamide (Compound 232);

N1-hydroxy-2-(4-((2-(hydroxymethyl)cyclopropyl)buta-1,3-diynyl)-N-methylbenzamido)-N3,2-dimethylmalonamide (Compound 233);

N1-hydroxy-2-(4-(5-hydroxypenta-1,3-diynyl)-N-methylbenzamido)-N3,2-dimethylmalonamide (Compound 234);

N1-hydroxy-2-(4-(6-hydroxyhexa-1,3-diynyl)-N-methylbenzamido)-N3,2-dimethylmalonamide (Compound 235);

N1-hydroxy-2-(4-(5-hydroxyhexa-1,3-diynyl)-N-methylbenzamido)-N3,2-dimethylmalonamide (Compound 236);

2-(4-(5,6-dihydroxyhexa-1,3-diynyl)-N-methylbenzamido)-N1-hydroxy-N3,2-dimethylmalonamide (Compound 237);

2-(4-(6,7-dihydroxyhepta-1,3-diynyl)-N-methylbenzamido)-N1-hydroxy-N3,2-dimethylmalonamide (Compound 238);

N1-hydroxy-2-(4-(6-hydroxy-5-methylhexa-1,3-diynyl)-N-methylbenzamido)-N3,2-dimethylmalonamide (Compound 239);

N1-hydroxy-2-(4-((3-hydroxycyclobutyl)buta-1,3-diynyl)-N-methylbenzamido)-N3,2-dimethylmalonamide (Compound 240);

N1-hydroxy-2-(4-((3-(hydroxymethyl)cyclobutyl)buta-1,3-diynyl)-N-methylbenzamido)-N3,2-dimethylmalonamide (Compound 241);

N1-hydroxy-2-(4-((3-(hydroxymethyl)cyclopentyl)buta-1,3-diynyl)-N-methylbenzamido)-N3,2-dimethylmalonamide (Compound 242);

N1-hydroxy-2-(4-(6-hydroxy-5-methoxyhexa-1,3-diynyl)-N-methylbenzamido)-N3,2-dimethylmalonamide (Compound 243); and N1-hydroxy-2-(4-(7-hydroxy-6-methoxyhepta-1,3-diynyl)-N-methylbenzamido)-N3,2-dimethylmalonamide (Compound 244).

20. A compound having the following structure:

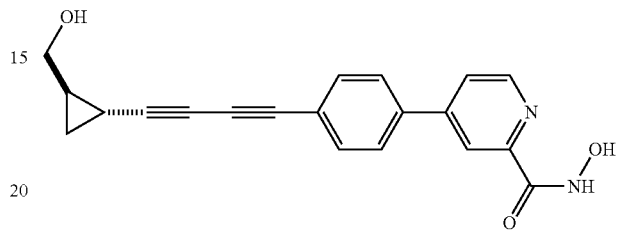

or a stereoisomer or pharmaceutically acceptable salt thereof.

* * * * *